US009637796B2

(12) United States Patent
Vogelstein et al.

(10) Patent No.: US 9,637,796 B2
(45) Date of Patent: May 2, 2017

(54) DIFFERENTIAL IDENTIFICATION OF PANCREATIC CYSTS

(71) Applicant: THE JOHNS HOPKINS UNIVERSITY, Baltimore, MD (US)

(72) Inventors: Bert Vogelstein, Baltimore, MD (US); Kenneth W. Kinzler, Baltimore, MD (US); Nickolas Papadopoulos, Towson, MD (US); Jian Wu, Baltimore, MD (US); Ralph Hruban, Baltimore, MD (US); Anirban Maitra, Baltimore, MD (US); Marco Dal Molin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/359,149

(22) PCT Filed: Nov. 12, 2012

(86) PCT No.: PCT/US2012/064629
§ 371 (c)(1),
(2) Date: May 19, 2014

(87) PCT Pub. No.: WO2013/074438
PCT Pub. Date: May 23, 2013

(65) Prior Publication Data
US 2014/0323344 A1    Oct. 30, 2014

(51) Int. Cl.
*C12Q 1/68* (2006.01)
(52) U.S. Cl.
CPC ......... *C12Q 1/6886* (2013.01); *C12Q 1/6883* (2013.01); *C12Q 2600/156* (2013.01)
(58) Field of Classification Search
CPC ................ C12C 1/6886; C12C 1/6883; C12C 2600/156
See application file for complete search history.

(56) References Cited

U.S. PATENT DOCUMENTS 6,312,890 B1    11/2001  Linehan et al.
2006/0088870 A1*  4/2006  Finkelstein et al. ............. 435/6
2011/0269640 A1  11/2011  Xu et al.

FOREIGN PATENT DOCUMENTS

WO    2006047482 A2    5/2006
WO    2011031892 A1    3/2011

OTHER PUBLICATIONS

Taneka et al., Frequent β-Catenin Mutation and Cytoplasmic/Nuclear Accumulation in Pancreatic Solid-Pseudopapillary Neoplasm, Cancer Research 61, 8401-8404, Dec. 1, 2001.*

(Continued)

*Primary Examiner* — Reza Ghafoorian
(74) *Attorney, Agent, or Firm* — Banner & Witcoff, Ltd.

(57) ABSTRACT

More than 2% of adults harbor a pancreatic cyst, a subset of which progress to invasive lesions with lethal consequences. To assess the genomic landscapes of neoplastic cysts of the pancreas, we determined the exomic sequences of DNA from the neoplastic epithelium of eight surgically resected cysts of each of the major neoplastic cyst types: serous cystadenomas (SCAs), intraductal papillary mucinous neoplasms (IPMNs), mucinous cystic neoplasms (MCNs) and solid pseudo-papillary neoplasms (SPNs). SPNs are low-grade malignancies, and IPMNs and MCNs, but not SCAs, have the capacity to progress to cancer. We found that SCAs, IPMNs, MCNs, and SPNs contained 10=4.6, 27=12, 16=7.6, and 2.9=2.1 somatic mutations per tumor, respectively. Among the mutations identified, E3 ubiquitin ligase components were of particular note. Four of the eight SCAs contained mutations of VHL, a key component of the VHL ubiquitin ligase complex that has previously been associated both with renal cell carcinomas, SCAs, and other neoplasms. Six of the eight IPMNs and three of the eight MCNs harbored mutations of RNF43, a gene coding for a protein with intrinsic E3 ubiquitin ligase activity that has not (Continued)

previously been found to be genetically altered in any human cancer. The preponderance of inactivating mutations in RNF43 unequivocally establish it as a suppressor of both IPMNs and MCNs. SPNs contained remarkably few genetic alterations, but always contained mutations of CTNNB1, previously demonstrated to inhibit degradation of the encoded protein (β-catenin) by E3 ubiquitin ligases. These results highlight the essential role of ubiquitin ligases in these neoplasms and have important implications for the diagnosis and treatment of patients with cystic tumors.

4 Claims, 36 Drawing Sheets

(56) References Cited

OTHER PUBLICATIONS

Wu et al., 'Recurrent GNAS mutations define an unexpected pathway for pancreatic cyst development' Science Translational Medicine, Jul. 20, 2011, Vol.3, No. 92, p. 92ra66.

Wu et al., 'Whole-exome sequencing of neoplastic cysts of the pancreas reveals recurrent mutations in components of ubiquitin-dependent pathways'; PNAS, Dec. 27, 2011, vol. 108, No. 52, pp. 21188-21193.

International Search Report and Written Opinion mailed Mar. 13, 2013, for PCT/US2012/064629.

Kim et al., "Comparison of Epigenetic and Genetic Alterations in Mucinous Cystic Neoplasm and Serous Microcystic Adenoma of Pancreas," Modern Pathology, 2003, vol. 16, No. 11, pp. 1086-1094.

Office Action issued in related Australian Application No. 2012339835, dated Apr. 10, 2015.

\* cited by examiner (TABLE 1.) RECURRENT GENETIC ALTERATIONS IN NEOPLASTIC CYSTS OF THE PANCREAS

| CYST TYPE | SAMPLE ID | VHL | RNF43 | KRAS | GNAS | CTNNB1 |
|---|---|---|---|---|---|---|
| SCA | SCA 14 | LOH | NONE | NONE | NONE | NONE |
| SCA | SCA 23 | LOH, p.N78S | NONE | NONE | NONE | NONE |
| SCA | SCA 27 | LOH | NONE | NONE | NONE | NONE |
| SCA | SCA 29 | LOH | NONE | NONE | NONE | NONE |
| SCA | SCA 35 | LOH, p.W117L | NONE | NONE | NONE | NONE |
| SCA | SCA 37 | LOH | NONE | NONE | NONE | NONE |
| SCA | SCA 38 | p.C162W | NONE | NONE | NONE | NONE |
| SCA | SCA 40 | LOH, p.S80R | NONE | NONE | NONE | NONE |
| | | | | | | |
| IPMN | IPMN 4 | NONE | NONE | NONE | p.R201C | NONE |
| IPMN | IPMN 11 | NONE | LOH, p.R145X | p.G12D | p.R201C | NONE |
| IPMN | IPMN 12 | NONE | LOH, p.Y177X | NONE | p.R201C | NONE |
| IPMN | IPMN 20 | NONE | p.Q152X | p.G12D | p.R201C | NONE |
| IPMN | IPMN 21 | NONE | LOH, p.R371X | p.G12D | p.R201H | NONE |
| IPMN | IPMN 26 | NONE | NONE | p.G12R | NONE | NONE |
| IPMN | IPMN 36 | NONE | LOH, p.S216X | p.G12R | NONE | NONE |
| IPMN | IPMN 41 | NONE | p.R113X | NONE | NONE | NONE |
| | | | | | | |
| MCN | MCN 158 | NONE | NONE | NONE | NONE | NONE |
| MCN | MCN 162 | NONE | NONE | p.G12V | NONE | NONE |
| MCN | MCN 163 | NONE | NONE | p.G13D | NONE | NONE |
| MCN | MCN 164 | NONE | NONE | p.G12V | NONE | NONE |
| MCN | MCN 166 | NONE | p.R371X | p.G12D | NONE | NONE |
| MCN | MCN 168 | NONE | LOH, p.R127P | p.G12V | NONE | NONE |
| MCN | MCN 169 | NONE | LOH | NONE | NONE | NONE |
| MCN | MCN 170 | NONE | p.S41X | p.G12V | NONE | NONE |
| | | | | | | |
| SPN | SPN 2 | NONE | NONE | NONE | NONE | p.G34R |
| SPN | SPN 4 | NONE | NONE | NONE | NONE | p.S33C |
| SPN | SPN 5 | NONE | NONE | NONE | NONE | p.D32H |
| SPN | SPN 6 | NONE | NONE | NONE | NONE | p.D32A |
| SPN | SPN 8 | NONE | NONE | NONE | NONE | p.S37F |
| SPN | SPN 12 | NONE | NONE | NONE | NONE | p.G34V |
| SPN | SPN 17 | NONE | NONE | NONE | NONE | p.G34R |
| SPN | SPN 19 | NONE | NONE | NONE | NONE | p.D32N |

FIG. 5

[DATASET S4: SOMATIC MUTATIONS IDENTIFIED IN NEOPLASTIC CYSTS OF THE PANCREAS]

| CYST TYPE | GENE | SAMPLE ID | TRANSCRIPT ACCESSION | DISTINCT WT READS | DISTINCT MUTANT READS | % MUTANT READS | NUCLEOTIDE (GENOMIC) | NUCLEOTIDE (cDNA) | AMINO ACID (PROTEIN) | MUTATION TYPE | CHASM SCORE | CHASM p-VALUE | CHASM FDR |
|---|---|---|---|---|---|---|---|---|---|---|---|---|---|
| SCA | C19orf61 | SCA 14 | ENST00000222379 | 131 | 48 | 26.8% | g.chr19:4934628301>C | c.10A>G | p.I4V | MISSENSE | NA** | NA** | NA** |
| SCA | C9orf95 | SCA 14 | ENST00000376794 | 28 | 16 | 36.4% | g.chr9:76971013A>G | c.513T>G | p.G171W | MISSENSE | 0.960 | 0.9000 | 1.00 |
| SCA | C9orf95 | SCA 14 | ENST00000376794 | 29 | 15 | 34.1% | g.chr9:76970899C>T | c.527G>A | p.G176E | MISSENSE | 0.980 | 0.9470 | 1.00 |
| SCA | DCLK3 | SCA 14 | CCDS43064.1 | 334 | 117 | 25.9% | g.chr3:36754346C>T | c.809G>A | p.S270N | MISSENSE | 0.892 | 0.6400 | 0.95 |
| SCA | GDF2 | SCA 14 | CCDS7219.1 | 68 | 18 | 20.9% | g.chr10:48036638T>G | c.62A>C | p.Q21P | MISSENSE | 0.912 | 0.7620 | 1.00 |
| SCA | MAGEC1 | SCA 14 | CCDS35417.1 | 32 | 10 | 23.8% | g.chrX:140822047C>G | c.1191C>G | p.H397Q | MISSENSE | 0.990 | 0.9750 | 1.00 |
| SCA | PDE4D | SCA 14 | NM_001104631 | 454 | 146 | 24.3% | g.chr5:58306391C>G | c.2289G>C | p.S763I | MISSENSE | 0.872 | 0.6000 | 0.90 |
| SCA | RBMX | SCA 14 | CCDS14611.1 | 85 | 28 | 24.8% | g.chrX:135789226C>G | c.27G>C | p.K9N | MISSENSE | 0.880 | 0.6310 | 0.95 |
| SCA | SLC26A1 | SCA 14 | CCDS3934.1 | 49 | 14 | 22.2% | g.chr4:973867C>T | c.860G>A | p.R287H | MISSENSE | 0.982 | 0.9620 | 1.00 |
| SCA | STRN | SCA 14 | CCDS1784.1 | 37 | 10 | 21.3% | g.chr2:37005846C>T | c.244G>A | p.A82T | MISSENSE | 0.846 | 0.4910 | 0.90 |
| SCA | AGK | SCA 23 | CCDS5865.1 | 52 | 8 | 13.3% | g.chr7:140957534G>A | c.368G>A | p.G123E | MISSENSE | 0.132 | 0.0010 | 0.05 |
| SCA | ANKRD36B | SCA 23 | NM_025190 | 10 | 8 | 44.4% | g.chr2:97494425C>T | c.3928G>A | p.G1110R | MISSENSE | 0.892 | 0.6610 | 0.95 |
| SCA | AXL | SCA 23 | CCDS12375.1 | 462 | 105 | 17.9% | g.chr19:46441394A>C | c.1479A>C | p.E493D | MISSENSE | 0.988 | 0.9680 | 1.00 |
| SCA | FAM161A | SCA 23 | CCDS42697.1 | 71 | 20 | 22.0% | g.chr2:61916659C>T | c.1346G>A | p.R449K | MISSENSE | 0.856 | 0.5320 | 0.90 |
| SCA | FAM161A | SCA 23 | CCDS42697.1 | 71 | 20 | 22.0% | g.chr2:61916657C>T | c.1348G>A | p.V450I | MISSENSE | 0.859 | 0.5410 | 0.90 |
| SCA | FAM91A1 | SCA 23 | CCDS56246.2 | 36 | 8 | 18.2% | g.chr8:124860155G>T | c.511C>T | p.V171L | MISSENSE | 0.804 | 0.5610 | 0.90 |
| SCA | GGT1 | SCA 23 | CCDS42982.1 | 88 | 17 | 16.2% | g.chr22:23372102A>G | c.184A>G | p.K62E | MISSENSE | 0.736 | 0.1950 | 0.70 |
| SCA | HSPG2 | SCA 23 | CCDS30825.1 | 115 | 29 | 20.1% | g.chr1:22075613G>C | c.2805C>G | p.S935R | MISSENSE | 0.878 | 0.6220 | 0.90 |
| SCA | IKBKAP | SCA 23 | CCDS6773.1 | 114 | 27 | 19.1% | g.chr9:111068220G>T | c.3409C>A | p.R1137S | MISSENSE | 0.702 | 0.1450 | 0.65 |
| SCA | KIAA1267 | SCA 23 | CCDS11303.1 | 187 | 30 | 13.8% | g.chr17:41609484A>C | c.333T>G | p.H111Q | MISSENSE | 0.982 | 0.9520 | 1.00 |
| SCA | PCDHB13 | SCA 23 | CCDS4255.1 | 403 | 86 | 17.6% | g.chr5:140578489G>T | c.1610G>T | p.C537V | MISSENSE | 0.912 | 0.7620 | 1.00 |
| SCA | POTEG | SCA 23 | ENST00000409632 | 44 | 8 | 15.4% | g.chr12:14097148580>T | c.808G>A | p.V280I | MISSENSE | 0.546 | 0.0440 | 0.35 |
| SCA | SYAP1 | SCA 23 | CCDS14177.1 | 56 | 33 | 37.1% | g.chrX:16685234G>A | c.812C>A | p.G271D | MISSENSE | 0.816 | 0.3850 | 0.85 |
| SCA | TLR2 | SCA 23 | CCDS3784.1 | 36 | 13 | 26.5% | g.chr4:154844219T>C | c.710T>C | p.F237S | MISSENSE | 0.816 | 0.3850 | 0.65 |
| SCA | TRIM73 | SCA 23 | CCDS34865.1 | 29 | 11 | 27.5% | g.chr7:74606370T>A | c.217T>A | p.W73R | MISSENSE | 0.762 | 0.2400 | 0.75 |

FIG. 6

| | | | | | | | | | | |
|---|---|---|---|---|---|---|---|---|---|---|
| SCA | VHL | SCA 23 | CCDS2597.1 | 65 | 22 | 25.3% | g.chr3:10159076A>G | c.233A>G | p.N78S | MISSENSE | 0.006** | 0.0000 | 0.05 |
| SCA | ZNF574 | SCA 23 | CCDS12596.1 | 282 | 76 | 21.1% | g.chr19:42756216C>G | c.1023C>G | p.C341W | MISSENSE | 0.826 | 0.4170 | 0.85 |
| SCA | ADAMTS19 | SCA 27 | CCDS4146.1 | 118 | 24 | 16.9% | g.chr5:129006030890C>T | c.3046C>T | p.R1016X | NONSENSE | 0.000 | 0.0000 | 0.00 |
| SCA | ANKRD20A4 | SCA 27 | CCDS43828.1 | 20 | 5 | 20.0% | g.chr9:68718805G>T | c.2266G>T | p.D756Y | MISSENSE | 0.720 | 0.1710 | 0.65 |
| SCA | ANKRD20A4 | SCA 27 | CCDS43828.1 | 28 | 5 | 15.2% | g.chr9:68718805G>A | c.2281G>A | p.D756Y | MISSENSE | 0.780 | 0.2040 | 0.80 |
| SCA | ANKRD20B | SCA 27 | CCDS43828.1 | 20 | 5 | 20.0% | g.chr9:68718805G>T | c.2266G>T | p.D756Y | MISSENSE | 0.720 | 0.1710 | 0.65 |
| SCA | ANKRD20B | SCA 27 | CCDS43828.1 | 28 | 5 | 15.2% | g.chr9:68718805G>A | c.2281G>A | p.V761I | MISSENSE | 0.780 | 0.2840 | 0.80 |
| SCA | ARHGEF11 | SCA 27 | CCDS1163.1 | 135 | 39 | 22.4% | g.chr1:155179170T>C | c.3262A>G | p.T1088A | MISSENSE | 0.994 | 0.9300 | 1.00 |
| SCA | CTNND2 | SCA 27 | CCDS3881.1 | 144 | 31 | 17.7% | g.chr5:11099082C>T | c.1430G>A | p.G477D | MISSENSE | 0.790 | 0.3080 | 0.80 |
| SCA | NCOR2 | SCA 27 | CCDS41658.1 | 50 | 13 | 20.6% | g.chr12:123971836G>A | c.430T>C | p.P143L | MISSENSE | 0.974 | 0.9530 | 1.00 |
| SCA | TBC1D3F | SCA 27 | ENST00000027454 | 8 | 4 | 33.3% | g.chr17:33363578C>T | c.742C>T | p.P248S | MISSENSE | 0.882 | 0.6400 | 0.95 |
| SCA | XAGE3 | SCA 27 | CCDS14247.1 | 14 | 4 | 22.2% | g.chrX:52908378A>G | c.1>C | 3'UTR | | NAS | NAS | NAS |
| SCA | XKR3 | SCA 27 | CCDS42975.1 | 57 | 13 | 18.6% | g.chr22:16645174T>T | c.715G>A | p.Y239M | MISSENSE | 0.899 | 0.6730 | 0.95 |
| SCA | HBZP1 | SCA 29 | ENST00000354915 | 3 | 5 | 62.5% | g.chr16:155106C>A | c.356C>A | p.A119D | MISSENSE | NA** | NA** | NA** |
| SCA | RIC3A | SCA 29 | CCDS7680.1 | 122 | 22 | 15.3% | g.chr11:1202948C>A | c.134C>A | p.T47K | MISSENSE | 0.808 | 0.3610 | 0.85 |
| SCA | ATP6B4 | SCA 35 | CCDS2238.1 | 18 | 4 | 18.2% | g.chr15:47977718A>T | c.2312T>A | p.V771D | MISSENSE | 0.732 | 0.1900 | 0.65 |
| SCA | ESAM | SCA 35 | CCDS8453.1 | 24 | 10 | 29.4% | g.chr11:124108862G>A | c.1C>T | SpliceAcceptor | | NASS | NASS | NASS |
| SCA | FAM47C | SCA 35 | CCDS35227.1 | 30 | 13 | 30.2% | g.chrX:36939129G>T | c.2726G>T | p.V909F | MISSENSE | 0.996 | 0.9950 | 1.00 |
| SCA | FNDC1 | SCA 35 | NM_032532 | 198 | 34 | 14.7% | g.chr6:159360949A>C | c.4591A>C | p.N1531H | MISSENSE | 0.864 | 0.5610 | 0.90 |
| SCA | NLRP12 | SCA 35 | CCDS12664.1 | 68 | 26 | 27.7% | g.chr19:59099638C>T | c.2665C>A | p.L889M | MISSENSE | 0.812 | 0.3730 | 0.85 |
| SCA | OR3A2 | SCA 35 | CCDS42233.1 | 14 | 4 | 22.2% | g.chr17:3128837G>A | c.143C>T | p.T48I | MISSENSE | 0.746 | 0.2100 | 0.70 |
| SCA | PCDH9 | SCA 35 | CCDS9444.1 | 78 | 13 | 14.3% | g.chr13:66698823A>T | c.2051T>A | p.F684Y | MISSENSE | 0.786 | 0.2970 | 0.80 |
| SCA | PRKCSH | SCA 35 | CCDS12911.1 | 106 | 33 | 23.7% | g.chr19:11420349C>G | c.1399C>G | p.Q467E | MISSENSE | 0.254 | 0.0050 | 0.10 |
| SCA | STAG3L2 | SCA 35 | NM_001025202 | 14 | 4 | 22.2% | g.chr7:79036305G>A | c.238C>T | p.R80C | MISSENSE | 0.992 | 0.9820 | 1.00 |
| SCA | TEX2 | SCA 35 | CCDS11658.1 | 28 | 13 | 31.7% | g.chr17:59644156G>A | c.1194C>G | p.S365F | MISSENSE | 0.848 | 0.4990 | 0.90 |
| SCA | VHL | SCA 35 | CCDS2591.1 | 58 | 21 | 26.6% | g.chr3:10163207G>T | c.350G>T | p.W117L | MISSENSE | 0.000* | 0.0000 | 0.05 |
| SCA | ATP11B | SCA 37 | CCDS3396.1 | 34 | 14 | 29.2% | g.chr3:184066050C>A | c.1513C>A | p.P438H | MISSENSE | 0.832 | 0.4350 | 0.85 |
| SCA | BMPR1B | SCA 37 | CCDS3642.1 | 37 | 6 | 14.0% | g.chr4:96267012G>A | c.671G>A | p.R224H | MISSENSE | 0.310 | 0.0080 | 0.15 |
| SCA | C18orf55 | SCA 37 | CCDS12003.1 | 78 | 29 | 27.1% | g.chr18:69867164T>A | c.1411T>A | p.Y47X | NONSENSE | 0.000 | 0.0000 | 0.00 |
| SCA | CBL | SCA 37 | CCDS9418.1 | 14 | 5 | 26.3% | g.chr11:11064977989A>C | c.592A>C | p.T198P | MISSENSE | 0.494 | 0.0310 | 0.30 |

FIG. 6 CONTINUED

| | | | | | | | | | | NASS | NASS |
|---|---|---|---|---|---|---|---|---|---|---|---|
| SCA | MAMDC4 | SCA 37 | CCDS7410.1 | 85 | 21 | 19.8% | g.chr9:130660352A>G | c.-1A>G | SpliceDonor | MISSENSE | 0.946 | 0.8640 | 1.00 |
| SCA | MYEOV2 | SCA 37 | CCDS2532.1 | 57 | 10 | 14.9% | g.chr2:240722033G>T | c.219C>A | p.D73E | MISSENSE | 0.916 | 0.7770 | 1.00 |
| SCA | SAMD10 | SCA 37 | CCDS13549.1 | 108 | 18 | 14.3% | g.chr20:62078091G>C | c.322C>G | p.L108V | MISSENSE | 0.746 | 0.2100 | 0.70 |
| SCA | SERPINA3 | SCA 37 | CCDS32150.1 | 169 | 38 | 16.7% | g.chr14:94151639A>T | c.158A>T | p.N53I | MISSENSE | 0.586 | 0.0580 | 0.40 |
| SCA | SGK2 | SCA 37 | CCDS13320.1 | 99 | 24 | 19.5% | g.chr20:41629726C>G | c.274C>G | p.P92A | MISSENSE | 0.902 | 0.7240 | 1.00 |
| SCA | SLITRK4 | SCA 37 | CCDS14679.1 | 10 | 10 | 50.0% | g.chrX:142546065G>T | c.536C>A | p.S179Y | MISSENSE | 0.826 | 0.4170 | 0.85 |
| SCA | TAF6 | SCA 37 | CCDS5686.1 | 212 | 51 | 19.4% | g.chr7:99348036G>T | c.74C>A | p.S25Y | MISSENSE | 0.724 | 0.1760 | 0.65 |
| SCA | BCL2L1 | SCA 38 | CCDS13189.1 | 38 | 17 | 30.9% | g.chr20:29717465C>T | c.650G>A | p.G217D | MISSENSE | 0.736 | 0.3240 | 0.80 |
| SCA | IGSF8 | SCA 38 | CCDS1195.1 | 69 | 22 | 24.2% | g.chr1:158331394C>T | c.331G>A | p.V111M | MISSENSE | 0.860 | 0.5470 | 0.90 |
| SCA | TBC1D3F | SCA 38 | ENST00000327454 | 28 | 4 | 12.5% | g.chr17:33353946C>T | c.2C>T | p.A1V | MISSENSE | 0.928 | 0.8110 | 1.00 |
| SCA | TTN | SCA 38 | ENST00000375038 | 53 | 15 | 22.1% | g.chr2:179461130>T | c.619935G>A | p.R2031H | MISSENSE | 0.002* | 0.0000 | 0.05 |
| SCA | VHL | SCA 39 | CCDS2597.1 | 31 | 4 | 11.4% | g.chr3:10160493C>G | c.486C>G | p.C162W | MISSENSE | 0.790 | 0.3080 | 0.80 |
| SCA | ANKRD11 | SCA 40 | CCDS32513.1 | 68 | 19 | 21.8% | g.chr16:87877222T>C | c.3229A>G | p.K1077E | MISSENSE | 0.940 | 0.8460 | 1.00 |
| SCA | AP3S1 | SCA 40 | CCDS4123.1 | 14 | 4 | 22.2% | g.chr5:115266569A>G | c.434A>G | p.N145S | MISSENSE | 0.542 | 0.0420 | 0.35 |
| SCA | ARL8B | SCA 40 | CCDS2666.1 | 77 | 21 | 21.4% | g.chr3:5139224T>G | c.74T>G | p.I25R | MISSENSE | 0.986 | 0.9130 | 1.00 |
| SCA | CDC42BPB | SCA 40 | ENST00000382988 | 16 | 6 | 27.3% | g.chr14:103594463C>A | c.207C>A | p.S79R | MISSENSE | 0.884 | 0.5610 | 0.90 |
| SCA | CONMD5 | SCA 40 | CCDS10436.1 | 27 | 7 | 20.6% | g.chr8:146047089C>G | c.439G>C | p.A147P | NONSENSE | 0.000 | 0.0000 | 0.00 |
| SCA | DYRK1A | SCA 40 | CCDS42925.1 | 34 | 13 | 27.7% | g.chr21:37774946G>A | c.464G>A | p.W155X | MISSENSE | 0.902 | 0.7240 | 1.00 |
| SCA | ERC1 | SCA 40 | CCDS8608.1 | 92 | 33 | 26.4% | g.chr12:1007700G>A | c.370G>A | p.A124T | MISSENSE | 0.876 | 0.6140 | 0.90 |
| SCA | IGS6 | SCA 40 | CCDS2212.1 | 30 | 11 | 26.8% | g.chr2:160761051G>C | c.268C>G | p.L90V | MISSENSE | 0.910 | 0.7550 | 1.00 |
| SCA | MOCS1 | SCA 40 | CCDS4945.1 | 28 | 11 | 28.2% | g.chr6:39991811C>G | c.562G>C | p.E188Q | MISSENSE | 0.952 | 0.8800 | 1.00 |
| SCA | RNF128 | SCA 40 | CCDS14520.1 | 10 | 14 | 58.3% | g.chrX:105823970A>G | c.82A>G | p.M28V | MISSENSE | 0.816 | 0.3850 | 0.85 |
| SCA | TTC29 | SCA 40 | NM_031956 | 72 | 24 | 25.0% | g.chr4:148080441G>C | c.58C>G | p.Q20E | MISSENSE | 0.044* | 0.0000 | 0.05 |
| SCA | VHL | SCA 40 | CCDS2597.1 | 27 | 12 | 30.8% | g.chr3:10158771T>G | c.2401T>G | p.S801R | MISSENSE | | | |

FIG. 6
CONTINUED

| | | | | | | | | | | |
|---|---|---|---|---|---|---|---|---|---|---|
| IPMN | ADAMTSL3 | IPMN 11 | CCDS10326.1 | 54 | 45 | 45.5% | g.chr15:82278660C>T | c.457C>T | p.R153X | NONSENSE | 0.000 | 0.0000 | 0.00 |
| IPMN | ANAPC1 | IPMN 11 | CCDS2093.1 | 23 | 6 | 20.7% | g.chr2:112247066C>G | c.670G>C | p.V224L | MISSENSE | 0.704 | 0.1460 | 0.65 |
| IPMN | ASPM | IPMN 11 | CCDS1399.1 | 12 | 9 | 42.9% | g.chr1:195226094C>T | c.1093G>A | p.R398H | MISSENSE | 0.938 | 0.8390 | 1.00 |
| IPMN | ATAD5 | IPMN 11 | CCDS11260.1 | 47 | 23 | 32.9% | g.chr17:29185542C>G | c.317C>G | p.S106R | NONSENSE | 0.000 | 0.0000 | 0.00 |
| IPMN | CD14 | IPMN 11 | CCDS4232.1 | 151 | 72 | 32.3% | g.chr5:139992259T>C | c.494A>G | p.Q165R | MISSENSE | 0.060 | 0.5470 | 0.90 |
| IPMN | CHD3 | IPMN 11 | CCDS2653.1 | 69 | 36 | 30.7% | g.chr17:7449180G>G | c.310T>G | p.F104G | MISSENSE | 0.724 | 0.1760 | 0.65 |
| IPMN | CPAMD8 | IPMN 11 | CCDS42519.1 | 95 | 42 | 30.7% | g.chr19:16999394T>C | c.281A>G | p.E94G | MISSENSE | 0.816 | 0.3050 | 0.85 |
| IPMN | DHRS7B | IPMN 11 | CCDS11215.1 | 427 | 122 | 22.2% | g.chr7:21032661G>A | c.665G>A | p.R222H | MISSENSE | 0.668 | 0.5810 | 0.90 |
| IPMN | ECT2 | IPMN 11 | CCDS3220.1 | 46 | 22 | 31.4% | g.chr3:173984433G>A | c.952G>A | p.E318K | MISSENSE | 0.532 | 0.0390 | 0.35 |
| IPMN | EFHC1 | IPMN 11 | CCDS4942.1 | 19 | 17 | 47.2% | g.chr6:52462949A>G | c.1663A>G | p.I555A | MISSENSE | 0.938 | 0.9880 | 1.00 |
| IPMN | EPHB6 | IPMN 11 | CCDS5873.1 | 61 | 106 | 63.5% | g.chr7:142764468C>T | c.2110C>T | p.R704W | MISSENSE | 0.550 | 0.0440 | 0.35 |
| IPMN | EXPH5 | IPMN 11 | CCDS9341.1 | 36 | 24 | 40.0% | g.chr11:108745452G>A | c.3092C>T | p.A1331V | MISSENSE | 0.992 | 0.9820 | 1.00 |
| IPMN | FOXA3 | IPMN 11 | CCDS12677.1 | 129 | 86 | 40.0% | g.chr19:51067615T>G | c.512T>G | p.F171S | MISSENSE | 0.564 | 0.0630 | 0.35 |
| IPMN | GEMIN6 | IPMN 11 | CCDS17893.1 | 87 | 32 | 26.9% | g.chr2:3862263G>C | c.230G>C | p.R77T | MISSENSE | 0.806 | 0.3540 | 0.85 |
| IPMN | GNAS | IPMN 11 | CCDS13472.1 | 55 | 59 | 51.8% | g.chr20:569178150C>T | c.601A>C | p.R201C | MISSENSE | 0.668 | 0.1120 | 0.55 |
| IPMN | GPR98 | IPMN 11 | NM_032119 | 98 | 69 | 41.8% | g.chr5:90225713A>T | c.7164A>T | p.D2395V | MISSENSE | 0.766 | 0.2490 | 0.75 |
| IPMN | INPP1 | IPMN 11 | CCDS62131 | 68 | 38 | 35.8% | g.chr1:176201089G>A | c.-1G>A | SpliceAcceptor | MISSENSE | NASS | NASS | NASS |
| IPMN | ITGA6 | IPMN 11 | CCDS2249.1 | 62 | 17 | 21.5% | g.chr2:173040231T>G | c.603T>G | p.H201Q | MISSENSE | 0.662 | 0.1060 | 0.55 |
| IPMN | ITLN2 | IPMN 11 | CCDS7212.1 | 149 | 88 | 37.3% | g.chr1:163187560C>G | c.332G>C | p.R111P | MISSENSE | 0.478 | 0.0260 | 0.30 |
| IPMN | LRRC37A3 | IPMN 11 | CCDS32708.1 | 11 | 4 | 26.7% | g.chr17:60283373G>A | c.4795C>T | p.L1599F | MISSENSE | 0.734 | 0.1910 | 0.65 |
| IPMN | LRRTM1 | IPMN 11 | CCDS1966.1 | 79 | 39 | 33.1% | g.chr2:80320380C>T | c.1468G>A | p.V490I | MISSENSE | 0.832 | 0.4350 | 0.85 |
| IPMN | NFAP3L | IPMN 11 | CCDS34103.1 | 151 | 70 | 31.7% | g.chr4:171499142C>T | c.422G>A | p.R141H | MISSENSE | 0.538 | 0.0410 | 0.35 |
| IPMN | MGAT5 | IPMN 11 | CCDS1771.1 | 46 | 26 | 36.1% | g.chr2:134744472G>A | c.287G>A | p.R96H | MISSENSE | 0.770 | 0.2590 | 0.80 |
| IPMN | MRAS | IPMN 11 | CCDS3100.1 | 110 | 70 | 38.9% | g.chr3:139800012C>T | c.359C>T | p.P120L | MISSENSE | 0.700 | 0.1420 | 0.65 |
| IPMN | MYCN | IPMN 11 | CCDS1827.1 | 66 | 58 | 46.8% | g.chr2:16099768C>T | c.131C>T | p.P44L | MISSENSE | 0.820 | 0.3970 | 0.85 |
| IPMN | NOX3 | IPMN 11 | CCDS5260.1 | 168 | 51 | 23.3% | g.chr6:155791780C>A | c.985G>T | p.A329S | MISSENSE | 0.872 | 0.6000 | 0.90 |
| IPMN | OD23 | IPMN 11 | NM_001063477 | 186 | 117 | 38.6% | g.chr4:183482234G>A | c.167G>A | p.R56Q | MISSENSE | 0.568 | 0.0520 | 0.35 |
| IPMN | RNF43 | IPMN 11 | CCDS11607.1 | 290 | 208 | 50.7% | g.chr17:5378969G>A | c.433C>T | p.R145X | NONSENSE | 0.000 | 0.0000 | 0.00 |
| IPMN | SLC2A9 | IPMN 11 | CCDS9408.1 | 16 | 5 | 23.8% | g.chr4:9636666C>T | c.21C>A | p.D7E | MISSENSE | 0.850 | 0.5060 | 0.90 |
| IPMN | SLC30A3 | IPMN 11 | CCDS1743.1 | 81 | 82 | 50.3% | g.chr2:27328263C>T | c.893G>A | p.R298H | MISSENSE | 0.950 | 0.8750 | 1.00 |

FIG. 6 CONTINUED

| | | | | | | | | | | |
|---|---|---|---|---|---|---|---|---|---|---|
| PMN | SMO | PMN 11 | CCDS5811.1 | 46 | 61 | 57.0% | g.chr7:128628247G>G | c.734C>G | p.T245R | MISSENSE | 0.744 | 0.2060 | 0.70 |
| PMN | THBS1 | PMN 11 | CCDS32194.1 | 83 | 62 | 42.8% | g.chr15:37661944G>T | c.326G>T | p.R109L | MISSENSE | 0.726 | 0.1830 | 0.65 |
| PMN | ZNHIT3 | PMN 11 | CCDS11312.1 | 245 | 160 | 39.5% | g.chr17:31916657A>G | c.1A>G | p.M1V | MISSENSE | 0.824 | 0.4110 | 0.85 |
| PMN | KRAS | PMN 11 | CCDS8703.1 | 340 | 114 | 25.1% | g.chr12:25289552C>G | c.35G>A | p.G12D | MISSENSE | 0.152* | 0.0010 | 0.05 |
| PMN | CCDC40 | PMN 12 | ENST00000374877 | 8 | 4 | 33.3% | g.chr17:72678510G>C | c.2910G>C | p.K970N | MISSENSE | 0.974 | 0.3330 | 1.00 |
| PMN | CDYL2 | PMN 12 | CCDS2493.1 | 154 | 53 | 25.6% | g.chr16:7204400G>A | c.1142C>T | p.T381M | MISSENSE | 0.846 | 0.4910 | 0.90 |
| PMN | CNTNAP5B | PMN 12 | ENST00000077564 | 19 | 6 | 24.0% | g.chr9:43824172C>T | c.2852C>T | p.T951M | MISSENSE | 0.748 | 0.2160 | 0.70 |
| PMN | DMRTA2 | PMN 12 | ENST00000371916 | 16 | 7 | 30.4% | g.chr1:50659535G>A | c.236G>T | p.T79M | MISSENSE | 0.782 | 0.2890 | 0.80 |
| PMN | EBF2 | PMN 12 | CCDS43726.1 | 111 | 62 | 35.8% | g.chr8:25774632T>A | c.1192A>T | p.I398F | MISSENSE | 0.616 | 0.0770 | 0.45 |
| PMN | EPHA6 | PMN 12 | CCDS5513.1 | 72 | 30 | 29.4% | g.chr1:4668974G>T | c.2467C>T | p.R820W | MISSENSE | 0.232 | 0.0040 | 0.10 |
| PMN | FAM123B | PMN 12 | CCDS14377.2 | 87 | 24 | 21.6% | g.chrX:63328679C>T | c.1213G>A | p.D405N | MISSENSE | 0.788 | 0.3020 | 0.80 |
| PMN | FGF23 | PMN 12 | CCDS8526.1 | 81 | 67 | 45.3% | g.chr12:4349534G>A | c.592C>T | p.R198W | MISSENSE | 0.964 | 0.9090 | 1.00 |
| PMN | FGFR2 | PMN 12 | ENST00000036653 | 250 | 90 | 26.5% | g.chr10:12322862G>A | c.2351G>T | p.P784L | MISSENSE | NA** | NA** | NA** |
| PMN | GNAS | PMN 12 | CCDS13472.1 | 65 | 39 | 37.5% | g.chr20:56917815C>T | c.601C>T | p.R201C | MISSENSE | 0.668 | 0.1120 | 0.55 |
| PMN | I20 | PMN 12 | CCDS1470.1 | 302 | 235 | 43.8% | g.chr1:20510649G>A | c.2701C>A | p.I90X | NONSENSE | 0.000 | 0.0000 | 0.00 |
| PMN | IRS4 | PMN 12 | CCDS14544.1 | 357 | 118 | 24.8% | g.chrX:107822886G>A | c.3363C>T | p.S1122. | MISSENSE | 0.810 | 0.3670 | 0.85 |
| PMN | KIAA0319L | PMN 12 | CCDS390.1 | 121 | 96 | 44.2% | g.chr1:35898510T>T | c.1927G>A | p.V643M | MISSENSE | 0.626 | 0.0820 | 0.50 |
| PMN | KIF13B | PMN 12 | ENST00000357808 | 8 | 5 | 38.5% | g.chr8:29116209G>A | c.-1G>T | SpliceAcceptor | NA$$ | NA$$ | NA$$ |
| PMN | LZTR1 | PMN 12 | CCDS33606.1 | 104 | 49 | 32.0% | g.chr22:19697341T>A | c.226T>A | p.Y76N | MISSENSE | 0.544 | 0.0430 | 0.35 |
| PMN | MFN2 | PMN 12 | CCDS3587.1 | 64 | 22 | 25.6% | g.chr1:11943150G>A | c.2215G>A | p.G739S | MISSENSE | 0.854 | 0.5250 | 0.90 |
| PMN | PSMD6 | PMN 12 | CCDS2930.1 | 78 | 47 | 37.6% | g.chr3:63979715C>T | c.536G>A | p.R179H | MISSENSE | 0.578 | 0.0660 | 0.40 |
| PMN | RDH5 | PMN 12 | CCDS31829.1 | 61 | 46 | 43.0% | g.chr12:54401919G>A | c.490G>A | p.V164I | MISSENSE | 0.356 | 0.0110 | 0.15 |
| PMN | RNF43 | PMN 12 | CCDS11607.1 | 82 | 125 | 60.4% | g.chr17:57998068G>T | c.531C>A | p.Y177X | NONSENSE | 0.000 | 0.0000 | 0.00 |
| PMN | SOMH1 | PMN 12 | CCDS30608.1 | 125 | 60 | 32.4% | g.chr1:41266582C>A | c.-1C>T | SpliceAcceptor | NA$$ | NA$$ | NA$$ |
| PMN | SMPD1 | PMN 12 | CCDS31403.1 | 75 | 34 | 31.2% | g.chr1:16368651C>G | c.115C>G | p.L39V | MISSENSE | 0.906 | 0.7470 | 1.00 |
| PMN | SSBP1 | PMN 12 | CCDS5866.1 | 33 | 14 | 29.8% | g.chr7:41085442C>T | c.7C>T | p.R3X | NONSENSE | 0.000 | 0.0080 | 0.00 |
| PMN | TACR3 | PMN 12 | CCDS3664.1 | 79 | 50 | 38.8% | g.chr4:104732145C>T | c.1033G>A | p.A345T | MISSENSE | 0.564 | 0.0500 | 0.35 |
| PMN | TARBP1 | PMN 12 | CCDS1601.1 | 20 | 9 | 31.0% | g.chr1:22268142G>A | c.53C>T | p.A18V | MISSENSE | 0.852 | 0.5170 | 0.90 |
| PMN | TAS2R50 | PMN 12 | CCDS8638.1 | 61 | 26 | 29.9% | g.chr12:11002221C>T | c.506G>A | p.R169K | MISSENSE | 0.816 | 0.3850 | 0.85 |
| PMN | TCEB3B | PMN 12 | CCDS11923.1 | 320 | 109 | 25.4% | g.chr18:42815246G>A | c.388C>T | p.R130W | MISSENSE | 0.930 | 0.8190 | 1.00 |

FIG. 6 CONTINUED

| | | | | | | | | | | |
|---|---|---|---|---|---|---|---|---|---|---|
| PAN | ADAT3 | PAN 20 | CCDS12078.1 | 19 | | 55.5% | g.chr19:1063172G>A | c.79G>A | p.W26X | NONSENSE | 0.00 | 0.0000 | 0.00 |
| PAN | ARNT2 | PAN 20 | CCDS53207.1 | 483 | 24 | 26.4% | g.chr15:78642526C>T | c.1210G>T | p.R404C | MISSENSE | 0.786 | 0.2970 | 0.50 |
| PAN | C9orf98 | PAN 20 | CCDS35364.1 | 70 | 26 | 27.1% | g.chr9:134693046G>A | c.433C>T | p.R145C | MISSENSE | 0.924 | 0.7890 | 1.00 |
| PAN | DHX38 | PAN 20 | CCDS10907.1 | 287 | 120 | 31.0% | g.chr16:70688341C>A | c.443C>A | p.S148Y | MISSENSE | 0.574 | 0.0530 | 0.35 |
| PAN | EFS | PAN 20 | CCDS9595.1 | 181 | 101 | 35.8% | g.chr14:22864614C>T | c.1547G>A | p.R516Q | MISSENSE | 0.956 | 0.8890 | 1.00 |
| PAN | FRG1 | PAN 20 | CCDS34121.1 | 83 | 23 | 21.7% | g.chr4:191139995C>G | c.654C>G | p.D218E | MISSENSE | 0.380 | 0.0130 | 0.20 |
| PAN | GNAS | PAN 20 | CCDS13472.1 | 78 | 45 | 36.6% | g.chr20:56891731G>T | c.601G>T | p.R201C | MISSENSE | 0.666 | 0.1120 | 0.55 |
| PAN | KLF4 | PAN 20 | CCDS6770.1 | 474 | 130 | 21.5% | g.chr9:108289169T>G | c.1198A>C | p.K400Q | MISSENSE | 0.896 | 0.7000 | 0.95 |
| PAN | NOTCH2 | PAN 20 | ENST00000401649 | 49 | 14 | 22.2% | g.chr1:120340584C>T | c.790G>A | p.G264R | MISSENSE | 0.946 | 0.8840 | 1.00 |
| PAN | PRKCA | PAN 20 | CCDS11684.1 | 72 | 46 | 39.0% | g.chr17:62169275G>A | c.1450G>A | p.E487K | MISSENSE | 0.286 | 0.0080 | 0.15 |
| PAN | RNF43 | PAN 20 | CCDS11807.1 | 530 | 61 | 10.3% | g.chr17:57987803G>A | c.454C>T | p.Q152X | NONSENSE | 0.000 | 0.0000 | 0.00 |
| PAN | SIRPA | PAN 20 | CCDS13022.1 | 104 | 29 | 21.8% | g.chr20:1843360C>C | c.224G>C | p.G75A | MISSENSE | 0.956 | 0.9850 | 1.00 |
| PAN | TDRD6 | PAN 20 | CCDS34470.1 | 151 | 86 | 34.8% | g.chr6:46794630C>T | c.1086C>T | p.R330W | MISSENSE | 0.940 | 0.8460 | 1.00 |
| PAN | TPTE2 | PAN 20 | CCDS9265.1 | 77 | 21 | 21.4% | g.chr13:19961144A>C | c.981T>G | p.L3R | MISSENSE | 0.990 | 0.9750 | 1.00 |
| PAN | KRAS | PAN 20 | CCDS8703.1 | 144 | 53 | 36.6% | g.chr12:25289552C>G | c.36G>A | p.G12D | MISSENSE | 0.132* | 0.0010 | 0.05 |
| PAN | ACTBL2 | PAN 21 | CCDS34163.1 | 92 | 25 | 21.4% | g.chr5:56815683G>C | c.697G>A | p.A233T | MISSENSE | 0.998 | 0.9980 | 1.00 |
| PAN | APC | PAN 21 | CCDS4107.1 | 31 | 18 | 36.7% | g.chr20:184388G>C | c.295C>T | p.R99W | MISSENSE | 0.774 | 0.2860 | 0.80 |
| PAN | ATP1B4 | PAN 21 | CCDS14598.1 | 24 | 7 | 22.6% | g.chrX:119990396G>A | c.466G>A | p.A156T | MISSENSE | 0.864 | 0.6490 | 0.95 |
| PAN | C14orf166B | PAN 21 | ENST00000216453 | 24 | 8 | 25.5% | g.chr14:76404657delT | c.1711delT | fs | DELETION | 0.000 | 0.0000 | 0.00 |
| PAN | CACNA1I | PAN 21 | NM_021096 | 19 | 6 | 24.0% | g.chr22:39380102G>T | c.3088G>T | p.A1030G | MISSENSE | 0.814 | 0.3790 | 0.85 |
| PAN | C5orf2 | PAN 21 | ENST00000408585 | 59 | 18 | 23.4% | g.chr22:18400197G>T | c.1524G>T | p.M508L | MISSENSE | 0.760 | 0.2370 | 0.75 |
| PAN | DCAF15 | PAN 21 | CCDS32926.1 | 29 | 18 | 62.3% | g.chr19:13931872G>A | c.1517G>A | p.G506D | MISSENSE | 0.744 | 0.2060 | 0.70 |
| PAN | DGKH | PAN 21 | CCDS9361.1 | 65 | 35 | 35.0% | g.chr13:41632270A>G | c.853A>G | p.M285V | MISSENSE | 0.716 | 0.1840 | 0.65 |
| PAN | GNAS | PAN 21 | CCDS13472.1 | 88 | 52 | 49.3% | g.chr20:56917816G>A | c.602G>A | p.R201H | MISSENSE | 0.656 | 0.1030 | 0.55 |
| PAN | GRIK4 | PAN 21 | CCDS8431.1 | 18 | 17 | 48.6% | g.chr11:120316369G>A | c.1580G>A | p.R527H | MISSENSE | 0.668 | 0.1120 | 0.55 |
| PAN | HMCN1 | PAN 21 | CCDS30956.1 | 62 | 27 | 30.3% | g.chr1:184425517C>T | c.16792C>T | p.R5598X | NONSENSE | 0.000 | 0.0000 | 0.00 |
| PAN | LF8 | PAN 21 | CCDS2109.1 | 44 | 14 | 24.1% | g.chr2:11589510T/C>T | c.1110G>A | p.D37N | MISSENSE | 0.980 | 0.9470 | 1.00 |
| PAN | KPTN | PAN 21 | CCDS42583.1 | 85 | 40 | 32.0% | g.chr19:52670576C>T | c.1220G>A | p.R407Q | MISSENSE | 0.972 | 0.9290 | 1.00 |
| PAN | KRAS | PAN 21 | CCDS8703.1 | 14 | 7 | 33.3% | g.chr12:25289575C>T | c.35G>A | p.G12D | MISSENSE | 0.132* | 0.0010 | 0.05 |
| PAN | MAP3K12 | PAN 21 | CCDS8660.1 | 56 | 24 | 30.0% | g.chr12:52616575C>T | c.445G>A | p.V149M | MISSENSE | 0.442 | 0.0210 | 0.25 |

FIG. 6 CONTINUED

| | | | | | | | | | NA** | NA** | NA** |
|---|---|---|---|---|---|---|---|---|---|---|---|
| PMN | MED23 | PMN 21 | ENST00000354577 | 28 | 11 | 28.2% | g.chr6:131970308C>A | c.886G>T | p.A296S | MISSENSE | NASS | NASS | NASS |
| PMN | MLL | PMN 21 | CCDS31686.1 | 41 | 28 | 40.6% | g.chr11:117875226A>G | c.-1A>G | SpliceAcceptor | MISSENSE | 0.000 | 0.0000 | 0.00 |
| PMN | MNS1 | PMN 21 | CCDS10158.1 | 14 | 5 | 26.3% | g.chr15:54538015C>A | c.202G>T | p.E76X | NONSENSE | 0.790 | 0.3060 | 0.80 |
| PMN | PSG3 | PMN 21 | CCDS12611.1 | 130 | 70 | 35.0% | g.chr19:47929316G>A | c.842C>T | p.P281L | MISSENSE | 0.464 | 0.0240 | 0.30 |
| PMN | PTPRT | PMN 21 | CCDS42874.1 | 136 | 59 | 30.3% | g.chr20:40816533G>A | c.842C>T | p.A281V | MISSENSE | 0.874 | 0.0700 | 0.90 |
| PMN | RCH1 | PMN 21 | CCDS30940.1 | 101 | 58 | 36.5% | g.chr1:172197670C>T | c.2018G>A | p.R673H | MISSENSE | 0.838 | 0.4550 | 0.85 |
| PMN | RNF43 | PMN 21 | CCDS11607.1 | 115 | 81 | 41.9% | g.chr17:53786712C>T | c.305G>A | p.A169T | MISSENSE | 0.000 | 0.0000 | 0.00 |
| PMN | RNF43 | PMN 21 | CCDS11607.1 | 9 | 2 | 18.2% | g.chr17:53791025G>A | c.1111C>T | p.R371X | NONSENSE | 0.762 | 0.2400 | 0.75 |
| PMN | SIAH2 | PMN 21 | CCDS3152.1 | 20 | 10 | 33.3% | g.chr3:151963131C>T | c.176G>A | p.C59D | MISSENSE | 0.614 | 0.0760 | 0.45 |
| PMN | SIK3 | PMN 21 | CCDS8279.1 | 49 | 17 | 25.8% | g.chr11:116241106C>G | c.2955G>C | p.Q985H | MISSENSE | 0.808 | 0.7470 | 1.00 |
| PMN | SLC11A1 | PMN 21 | CCDS2415.1 | 22 | 9 | 29.0% | g.chr2:219618109C>G | c.682C>G | p.L228V | MISSENSE | 0.972 | 0.9290 | 1.00 |
| PMN | SLCO3A1 | PMN 21 | CCDS10671.1 | 100 | 28 | 21.9% | g.chr15:90607197G>A | c.1961G>A | p.R654H | MISSENSE | 0.920 | 0.7680 | 1.00 |
| PMN | TRPM7 | PMN 21 | CCDS42035.1 | 3 | 13 | 81.3% | g.chr15:40868211T>G | c.2439A>C | p.E813D | MISSENSE | 0.418 | 0.0190 | 0.25 |
| PMN | CDK13 | PMN 26 | CCDS5461.1 | 168 | 33 | 16.4% | g.chr7:40006361C>T | c.2602C>T | p.R868W | MISSENSE | 0.636 | 0.4550 | 0.85 |
| PMN | COX6C | PMN 26 | CCDS42630.1 | 5 | 4 | 44.4% | g.chr19:6057049G>T | c.210C>A | p.S70R | MISSENSE | NAS | NAS | NAS |
| PMN | FAM27A | PMN 26 | ENST00000377531 | 8 | 5 | 38.5% | g.chr9:43617239C>C | c.-1C>C | 5'-UTR | MISSENSE | 0.830 | 0.4280 | 0.85 |
| PMN | FAM27A | PMN 26 | ENST00000377531 | 15 | 4 | 21.1% | g.chr9:43617236C>G | c.17C>G | p.A6G | MISSENSE | 0.892 | 0.6810 | 0.95 |
| PMN | PHLDB1 | PMN 26 | CCDS9401.1 | 66 | 16 | 19.5% | g.chr11:118037736C>C | c.986G>C | p.G329A | MISSENSE | 0.760 | 0.2040 | 0.80 |
| PMN | VCX3A | PMN 26 | CCDS35199.1 | 45 | 14 | 23.7% | g.chrX:6462038A>G | c.311T>C | p.L104P | MISSENSE | 0.140* | 0.0010 | 0.05 |
| PMN | KRAS | PMN 26 | CCDS8703.1 | 308 | 146 | 32.2% | g.chr12:25289552C>G | c.34G>C | p.G12R | MISSENSE | 0.876 | 0.6140 | 0.90 |
| PMN | ADAMTS8 | PMN 36 | CCDS41732.1 | 117 | 58 | 33.1% | g.chr11:129786542G>A | c.1730C>T | p.T577M | MISSENSE | 0.544 | 0.0430 | 0.35 |
| PMN | ATP5J | PMN 36 | CCDS13574.1 | 25 | 13 | 34.2% | g.chr21:26023975A>G | c.2T>C | p.M1T | MISSENSE | 0.844 | 0.4810 | 0.90 |
| PMN | ATP7A | PMN 36 | CCDS35399.1 | 53 | 29 | 35.4% | g.chrX:77182869T>G | c.3801G>T | p.Q1267H | MISSENSE | 0.868 | 0.5810 | 0.90 |
| PMN | ATRX | PMN 36 | CCDS14434.1 | 100 | 39 | 28.1% | g.chrX:76626148G>A | c.1286C>T | p.A419V | MISSENSE | 0.862 | 0.5580 | 0.90 |
| PMN | C20orf185 | PMN 36 | CCDS13212.1 | 136 | 75 | 35.5% | g.chr20:61108943C>T | c.53C>T | p.A18V | MISSENSE | 0.888 | 0.6660 | 0.95 |
| PMN | CD93 | PMN 36 | CCDS13149.1 | 32 | 16 | 33.3% | g.chr20:23014586G>A | c.244C>T | p.R82W | MISSENSE | 0.882 | 0.6400 | 0.95 |
| PMN | CFB | PMN 36 | CCDS4729.1 | 77 | 32 | 41.2% | g.chr6:32026130A>T | c.1585A>T | p.D529V | MISSENSE | 0.832 | 0.2590 | 0.80 |
| PMN | CNOT2 | PMN 36 | CCDS8706.1 | 74 | 50 | 40.3% | g.chr12:69009487A>G | c.256A>G | p.M86V | MISSENSE | 0.770 | 0.4410 | 0.85 |
| PMN | CTR9 | PMN 36 | CCDS7805.1 | 34 | 16 | 32.0% | g.chr11:10734933A>C | c.564A>C | p.K188N | MISSENSE | 0.834 | 0.9630 | 1.00 |
| PMN | ESPNL | PMN 36 | CCDS2525.1 | 23 | 15 | 39.5% | g.chr2:239170488G>A | c.2795G>A | p.R932H | MISSENSE | 0.996 | 0.9630 | 1.00 |
| PMN | FAM155B | PMN 36 | CCDS6375.2 | 152 | 76 | 33.3% | g.chr6:139249380T | c.1198G>A | p.G400S | MISSENSE | 0.858 | 0.3410 | 0.90 |

FIG. 6 CONTINUED

| | | | | | | | | | |
|---|---|---|---|---|---|---|---|---|---|
| PMN | FBXO34 | PMN 36 | CCDS32086.1 | 57 | 28 | 32.9% | g.chr14:548885696G>T | c.1706G>T | p.E570X | NONSENSE | 0.000 | 0.0000 | 0.00 |
| PMN | FOXG1 | PMN 36 | CCDS9638.1 | 168 | 111 | 39.8% | g.chr14:28307783C>T | c.1127C>T | p.T376M | MISSENSE | 0.866 | 0.5700 | 0.90 |
| PMN | HCN4 | PMN 36 | CCDS10246.1 | 28 | 19 | 40.4% | g.chr15:74229946G>A | c.994C>T | p.R332W | MISSENSE | 0.920 | 0.7880 | 1.00 |
| PMN | IL6R | PMN 36 | CCDS1067.1 | 206 | 55 | 21.1% | g.chr1:152666390G>T | c.180G>T | p.W60C | MISSENSE | 0.640 | 0.0900 | 0.50 |
| PMN | KIF4A | PMN 36 | CCDS14401.1 | 40 | 13 | 24.5% | g.chrX:69511185C>T | c.1855C>T | p.Q619X | NONSENSE | 0.000 | 0.0000 | 0.00 |
| PMN | KTN1 | PMN 36 | CCDS41957.1 | 11 | 9 | 45.0% | g.chr14:55173637T>C | c.-11>C | SpliceDonor | | NASS | NASS | NASS |
| PMN | LAMA1 | PMN 36 | CCDS12787.1 | 56 | 35 | 38.8% | g.chr18:20321340C>A | c.9112G>T | p.G3038W | MISSENSE | 0.020 | 0.3970 | 0.95 |
| PMN | MCC | PMN 36 | CCDS43351.1 | 198 | 113 | 36.3% | g.chr5:112468756T>C | c.-1A>G | SpliceDonor | | NASS | NASS | NASS |
| PMN | NAV3 | PMN 36 | CCDS41815.1 | 47 | 19 | 28.8% | g.chr12:76282801>C | c.1601T>C | p.V534A | MISSENSE | 0.802 | 0.3420 | 0.80 |
| PMN | NOMO1 | PMN 36 | CCDS10656.1 | 73 | 43 | 37.1% | g.chr16:14682975G>A | c.2959G>A | p.D987N | MISSENSE | 0.840 | 0.4630 | 0.90 |
| PMN | NPHP3 | PMN 36 | CCDS3074.1 | 34 | 29 | 46.0% | g.chr3:132580080G>A | c.1474C>T | p.L492F | MISSENSE | 0.956 | 0.8690 | 1.00 |
| PMN | OBFC1 | PMN 36 | CCDS7552.1 | 77 | 40 | 34.2% | g.chr10:103647349A>C | c.700T>G | p.S234A | MISSENSE | 0.990 | 0.9750 | 1.00 |
| PMN | RFX2 | PMN 36 | CCDS12157.1 | 86 | 51 | 37.2% | g.chr19:5981173C>T | c.340G>A | p.G114S | MISSENSE | 0.070 | 0.5900 | 0.90 |
| PMN | RNF43 | PMN 36 | CCDS11607.1 | 35 | 80 | 69.9% | g.chr17:53794444G>T | c.647C>A | p.S216X | NONSENSE | 0.000 | 0.0000 | 0.00 |
| PMN | RYR1 | PMN 36 | CCDS33011.1 | 106 | 64 | 37.6% | g.chr19:43650179G>A | c.3286G>A | p.E1090K | MISSENSE | 0.846 | 0.4910 | 0.90 |
| PMN | SBF2 | PMN 36 | CCDS14427.1 | 19 | 19 | 50.0% | g.chr11:9767894C>T | c.5005G>A | p.V1669M | MISSENSE | 0.782 | 0.2890 | 0.80 |
| PMN | SCUBE2 | PMN 36 | CCDS7797.1 | 186 | 84 | 31.1% | g.chr11:9038596G>A | c.902C>T | p.S301L | MISSENSE | 0.098 | 0.1400 | 0.65 |
| PMN | SULF1 | PMN 36 | CCDS6204.1 | 50 | 22 | 30.6% | g.chr8:70679362C>T | c.1318C>T | p.R440W | MISSENSE | 0.834 | 0.4410 | 0.85 |
| PMN | TRMT2B | PMN 36 | CCDS14477.1 | 82 | 36 | 30.5% | g.chrX:100178698C>T | c.458G>A | p.R153Q | MISSENSE | 0.018 | 0.3910 | 0.85 |
| PMN | TRRAP | PMN 36 | CCDS5653.1 | 157 | 96 | 37.9% | g.chr7:98353032C>T | c.2446C>T | p.R816W | MISSENSE | 0.588 | 0.0530 | 0.40 |
| PMN | TTN | PMN 36 | NM_133379 | 49 | 21 | 30.0% | g.chr2:179347778C>T | c.1G>A | SpliceDonor | | NASS | NASS | NASS |
| PMN | UBR5 | PMN 36 | CCDS4863.1 | 44 | 26 | 37.1% | g.chr8:103370679A>G | c.4691T>C | p.I1564T | MISSENSE | 0.694 | 0.1350 | 0.65 |
| PMN | USP11 | PMN 36 | CCDS14277.1 | 134 | 56 | 29.5% | g.chrX:46932167G>T | c.2786C>T | p.R929L | MISSENSE | 0.662 | 0.1060 | 0.55 |
| PMN | VILL | PMN 36 | CCDS2670.2 | 119 | 41 | 25.5% | g.chr3:38013632A>T | c.511A>T | p.M171L | MISSENSE | 0.802 | 0.3420 | 0.80 |
| PMN | WIZ | PMN 36 | ENST00000389282 | 29 | 21 | 42.0% | g.chr19:15411901G>C | c.512C>G | p.A171G | MISSENSE | 0.086 | 0.6570 | 0.95 |
| PMN | WIZ | PMN 36 | ENST00000389282 | 26 | 11 | 29.7% | g.chr19:15411887G>A | c.1125C>T | p.A342V | MISSENSE | 0.044 | 0.4810 | 0.90 |
| PMN | ZAN | PMN 36 | ENST00000349350 | 276 | 177 | 39.1% | g.chr7:100172410G>A | c.172G>A | p.A58T | MISSENSE | 0.728 | 0.1830 | 0.65 |
| PMN | ZDHHC9 | PMN 36 | CCDS35385.1 | 69 | 38 | 35.5% | g.chrX:128785477C>G | c.340G>C | p.V116L | MISSENSE | 0.784 | 0.2940 | 0.80 |
| PMN | ZKSCAN3 | PMN 36 | CCDS4663.1 | 94 | 47 | 33.3% | g.chr6:28439108A>C | c.600A>C | p.K200N | MISSENSE | 0.096 | 0.7000 | 0.95 |
| PMN | ZNF831 | PMN 36 | CCDS42894.1 | 217 | 99 | 31.3% | g.chr20:57199920C>T | c.451C>T | p.R151C | MISSENSE | 0.912 | 0.7620 | 1.00 |

| | Gene | Sample | Accession | | | % | g.chr position | c. | p. | Type | | | |
|---|---|---|---|---|---|---|---|---|---|---|---|---|---|
| PMN | KRAS | PMN36 | CCDS8703.1 | 197 | 266 | 56.5% | g.chr12:25398282C>G | c.34G>C | p.G12R | MISSENSE | 0.140* | 0.0010 | 0.05 |
| PMN | ABCA13 | PMN4 | ENST00000319379 | 37 | 10 | 21.3% | g.chr7:48284496delTT | c.4522delTT | fs | DELETION | 0.000 | 0.0000 | 0.00 |
| PMN | ABCA13 | PMN4 | ENST00000319379 | 38 | 10 | 20.8% | g.chr7:48204498G>A | c.4524T>A | p.F1508L | MISSENSE | 0.776 | 0.2740 | 0.80 |
| PMN | APC | PMN4 | CCDS4107.1 | 85 | 34 | 28.6% | g.chr5:112203636C>T | c.4348C>T | p.R1450X | NONSENSE | 0.000 | 0.0000 | 0.00 |
| PMN | C8orf45 | PMN4 | CCDS6197.1 | 25 | 8 | 24.2% | g.chr8:67949212C>G | c.177C>G | p.H59Q | MISSENSE | 0.782 | 0.2890 | 0.80 |
| PMN | COX6A | PMN4 | CCDS10273.1 | 46 | 28 | 36.1% | g.chr15:73003115A>C | c.369T>G | p.L123R | MISSENSE | 0.800 | 0.3360 | 0.80 |
| PMN | DDX11 | PMN4 | CCDS8342.1 | 55 | 17 | 16.7% | g.chr11:108412396G>T | c.149G>T | p.R50L | MISSENSE | 0.822 | 0.4040 | 0.85 |
| PMN | DEPB104A | PMN4 | CCDS4834.1 | 20 | 4 | 16.7% | g.chr8:7731444A>G | c.20A>G | p.I10V | MISSENSE | 0.888 | 0.6680 | 0.95 |
| PMN | FAM163A | PMN4 | CCDS1335.1 | 291 | 59 | 16.9% | g.chr1:178049777A>T | c.334A>T | p.M112L | MISSENSE | 0.796 | 0.3240 | 0.80 |
| PMN | GNAS | PMN4 | CCDS13472.1 | 58 | 24 | 29.3% | g.chr20:56911781G>T | c.601C>T | p.R201C | MISSENSE | 0.668 | 0.1120 | 0.55 |
| PMN | KRT38 | PMN4 | CCDS11192.1 | 63 | 30 | 37.6% | g.chr7:3084999T>C | c.716A>G | p.K239R | MISSENSE | 0.870 | 0.5080 | 0.90 |
| PMN | LPAR4 | PMN4 | CCDS14441.1 | 23 | 78 | 77.2% | g.chrX:77897236A>G | c.214A>G | p.S72G | MISSENSE | 0.864 | 0.3610 | 0.90 |
| PMN | MRPS14 | PMN4 | CCDS1346.1 | 263 | 64 | 19.6% | g.chr1:173254411C>A | c.374G>T | p.R125L | MISSENSE | 0.694 | 0.1690 | 0.45 |
| PMN | MTAP | PMN4 | CCDS6609.1 | 92 | 43 | 31.9% | g.chr9:21849418C>A | c.807C>A | p.N269K | MISSENSE | 0.788 | 0.3020 | 0.60 |
| PMN | NALCN | PMN4 | CCDS9408.1 | 102 | 48 | 32.0% | g.chr13:100548650C>T | c.2863G>A | p.V955I | MISSENSE | 0.492 | 0.0310 | 0.30 |
| PMN | NRP2 | PMN4 | CCDS2364.1 | 39 | 14 | 26.4% | g.chr2:206365207A>G | c.2444A>G | p.D815G | MISSENSE | 0.972 | 0.9290 | 1.00 |
| PMN | OBFC1 | PMN4 | CCDS7652.1 | 86 | 39 | 30.6% | g.chr10:105648625 | c.581G>C | p.S194T | MISSENSE | 0.982 | 0.9620 | 1.00 |
| PMN | PCDH4 | PMN4 | CCDS4246.1 | 315 | 92 | 29.6% | g.chr5:141048391T>T | c.2153C>T | p.A718V | MISSENSE | 0.890 | 0.6730 | 0.95 |
| PMN | PLEKHH1 | PMN4 | ENST00000391163 | 91 | 37 | 28.9% | g.chr14:67078326G>A | c.106G>A | p.V36I | MISSENSE | NA** | NA** | NA** |
| PMN | PPPPR14B | PMN4 | CCDS31636 | 65 | 14 | 17.7% | g.chr11:63770820insG | c.359insC | fs | INSERTION | 0.000 | 0.0000 | 0.00 |
| PMN | PPP1R15B | PMN4 | CCDS1445.1 | 38 | 79 | 67.5% | g.chr1:202645589T>C | c.1604A>G | p.H535R | MISSENSE | 0.998 | 0.9980 | 1.00 |
| PMN | PRR11 | PMN4 | CCDS11614.1 | 103 | 42 | 29.0% | g.chr17:54627498G>A | c.767G>A | p.R256Q | MISSENSE | 0.924 | 0.7990 | 1.00 |
| PMN | FUS7 | PMN4 | CCDS34725.1 | 258 | 102 | 33.8% | g.chr17:33630396A>G | c.1972A>G | p.T658A | MISSENSE | 0.834 | 0.4410 | 0.85 |
| PMN | TBC1D3F | PMN4 | ENST00000327454 | 10 | 4 | 28.6% | g.chr17:36415866G>A | c.471A>G | p.I157M | MISSENSE | 0.954 | 0.8840 | 1.00 |
| PMN | TLL7 | PMN4 | CCDS8930.2 | 39 | 11 | 22.0% | g.chr2:98445886G>A | c.1576C>T | SpliceAcceptor | NONSENSE | 0.000 | 0.0000 | 0.00 |
| PMN | APL | PMN41 | CCDS217.1 | 70 | 10 | 12.5% | g.chr1:21772744G>C | c.-1G>C | p.R262V | MISSENSE | NASS | NASS | NASS |
| PMN | ASTN2 | PMN41 | CCDS6515.1 | 62 | 12 | 16.2% | g.chr9:118841961C>T | c.1228G>A | p.V410M | MISSENSE | 0.730 | 0.1670 | 0.65 |
| PMN | BFSP2 | PMN41 | CCDS3059.1 | 112 | 26 | 18.8% | g.chr3:134519980C>T | c.859C>T | p.R287W | MISSENSE | 0.946 | 0.4910 | 0.90 |
| PMN | CACNA1I | PMN41 | NM_021096 | 57 | 7 | 10.9% | g.chr22:38304920C>T | c.2183C>T | p.S728L | MISSENSE | 0.814 | 0.3790 | 0.85 |
| PMN | CLIP2 | PMN41 | CCDS5568.1 | 378 | 46 | 11.3% | g.chr6:7346017C>T | c.706C>T | p.R236W | MISSENSE | 0.946 | 0.8640 | 1.00 |
| PMN | CPNE5 | PMN41 | CCDS4826.1 | 129 | 32 | 19.9% | g.chr6:36818111G>A | c.1094C>T | p.P365L | MISSENSE | 0.760 | 0.2840 | 0.80 |

| | | | | | | | | | | | |
|---|---|---|---|---|---|---|---|---|---|---|---|
| PMN | CRIPAK | PMN 41 | CCDS3349.1 | 33 | 5 | 13.2% | g.chr4:1379724C>G | c.425C>G | p.P142R | MISSENSE | 0.858 | 0.5410 | 0.90 |
| PMN | DHX58 | PMN 41 | CCDS11416.1 | 76 | 36 | 32.1% | g.chr17:37514658G>A | c.634C>T | p.Q212X | NONSENSE | 0.000 | 0.0000 | 0.00 |
| PMN | EML4 | PMN 41 | CCDS1807.1 | 40 | 13 | 24.5% | g.chr2:42396862C>T | c.2044C>T | p.R682C | MISSENSE | 0.656 | 0.1030 | 0.55 |
| PMN | FGD1 | PMN 41 | CCDS14339.1 | 30 | 6 | 16.7% | g.chrX:54513172A>T | c.-1T>A | SpliceDonor | | NASS | NASS | NASS |
| PMN | FNBP4 | PMN 41 | CCDS41644.1 | 23 | 45 | 39.6% | g.chr11:47722198G>A | c.1339C>T | p.R447C | MISSENSE | 0.982 | 0.3520 | 1.00 |
| PMN | HDAC4 | PMN 41 | CCDS2529.1 | 59 | 51 | 46.4% | g.chr2:239855175T>C | c.2611A>G | p.D904G | MISSENSE | 0.632 | 0.0630 | 0.50 |
| PMN | HLA-DRB5 | PMN 41 | CCDS4751.1 | 11 | 5 | 31.3% | g.chr6:32597764T>G | c.266A>C | p.Y89S | MISSENSE | 0.298 | 0.0070 | 0.15 |
| PMN | IQCA1L | PMN 41 | ENST00000340262 | 43 | 6 | 12.2% | g.chr2:150520537C>T | c.2086G>A | p.R696Q | MISSENSE | NA** | NA** | NA** |
| PMN | TH5 | PMN 41 | CCDS31159.1 | 141 | 102 | 42.0% | g.chr1:77926163>A | c.634C>T | p.A156V | MISSENSE | 0.670 | 0.1140 | 0.55 |
| PMN | KCNB1 | PMN 41 | CCDS13418.1 | 52 | 17 | 24.6% | g.chr20:47422411C>T | c.2093C>A | p.R698Q | NONSENSE | 0.980 | 0.9470 | 1.00 |
| PMN | KCNQ3 | PMN 41 | CCDS34943.1 | 143 | 120 | 45.6% | g.chr8:133254064G>A | c.1083G>T | p.E361D | MISSENSE | 0.710 | 0.1550 | 0.65 |
| PMN | KIAA0467 | PMN 41 | CCDS3694.1 | 63 | 7 | 10.0% | g.chr1:43660274>G | c.1452C>G | p.I484M | MISSENSE | 0.804 | 0.3470 | 0.80 |
| PMN | KIAA0467 | PMN 41 | CCDS36694.1 | 52 | 7 | 11.9% | g.chr11:43666674C>T | c.1466C>T | p.S489F | MISSENSE | 0.792 | 0.3130 | 0.80 |
| PMN | KLC4 | PMN 41 | CCDS4862.1 | 120 | 25 | 17.2% | g.chr6:43142729A>G | c.863A>G | p.K288R | MISSENSE | 0.874 | 0.1170 | 0.55 |
| PMN | MSC | PMN 41 | CCDS45746.1 | 161 | 30 | 15.7% | g.chr8:72918609C>T | c.362C>A | p.R121H | MISSENSE | 0.858 | 0.9410 | 0.90 |
| PMN | NBPF16 | PMN 41 | CCDS41384.1 | 4 | 4 | 50.0% | g.chr1:147023742C>T | c.1847C>G | p.S616L | MISSENSE | 0.862 | 0.5560 | 0.90 |
| PMN | NCAN | PMN 41 | CCDS12397.1 | 126 | 14 | 10.0% | g.chr19:19221613C>A | c.3861C>A | p.H1287Q | MISSENSE | 0.796 | 0.3000 | 0.80 |
| PMN | PDE7A | PMN 41 | CCDS43743.1 | 46 | 42 | 47.7% | g.chr8:96916880C>A | c.1110G>T | p.G37V | MISSENSE | 0.856 | 0.5200 | 0.85 |
| PMN | PJA2R1 | PMN 41 | CCDS33309.1 | 12 | 4 | 25.0% | g.chr2:161627121C>G | c.40G>C | p.G14R | MISSENSE | 0.906 | 0.7400 | 1.00 |
| PMN | PLCL1 | PMN 41 | CCDS2326.1 | 27 | 5 | 15.6% | g.chr2:198659138G>A | c.2336G>A | p.D789N | MISSENSE | 0.602 | 0.0670 | 0.45 |
| PMN | POLE | PMN 41 | CCDS9278.1 | 45 | 5 | 10.0% | g.chr12:133771908T>G | c.6236A>C | p.N2079T | MISSENSE | 0.890 | 0.6730 | 0.95 |
| PMN | PROKR2 | PMN 41 | CCDS19089.1 | 94 | 27 | 22.3% | g.chr20:5294287C>T | c.229C>A | p.A77T | MISSENSE | 0.860 | 0.9470 | 0.90 |
| PMN | RNF43 | PMN 41 | CCDS11617.1 | 73 | 17 | 18.9% | g.chr17:53803309G>A | c.397C>T | p.R113X | NONSENSE | 0.000 | 0.0000 | 0.00 |
| PMN | RPN2 | PMN 41 | CCDS12591.1 | 58 | 33 | 36.3% | g.chr20:35246087A>G | c.104A>G | p.E35G | MISSENSE | 0.706 | 0.4990 | 0.65 |
| PMN | ST14 | PMN 41 | CCDS8487.1 | 68 | 30 | 30.6% | g.chr11:128063277G>T | c.190C>T | p.G64C | MISSENSE | 0.720 | 0.1710 | 0.65 |
| PMN | TEKT3 | PMN 41 | CCDS11169.1 | 46 | 35 | 43.2% | g.chr17:15168243T>C | c.764A>G | p.E255G | MISSENSE | 0.472 | 0.0270 | 0.30 |
| PMN | TP53BP1 | PMN 41 | CCDS10036.1 | 75 | 88 | 54.0% | g.chr15:41499916A>C | c.4545T>G | p.Y1515X | NONSENSE | 0.000 | 0.0000 | 0.00 |
| PMN | TRPV2 | PMN 41 | CCDS2576.1 | 112 | 57 | 33.7% | g.chr17:16280636G>A | c.2203G>A | p.E735K | MISSENSE | 0.858 | 0.9410 | 0.90 |
| PMN | VPS39 | PMN 41 | CCDS10083.1 | 61 | 7 | 10.3% | g.chr2:167810677C>T | c.-1G>T | SpliceDonor | | NASS | NASS | NASS |
| PMN | XIRP2 | PMN 41 | CCDS42763.1 | 17 | 13 | 43.3% | g.chr2:167810677C>T | c.4489C>T | p.R1497X | NONSENSE | 0.000 | 0.0000 | 0.00 |

FIG. 6 CONTINUED

| PMN | ZNF470 | PMN 41 | CCDS33122.1 | 42 | 12 | 22.2% | g.chr19.61781355A>C | c.1746A>C | p.Q582H | MISSENSE | 0.894 | 0.6910 | 0.95 |
| PMN | ZNF470 | PMN 41 | CCDS33122.1 | 36 | 10 | 21.7% | g.chr19.61780763G>A | c.1154G>A | p.R385H | MISSENSE | 0.952 | 0.8800 | 1.00 |

FIG. 6
CONTINUED

| | | | | | | | | | | |
|---|---|---|---|---|---|---|---|---|---|---|
| MCN | CEL | MCN 158 | CCDS43696.1 | 58 | 13 | 18.3% | g.chr9:13492415>T | c.-1>T | SpliceDonor | NASS | NASS | 0.65 |
| MCN | CCB8 | MCN 158 | CCDS12753.1 | 11 | 4 | 26.1% | g.chr19:54248212T>G | c.410A>C | p.D137A | 0.714 | 0.1610 | 0.90 |
| MCN | GOLGA2 | MCN 158 | CCDS6396.1 | 21 | 5 | 19.2% | g.chr9:130606396C>A | c.2091G>T | p.E697D | 0.850 | 0.5080 | 0.90 |
| MCN | HLA-C | MCN 158 | ENST00000376235 | 18 | 4 | 18.2% | g.chr6:31463102A>G | c.-1>C | SpliceAcceptor | NASS | NASS | NASS |
| MCN | ICAM4 | MCN 158 | CCDS32904.1 | 53 | 39 | 42.4% | g.chr19:10269313G>T | c.419G>T | p.G140V | 0.992 | 0.9620 | 1.00 |
| MCN | MCCC1 | MCN 158 | CCDS3241.1 | 65 | 46 | 41.4% | g.chr3:184227719T>C | c.1496A>G | p.S499G | 0.820 | 0.3970 | 0.85 |
| MCN | POTEJ | MCN 158 | ENST00000409602 | 94 | 16 | 14.4% | g.chr2:131086501G>A | c.86G>A | p.R29H | 0.956 | 0.8890 | 1.00 |
| MCN | POTEJ | MCN 158 | ENST00000409602 | 98 | 16 | 14.0% | g.chr2:131086531T>A | c.561>A | p.V19D | 0.992 | 0.9820 | 1.00 |
| MCN | VCAN | MCN 158 | CCDS4060.1 | 60 | 46 | 43.4% | g.chr5:82670436C>T | c.3556C>T | p.T1353M | 0.902 | 0.7240 | 1.00 |
| MCN | AKAP8 | MCN 158 | CCDS9644.1 | 159 | 76 | 32.3% | g.chr14:91972636A>G | c.246A>G | p.E82G | 0.678 | 0.1210 | 0.60 |
| MCN | BBS9 | MCN 162 | CCDS43566.1 | 8 | 9 | 52.9% | g.chr7:33384043G>A | c.1604G>A | p.C535Y | 0.632 | 0.4350 | 0.85 |
| MCN | CO_4A3 | MCN 162 | CCDS42629.1 | 50 | 16 | 24.2% | g.chr2:227821454G>A | c.520G>A | p.G174R | 0.826 | 0.4170 | 0.65 |
| MCN | CO_5A1 | MCN 162 | CCDS6932.1 | 105 | 46 | 30.5% | g.chr9:1368168680>T | c.2498C>T | p.P833L | 0.800 | 0.3360 | 0.90 |
| MCN | FAM21A | MCN 162 | CCDS41527.1 | 18 | 4 | 18.2% | g.chr10:51523686A>G | c.-1A>G | SpliceDonor | NASS | NASS | NASS |
| MCN | FRG1B | MCN 162 | ENST00000278882 | 17 | 4 | 19.0% | g.chr20:28245229A>G | c.364A>G | p.K122E | 0.894 | 0.6910 | 0.95 |
| MCN | KRAS | MCN 162 | CCDS8703.1 | 7 | 3 | 30.0% | g.chr12:25288510>A | c.35G>T | p.G12V | 0.346* | 0.0100 | 0.15 |
| MCN | MTHFD1 | MCN 162 | CCDS9763.1 | 41 | 34 | 45.3% | g.chr14:63994742C>T | c.2776C>T | p.P926S | 0.544 | 0.0430 | 0.35 |
| MCN | R3HDM1 | MCN 162 | CCDS2177.1 | 36 | 9 | 20.0% | g.chr2:136183529delCT | c.2405delCT | fs | DELETION | 0.000 | 0.0000 | 0.00 |
| MCN | SDHAP1 | MCN 162 | ENST00000354937 | 16 | 6 | 27.3% | g.chr3:197197074T>C | c.-1A>G | SpliceAcceptor | NASS | NASS | NASS |
| MCN | SFN6T2 | MCN 162 | CCDS31138.1 | 76 | 30 | 28.3% | g.chr10:72546540>A | c.2071C>T | p.R691W | 0.874 | 0.6070 | 0.90 |
| MCN | SLC5A2 | MCN 162 | CCDS10714.1 | 251 | 105 | 29.5% | g.chr16:31408534T>A | c.212T>A | p.L71H | 0.540 | 0.0410 | 0.35 |
| MCN | TEX2 | MCN 162 | CCDS11658.1 | 163 | 127 | 43.8% | g.chr17:59619339C>T | c.2266G>A | p.R756K | 0.922 | 0.7940 | 1.00 |
| MCN | ZUFSP | MCN 162 | CCDS5110.1 | 21 | 7 | 25.0% | g.chr6:117094631>G | c.1261A>C | p.K421Q | 0.900 | 0.7160 | 1.00 |
| MCN | C22orf34 | MCN 162 | ENST00000405354 | 125 | 36 | 22.0% | g.chr22:48404462C>A | c.3030>T | p.R101S | 0.986 | 0.9630 | 1.00 |
| MCN | C22orf43 | MCN 163 | CCDS42965.1 | 39 | 10 | 20.4% | g.chr22:22294263delCAT | c.4626delATG | fs | DELETION | 0.000 | 0.0000 | 0.00 |
| MCN | DAB2IP | MCN 163 | CCDS6633.2 | 70 | 32 | 31.4% | g.chr9:126582626C>T | c.1073C>T | p.T358M | 0.722 | 0.1730 | 0.65 |
| MCN | FCGBP | MCN 163 | CCDS12546.1 | 20 | 4 | 16.7% | g.chr19:45304122T>G | c.8204A>C | p.Q273SP | 0.784 | 0.2940 | 0.80 |
| MCN | GTF3C5 | MCN 163 | CCDS6958.1 | 237 | 100 | 29.7% | g.chr9:134921030>T | c.1382C>T | p.S461F | 0.768 | 0.3020 | 0.80 |
| MCN | KRAS | MCN 163 | CCDS8703.1 | 10 | 3 | 23.1% | g.chr12:25288480>T | c.38C>A | p.G13D | 0.098* | 0.0010 | 0.05 |
| MCN | OR2T5 | MCN 163 | CCDS31118.1 | 28 | 6 | 17.6% | g.chr1:248718634A>T | c.122A>T | p.K41M | 0.710 | 0.1550 | 0.65 |

| | Gene | Accession | | | % | Chr Position | c. | p. | Type | | | |
|---|---|---|---|---|---|---|---|---|---|---|---|---|
| MCN | KRAS | CCD38703.1 | 3 | 3 | 50.0% | g.chr12:25289551C>T | c.35G>A | p.G12D | MISSENSE | 0.132* | 0.0010 | 0.05 |
| MCN | LRRC7 | ENST00000370958 | 48 | 30 | 38.5% | g.chr1:70501674A>T | c.92A>T | p.E31V | MISSENSE | 0.662 | 0.5560 | 0.90 |
| MCN | MAGEE2 | CCDS14431.1 | 62 | 20 | 24.4% | g.chrX:74921236G>A | c.314C>T | p.T105M | MISSENSE | 0.996 | 0.9950 | 1.00 |
| MCN | MON2 | CCDS31949.1 | 22 | 4 | 15.4% | g.chr12:108988A>T | c.-1A>T | Splice Acceptor | | NASS | NASS | NASS |
| MCN | MUC4 | NM_018406 | 60 | 10 | 14.3% | g.chr3:19598843G>A | c.4394C>T | p.A1465V | MISSENSE | 0.980 | 0.9470 | 1.00 |
| MCN | QDZ1 | CCDS14609.1 | 107 | 66 | 38.2% | g.chrX:125993688C>T | c.1970G>A | p.E624K | MISSENSE | 0.816 | 0.3910 | 0.85 |
| MCN | OR2A5 | CCDS43689.1 | 31 | 24 | 43.6% | g.chr7:143426110>A | c.566C>A | p.A163E | MISSENSE | 0.670 | 0.5500 | 0.90 |
| MCN | OR7B | CCDS31100.1 | 42 | 7 | 14.3% | g.chr4:246451053T>G | c.1211T>G | p.S414A | MISSENSE | 0.845 | 0.4990 | 0.90 |
| MCN | PCSK5 | CCDS6052.1 | 19 | 23 | 54.8% | g.chr9:77025605G>T | c.518G>T | p.G173V | MISSENSE | 0.486 | 0.0000 | 0.30 |
| MCN | PRAMEF11 | NM_001146344 | 28 | 9 | 24.3% | g.chr1:12810994C>T | c.127G>A | p.D43N | MISSENSE | 0.738 | 0.2230 | 0.75 |
| MCN | PRAMEF11 | NM_001146344 | 24 | 4 | 14.3% | g.chr1:12810951T>G | c.153A>C | p.D51H | MISSENSE | 0.714 | 0.1610 | 0.65 |
| MCN | RNF43 | CCDS11607.1 | 11 | 4 | 26.7% | g.chr17:53791023G>A | c.1111C>T | p.R371X | NONSENSE | 0.000 | 0.0000 | 0.00 |
| MCN | S1PR3 | CCDS9680.1 | 98 | 77 | 44.0% | g.chr9:90804963C>T | c.22C>T | p.Q10X | NONSENSE | 0.000 | 0.100 | 0.00 |
| MCN | SIDT1 | CCDS9874.1 | 111 | 90 | 44.8% | g.chr3:114749217T>C | c.485T>C | p.L162P | MISSENSE | 0.862 | 0.5560 | 0.90 |
| MCN | SLC4A1 | CCDS34418.1 | 190 | 143 | 42.9% | g.chr6:107455503G>A | c.284G>A | p.R95H | MISSENSE | 0.928 | 0.8110 | 1.00 |
| MCN | TSPAN15 | CCDS7294.1 | 28 | 22 | 44.0% | g.chr10:70934210A>G | c.589A>G | p.M197V | MISSENSE | 0.770 | 0.2590 | 0.80 |
| MCN | UNC95I | ENST00000227471 | 28 | 4 | 14.3% | g.chr1:75168050G>A | c.1579G>T | p.R527C | MISSENSE | 0.038 | 0.4550 | 0.85 |
| MCN | VPS13B | CCDS6280.1 | 12 | 8 | 40.0% | g.chr8:100202622C>T | c.979C>T | p.Q327A | MISSENSE | 0.000 | 0.0030 | 0.00 |
| MCN | WNT3A | CCDS1584.1 | 60 | 44 | 42.3% | g.chr1:226305177G>A | c.511G>A | p.D171N | MISSENSE | 0.618 | 0.0780 | 0.45 |
| MCN | ZBTB20 | CCDS2981.1 | 81 | 71 | 46.7% | g.chr3:115552591T>C | c.657A>G | p.D226G | MISSENSE | 0.556 | 0.1470 | 0.35 |
| MCN | ABCA1 | CCDS6762.1 | 110 | 31 | 22.0% | g.chr9:106631540C>T | c.1763G>A | p.V589I | MISSENSE | 0.988 | 0.8950 | 1.00 |
| MCN | ANGPTL6 | CCDS12224.1 | 138 | 35 | 20.2% | g.chr19:10065753T>C | c.947A>G | p.Y316C | MISSENSE | 0.530 | 0.0039 | 0.35 |
| MCN | ARHGAP30 | CCDS30918.1 | 51 | 16 | 23.9% | g.chr1:159289713G>A | c.742C>T | p.P248S | MISSENSE | 0.698 | 0.1400 | 0.65 |
| MCN | C14orf135 | NM_022496 | 19 | 4 | 17.4% | g.chr4:59627168A>T | c.-1A>T | Splice Acceptor | | NASS | NASS | NASS |
| MCN | CDC27 | CCDS11509.1 | 14 | 6 | 30.0% | g.chr17:42568548A>G | c.1912T>C | p.W638R | MISSENSE | 0.170 | 0.0020 | 0.05 |
| MCN | CHST9 | CCDS42422.1 | 60 | 18 | 23.1% | g.chr18:22780898C>A | c.834G>T | p.R265I | MISSENSE | 0.336 | 0.0100 | 0.15 |
| MCN | EPHX3 | CCDS12327.1 | 60 | 22 | 26.8% | g.chr19:15190286G>C | c.1062C>G | p.F354L | MISSENSE | 0.706 | 0.1490 | 0.65 |
| MCN | HAVCR1 | CCDS43921.1 | 67 | 16 | 19.3% | g.chr5:156414942C>T | c.227G>A | p.R76H | MISSENSE | 0.942 | 0.4740 | 0.90 |
| MCN | HECW1 | CCDS54689.2 | 256 | 69 | 21.2% | g.chr7:43268949G>A | c.2215G>A | p.R1072Q | MISSENSE | 0.872 | 0.6000 | 0.90 |
| MCN | ITFG1 | CCDS10720.1 | 61 | 12 | 16.4% | g.chr16:45747136T>C | c.1834A>G | p.M612V | MISSENSE | 0.784 | 0.2340 | 0.80 |

FIG. 6 CONTINUED

| | | | | | | | | | | |
|---|---|---|---|---|---|---|---|---|---|---|
| MCN | KRAS | MCN 168 | CCDS8703.1 | 12 | 18 | 60.0% | g.chr12:25289551C>A | c.35G>T | p.G12V | MISSENSE | 0.946* | 0.0100 | 0.15 |
| MCN | OR4L1 | MCN 168 | CCDS32223.1 | 57 | 10 | 14.9% | g.chr14:19598798G>T | c.755G>T | p.G252V | MISSENSE | 0.816 | 0.3850 | 0.85 |
| MCN | OR2N2 | MCN 168 | CCDS11399.1 | 70 | 17 | 19.5% | g.chr11:5790933G>A | c.794G>A | p.R265H | MISSENSE | 0.928 | 0.8110 | 1.00 |
| MCN | PCDHA4 | MCN 168 | CCDS4249.1 | 273 | 50 | 15.5% | g.chr5:141166208G>A | c.1252G>A | p.V418M | MISSENSE | 0.904 | 0.7530 | 1.00 |
| MCN | PER1 | MCN 168 | CCDS11131.1 | 29 | 11 | 27.5% | g.chr17:7988400C>T | c.3355C>A | p.D1119A | MISSENSE | 0.910 | 0.7160 | 1.00 |
| MCN | PM20D1 | MCN 168 | CCDS1460.1 | 102 | 26 | 20.3% | g.chr1:204081192G>T | c.373C>A | p.H125N | MISSENSE | 0.302 | 0.0070 | 0.15 |
| MCN | PPP4C | MCN 168 | CCDS10669.1 | 133 | 24 | 15.3% | g.chr16:30003485G>T | c.-1C>T | SpliceAcceptor | MISSENSE | NASS | NASS | NASS |
| MCN | RGPD4 | MCN 168 | NM_182538 | 14 | 5 | 26.3% | g.chr2:107845864G>A | c.2413G>A | p.A805T | MISSENSE | 0.796 | 0.3240 | 0.80 |
| MCN | RNF43 | MCN 168 | CCDS11607.1 | 99 | 38 | 27.7% | g.chr17:57793556C>G | c.380G>C | p.R127P | MISSENSE | 0.764 | 0.2440 | 0.75 |
| MCN | ST6GALNAC5 | MCN 168 | CCDS873.1 | 13 | 6 | 31.6% | g.chr1:77406696C>T | c.114G>T | p.Q38H | MISSENSE | 0.756 | 0.2300 | 0.75 |
| MCN | SYTL3 | MCN 168 | CCDS4563.1 | 31 | 6 | 16.2% | g.chr6:159010465C>T | c.161C>T | p.T54M | MISSENSE | 0.808 | 0.3610 | 0.85 |
| MCN | TIMM23 | MCN 168 | CCDS7238.1 | 17 | 6 | 26.1% | g.chr10:51290367G>C | c.128C>G | p.S43C | MISSENSE | 0.713 | 0.1670 | 0.65 |
| MCN | TP53 | MCN 168 | CCDS11118.1 | 51 | 14 | 21.5% | g.chr17:7518293C>G | c.713G>C | p.C238S | MISSENSE | 0.000* | 0.0000 | 0.05 |
| MCN | TLL5 | MCN 168 | CCDS3124.1 | 28 | 6 | 17.6% | g.chr14:752700833A>T | c.-1A>T | SpliceAcceptor | MISSENSE | NASS | NASS | NASS |
| MCN | USP2 | MCN 168 | CCDS2697.1 | 17 | 4 | 19.0% | g.chr17:55645242G>A | c.2803C>T | p.R935W | MISSENSE | 0.546 | 0.0440 | 0.35 |
| MCN | AK5 | MCN 169 | ENST00000370807 | 183 | 49 | 21.1% | g.chr17:7552150G>A | c.782G>A | p.R261H | MISSENSE | 0.988 | 0.9860 | 1.00 |
| MCN | C6orf58 | MCN 169 | CCDS4593.1 | 18 | 5 | 21.7% | g.chr6:127362923A>T | c.-1A>T | SpliceAcceptor | MISSENSE | NASS | NASS | NASS |
| MCN | MLC4 | MCN 169 | NM_018406 | 76 | 35 | 31.5% | g.chr3:186989919G>C | c.3927C>G | p.H1309Q | MISSENSE | 0.978 | 0.9420 | 1.00 |
| MCN | OTUD5 | MCN 169 | CCDS14313.1 | 23 | 6 | 20.7% | g.chrX:48665636C>T | c.1510C>T | p.D504N | MISSENSE | 0.884 | 0.6490 | 0.95 |
| MCN | PLEKHB2 | MCN 169 | ENST00000404460 | 7 | 7 | 50.0% | g.chr2:131927298G>T | c.659G>T | p.R220M | MISSENSE | 0.980 | 0.9470 | 1.00 |
| MCN | RYR1 | MCN 169 | CCDS33011.1 | 29 | 17 | 37.0% | g.chr19:43623030G>T | c.130C>T | p.R44C | MISSENSE | 0.884 | 0.6490 | 0.95 |
| MCN | SPAG1 | MCN 169 | CCDS34930.1 | 81 | 24 | 22.9% | g.chr8:101306619G>A | c.1803G>A | p.M601I | MISSENSE | 0.846 | 0.4900 | 0.90 |
| MCN | TDRD9 | MCN 169 | CCDS9987.1 | 10 | 4 | 28.6% | g.chr14:103554213A>T | c.1508A>T | p.Y503F | MISSENSE | 0.804 | 0.3470 | 0.80 |
| MCN | THSD7B | MCN 170 | CCDS11118.1 | 112 | 32 | 22.2% | g.chr2:139130684C>A | c.4163C>A | p.T1388N | MISSENSE | 0.860 | 0.5470 | 0.90 |
| MCN | TP53 | MCN 170 | NM_001039063 | 51 | 22 | 30.1% | g.chr17:7519174C>T | c.48G>A | p.A16T | MISSENSE | 0.000* | 0.0000 | 0.05 |
| MCN | ARL17A | MCN 170 | NM_001039063 | 10 | 8 | 44.4% | g.chr17:41706010G>C | c.191C>G | p.A64G | MISSENSE | 0.878 | 0.6220 | 0.90 |
| MCN | ARL17B | MCN 170 | CCDS13328.1 | 10 | 8 | 44.4% | g.chr17:41706010G>C | c.191C>G | p.A64G | MISSENSE | 0.878 | 0.6220 | 0.90 |
| MCN | GDAP1L1 | MCN 170 | CCDS8703.1 | 407 | 294 | 41.9% | g.chr20:42425282A>C | c.-1A>C | SpliceAcceptor | MISSENSE | NASS | NASS | NASS |
| MCN | KRAS | MCN 170 | ENST00000354998 | 10 | 4 | 28.6% | g.chr12:25289551C>A | c.35G>T | p.G12V | MISSENSE | 0.946* | 0.0100 | 0.15 |
| MCN | MST1P9 | MCN 170 | | 9 | 6 | 40.0% | g.chr1:16959357C>G | c.649C>G | p.E217Q | MISSENSE | NA** | NA** | NA** |
| MCN | NRP1 | MCN 170 | CCDS7177.1 | 18 | 8 | 30.8% | g.chr10:33599390G>A | c.349G>T | p.P117S | MISSENSE | 0.976 | 0.9360 | 1.00 |

FIG. 6 CONTINUED

| | | | | | | | | | | |
|---|---|---|---|---|---|---|---|---|---|---|
| MCN | POTEE | MCN 170 | NM_001083538 | 77 | 26 | 25.2% | g.chr2:131727069T>A | c.1705T>A | p.L569I | MISSENSE | 0.652 | 0.1000 | 0.55 |
| MCN | POTEJ | MCN 170 | ENST00000409602 | 150 | 37 | 19.8% | g.chr2:131085666T>C | c.91T>C | p.C31R | MISSENSE | 0.976 | 0.9360 | 1.00 |
| MCN | POTEJ | MCN 170 | ENST00000409602 | 169 | 49 | 22.5% | g.chr2:131086661G>A | c.86G>A | p.R29H | MISSENSE | 0.956 | 0.8890 | 1.00 |
| MCN | PRB2 | MCN 170 | CCDS41757.1 | 240 | 66 | 21.6% | g.chr12:11437476G>T | c.740C>A | p.P247Q | MISSENSE | 0.852 | 0.5170 | 0.90 |
| MCN | RNF43 | MCN 170 | CCDS11607.1 | 180 | 14 | 7.2% | g.chr17:56347816G>C | c.122C>G | p.S41X | NONSENSE | 0.000 | 0.0000 | 0.00 |
| MCN | SCAMP2 | MCN 170 | CCDS10271.1 | 133 | 120 | 47.4% | g.chr15:72930821A>C | c.398T>G | p.F133C | MISSENSE | 0.716 | 0.1640 | 0.65 |
| MCN | ZNF277 | MCN 170 | CCDS5755.2 | 73 | 36 | 33.0% | g.chr7:111634033C>T | c.26C>T | p.A9V | MISSENSE | 0.828 | 0.4220 | 0.85 |

FIG. 6
CONTINUED

| | | | CCDS | | | | | | | |
|---|---|---|---|---|---|---|---|---|---|---|
| SPN | ANKRD30A | SPN 12 | CCDS7193.1 | 28 | 12 | 30.0% | g.chr10:37547954A>G | c.3140A>G | p.E1047G | MISSENSE | 0.990 | 0.9960 | 1.00 |
| SPN | CTNNB1 | SPN 12 | CCDS2694.1 | 25 | 25 | 50.0% | g.chr3:41241108G>T | c.101G>T | p.G34V | MISSENSE | 0.033* | 0.0000 | 0.05 |
| SPN | TRIP11 | SPN 12 | CCDS9899.1 | 28 | 14 | 33.3% | g.chr14:91575769A>C | c.14T>G | p.L5R | MISSENSE | 0.668 | 0.5840 | 0.90 |
| SPN | CTNNB1 | SPN 17 | CCDS2694.1 | 18 | 26 | 59.1% | g.chr3:41241107G>A | c.10G>A | p.G4R | MISSENSE | 0.036* | 0.0000 | 0.05 |
| SPN | CTNNB1 | SPN 19 | CCDS2694.1 | 57 | 36 | 38.7% | g.chr3:41241101G>A | c.94G>A | p.D32N | MISSENSE | 0.030* | 0.0000 | 0.05 |
| SPN | KIAA1632 | SPN 19 | CCDS11926.2 | 84 | 39 | 31.7% | g.chr8:41777724G>A | c.1844G>T | p.A615V | MISSENSE | 0.942 | 0.3540 | 1.00 |
| SPN | CTNNB1 | SPN 2 | CCDS2694.1 | 22 | 18 | 45.0% | g.chr3:41241107G>A | c.10G>A | p.G4R | MISSENSE | 0.036* | 0.0000 | 0.05 |
| SPN | NLGN3 | SPN 2 | CCDS14407.1 | 28 | 16 | 36.4% | g.chrX:70306292G>A | c.2107G>A | p.V703I | MISSENSE | 0.950 | 0.8180 | 1.00 |
| SPN | APPBP2 | SPN 2 | CCDS32699.1 | 32 | 9 | 22.0% | g.chr17:55939291C>A | c.355C>T | p.Q319X | NONSENSE | 0.000 | 0.0000 | 0.00 |
| SPN | CCDC8 | SPN 4 | CCDS12835.1 | 80 | 24 | 23.1% | g.chr19:51006461C>T | c.1447C>A | p.P483T | MISSENSE | 0.848 | 0.4980 | 0.90 |
| SPN | CTNNB1 | SPN 4 | CCDS2694.1 | 22 | 24 | 52.2% | g.chr3:41241165C>G | c.98C>G | p.S33C | MISSENSE | 0.012* | 0.0000 | 0.05 |
| SPN | LRP5 | SPN 4 | CCDS9876.1 | 126 | 37 | 22.7% | g.chr11:14426336G>A | c.758G>A | p.R253H | MISSENSE | 0.784 | 0.2940 | 0.80 |
| SPN | NIPBL | SPN 4 | CCDS32201 | 75 | 23 | 23.5% | g.chr5:37012983G>T | c.1317G>T | p.Q439H | MISSENSE | 0.636 | 0.0860 | 0.50 |
| SPN | CSPG5 | SPN 5 | CCDS2757.1 | 29 | 12 | 29.3% | g.chr3:47534346C>T | c.172G>A | p.D58N | MISSENSE | 0.992 | 0.9820 | 1.00 |
| SPN | CTNNB1 | SPN 5 | CCDS2694.1 | 20 | 17 | 45.9% | g.chr3:41241101G>C | c.94G>C | p.D32H | MISSENSE | 0.012* | 0.0000 | 0.05 |
| SPN | CTNNB1 | SPN 6 | CCDS2694.1 | 14 | 17 | 54.8% | g.chr3:41241102A>C | c.95A>C | p.D32A | MISSENSE | 0.012* | 0.0000 | 0.05 |
| SPN | CCT5 | SPN 8 | CCDS3877.1 | 37 | 23 | 38.3% | g.chr5:10017601T>C | c.1521T>C | p.I511T | MISSENSE | 0.726 | 0.1790 | 0.65 |
| SPN | CGB5 | SPN 8 | CCDS12752.1 | 39 | 24 | 38.1% | g.chr19:54239646G>A | c.16G>A | p.G6R | MISSENSE | 0.798 | 0.3330 | 0.80 |
| SPN | CTNNB1 | SPN 8 | CCDS2694.1 | 34 | 28 | 45.2% | g.chr3:41241117C>T | c.110C>T | p.S37F | MISSENSE | 0.01** | 0.0000 | 0.05 |
| SPN | DAPLE | SPN 8 | NM_001040214 | 68 | 34 | 33.3% | g.chr14:93433202G>C | c.3026C>G | p.L1010V | MISSENSE | 0.952 | 0.2600 | 1.00 |
| SPN | IGF2R | SPN 8 | CCDS5273.1 | 72 | 49 | 40.5% | g.chr6:160366567A>G | c.587A>G | p.Y196C | MISSENSE | 0.974 | 0.9330 | 1.00 |
| SPN | OBSCN | SPN 8 | ENST00000368699 | 162 | 124 | 43.4% | g.chr1:226654400G>A | c.13246G>A | p.A4412T | MISSENSE | 0.996 | 0.9960 | 1.00 |
| SPN | ZNF43 | SPN 8 | CCDS10673.1 | 64 | 16 | 20.0% | g.chr19:30317406delT | c.1034delT | fs | DELETION | 0.000 | 0.0000 | 0.00 |

SYMBOL KEY:
* MUTATION IN CHASM TRAINING SET
** NO CHASM SCORE AVAILABLE
$ UTR REGION NOT SCORED BY CHASM
$$ SPLICE DONOR/ACCEPTOR NOT SCORED BY CHASM

FIG. 6
CONTINUED

| | | PROTOTYPE FROM 448 TOTAL ROWS | UNIQUE SEQUENCES |
|---|---|---|---|
| | | 1 | 10 |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 1 | 17 |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 1 | 11 |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 1 | 2 |
| | | 0 | |
| | | 1 | 11 |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 0 | |
| | | 1 | 11 |
| | | 0 | |
| | | 0 | |
| | | 0 | |

FIG. 6 CONTINUED

| | | | 0 | |
|---|---|---|---|---|
| | | | 0 | |
| | | | 0 | |
| | | | 0 | |
| | | | 0 | |
| | | | 0 | |
| | | | 0 | |
| | | | 1 | 5 |
| | | | 0 | |
| | | | 0 | |
| | | | 0 | |
| | | | 0 | |
| | | | 1 | 13 |
| | | | 0 | |
| | | | 0 | |
| | | | 0 | |
| | | | 0 | |
| | | | 0 | |
| | | | 0 | |
| | | | 0 | |
| | | | 0 | |
| | | | 0 | |
| | | | 0 | |
| | | | 0 | |

FIG. 6
CONTINUED

| | | | |
|---|---|---|---|
| | | 1 | 3 |
| | | 0 | |
| | | 0 | |
| | | 1 | 1 |
| | | 1 | |
| | | 0 | |
| | | 1 | 2 |
| | | 0 | |
| | | 1 | 5 |
| | | 0 | |
| | | 0 | |
| | | 0 | |
| | | 0 | |
| | | 1 | 2 |
| | | 0 | |
| | | 1 | 1 |
| | | 1 | 7 |
| | | 0 | |
| | | 0 | |
| | | 0 | |
| | | 0 | |
| | | 0 | |
| | | 0 | |
| | | | |
| | | | |
| | | | |
| | | | |
| | | | |

FIG. 6
CONTINUED (DATASET S5): SOMATIC MUTATIONS IN SCAS IDENTIFIED THROUGH VHL-SPECIFIC CAPTURE AND SEQUENCING

| SAMPLE | TRANSCRIPT ACCESSION | DISTINCT WT READS | DISTINCT MUTANT READS | % MUTANT READS | NUCLEOTIDE (GENOMIC) | NUCLEOTIDE (cDNA) | AMINO ACID (PROTEIN) | MUTATION TYPE |
|---|---|---|---|---|---|---|---|---|
| SCA 044 | CCDS2597.1 | 17 | 6 | 26.1% | chr3: 10158771 | c.240T>G | p.S80R | MISSENSE |
| SCA 062 | CCDS2597.1 | 427 | 53 | 11.0% | chr3: 10158797 | c.266T>C | p.L89P | MISSENSE |
| SCA 115 | CCDS2597.1 | 5288 | 167 | 3.1% | chr3: 10158743 | c.212C>G | p.P71R | MISSENSE |
| SCA 117 | CCDS2597.1 | 38 | 3 | 9.5% | chr3: 10158873 | c.340+2T>A | fs | SPLICE DONOR |
| SCA 120 | CCDS2597.1 | 800 | 30 | 3.6% | chr3: 10162247 | c.389DelT | p.130fs*158 | DELETION |
| SCA 131 | CCDS2597.1 | 3862 | 693 | 15.2% | chr3: 10166504 | c.497T>A | p.V166D | MISSENSE |
| SCA 139 | CCDS2597.1 | 1800 | 362 | 16.7% | chr3: 10158694 | c.163G>T | p.E55X | NONSENSE |
| SCA 146 | CCDS2597.1 | 2026 | 175 | 8.0% | chr3: 10166488 | c.481C>T | p.R161X | NONSENSE |
| SCA 148 | CCDS2597.1 | 1801 | 945 | 34.4% | chr3: 10162200 | c.343C>T | p.H115Y | MISSENSE |

FIG. 7

| (DATASET S6.) OLIGONUCLEOTIDES USED FOR LIGATION ASSAYS | | | |
|---|---|---|---|
| PCR AMPLIFICATION PRIMERS | | | |
| MUTATION | OLIGONUCLEOTIDE USED AS: | 5'-MODIFICATION | SEQUENCE |
| VHL N78S | FORWARD PRIMER | NONE | 5'-AGCCCTCCCAGGTCATCTT |
| VHL N78S | REVERSE PRIMER | NONE | 5'-CCGTCGAAGTTGAGCCATAC |
| VHL W117L | FORWARD PRIMER | NONE | 5'-ACCGGTGTGGCTCTTTAACA |
| VHL W117L | REVERSE PRIMER | NONE | 5'-TAACCAGAAGCCCATCGTGT |
| VHL C162W | FORWARD PRIMER | NONE | 5'-CTGCCACTGAGGATTTGGTT |
| VHL C162W | REVERSE PRIMER | NONE | 5'-TTGACTAGGCTCCGGACAAC |
| VHL S80R | FORWARD PRIMER | NONE | 5'-AGCCCTCCCAGGTCATCTT |
| VHL S80R | REVERSE PRIMER | NONE | 5'-CCGTCGAAGTTGAGCCATAC |
| VHL S80R | FORWARD PRIMER | NONE | 5'-AGCCCTCCCAGGTCATCTT |
| VHL S80R | REVERSE PRIMER | NONE | 5'-CCGTCGAAGTTGAGCCATAC |
| VHL V166D | FORWARD PRIMER | NONE | 5'-GGTTTTTGCCCTTCCAGTGT |
| VHL V166D | REVERSE PRIMER | NONE | 5'-TGACGATGTCCAGTCTCCTG |
| VHL R161X | FORWARD PRIMER | NONE | 5'-CTGCCACTGAGGATTTGGTT |
| VHL R161X | REVERSE PRIMER | NONE | 5'-TTGACTAGGCTCCGGACAAC |
| VHL H115Y | FORWARD PRIME | NONE | 5'-ACCGGTGTGGCTCTTTAACA |
| VHL H115Y | REVERSE PRIMER | NONE | 5'-TAACCAGAAGCCCATCGTGT |
| VHL P71R | FORWARD PRIMER | NONE | 5'-GCCGAGGAGGAGATGGAG |
| VHL P71R | REVERSE PRIMER | NONE | 5'-CTGCGATTGCAGAAGATGAC |
| RNF43 R127P | FORWARD PRIMER | NONE | 5'-CCTCAGCCCAACCTCTACTG |
| RNF43 R127P | REVERSE PRIMER | NONE | 5'-GTCAAAGAGGACAGCACTGG |
| RNF43 S41X | FORWARD PRIMER | NONE | 5'-TGGACGCACAGGACTGGTA |
| RNF43 S41X | REVERSE PRIMER | NONE | 5'-GTCCATTTTCAAGGGGATCA |
| RNF43 R145X | FORWARD PRIMER | NONE | 5'-GAGCCAGTGCTGTCCTCTTT |
| RNF43 R145X | REVERSE PRIMER | NONE | 5'-CACCTTGAACACGCAAATGT |
| RNF43 Y177X | FORWARD PRIMER | NONE | 5'-GGGTAATGACGCCTGAGAAGC |
| RNF43 Y177X | REVERSE PRIMER | NONE | 5'-TCAGCTCAATCCTCACATGG |
| RNF43 Q152X | FORWARD PRIMER | NONE | 5'-GCAGGGAGAAGTCACAGCA |
| RNF43 Q152X | REVERSE PRIMER | NONE | 5'-ACCCCAGATCAACACCACTG |
| RNF43 R371X | FORWARD PRIMER | NONE | 5'-CCACTACCACCTCCCTGCT |
| RNF43 R371X | REVERSE PRIMER | NONE | 5'-GATGGCAGGAAGGGACCA |
| RNF43 A169T | FORWARD PRIMER | NONE | 5'-CTGGCCAGTGGTGTTGATCT |
| RNF43 A169T | REVERSE PRIMER | NONE | 5'-AATCCTCACATGGGCCTTTT |
| RNF43 S216X | FORWARD PRIMER | NONE | 5'-GCACCATCTTTGTGATCATCC |
| RNF43 S216X | REVERSE PRIMER | NONE | 5'-AAAGACCCCACACTGCTCAC |
| RNF43 R113X | FORWARD PRIMER | NONE | 5'-GGATTCATCAGCATCGTCAA |
| RNF43 R113X | REVERSE PRIMER | NONE | 5'-GGGCGAAGTGTGAGTCTACC |
| | | | |
| LIGATION PROBES | | | |
| MUTATION | OLIGONUCLEOTIDE USED AS: | 5'-MODIFICATION | SEQUENCE |
| VHL N78S | WT-SPECIFIC PROBE | 6-FAM | 5'-ATGGAGAACTTGACGTCCTCTCATCTTCTGCAA |
| VHL N78S | MUTANT-SPECIFIC PROBE | HEX | 5'-CATCTTCTGCAG |

FIG. 8

| Target | Probe Type | Label | Sequence |
|---|---|---|---|
| VHL N78S | COMMON ANCHORING PROBE | PHOSPHATE | 5'-TCGCAGTCCGCGTGTCCACTAGTCATGCTT |
| VHL W117L | WT-SPECIFIC PROBE | 6-FAM | 5'-ATGGAGAACTTGACGTCCTCAGGTCACCTTTG |
| VHL W117L | MUTANT-SPECIFIC PROBE | HEX | 5'-TAGGTCACCTTTT |
| VHL W117L | COMMON ANCHORING PROBE | PHOSPHATE | 5'-GCTCTTCAGAGATGTGTCCACTAGTCATGCTT |
| VHL C162W | WT-SPECIFIC PROBE | 6-FAM | 5'-ATGGAGAACTTGACGTCCTCAAAGAGCGATGC |
| VHL C162W | MUTANT-SPECIFIC PROBE | HEX | 5'-AAAGAGCGATGG |
| VHL C162W | COMMON ANCHORING PROBE | PHOSPHATE | 5'-CTCCAGGTTGTCCTGTCCACTAGTCATGCTT |
| VHL S80R | WT-SPECIFIC PROBE | 6-FAM | 5'-ATGGAGAACTTGACGTCCTTGCAATCGCAGT |
| VHL S80R | MUTANT-SPECIFIC PROBE | HEX | 5'-AGCAATCGCAGG |
| VHL S80R | COMMON ANCHORING PROBE | PHOSPHATE | 5'-CCGCGCGTCGTTGTCCACTAGTCATGCTT |
| VHL S80R | WT-SPECIFIC PROBE | 6-FAM | 5'-ATGGAGAACTTGACGTCCTCTGCAATCGCAGT |
| VHL S80R | MUTANT-SPECIFIC PROBE | HEX | 5'-GCAATCGCAGG |
| VHL S80R | COMMON ANCHORING PROBE | PHOSPHATE | 5'-CCGCGCGTCGTTGTCCACTAGTCATGCTT |
| VHL V166D | WT-SPECIFIC PROBE | 6-FAM | 5'-ATGGAGAACTTGACGTCCTCCCTCCAGGTTGT |
| VHL V166D | MUTANT-SPECIFIC PROBE | HEX | 5'-CTCCAGGTTGA |
| VHL V166D | COMMON ANCHORING PROBE | PHOSPHATE | 5'-CCGGAGCCTAGTTGTCCACTAGTCATGCTT |
| VHL R161X | WT-SPECIFIC PROBE | 6-FAM | 5'-ATGGAGAACTTGACGTCCTCACTCTGAAAGAGC |
| VHL R161X | MUTANT-SPECIFIC PROBE | HEX | 5'-ACTCTGAAAGAGT |
| VHL R161X | COMMON ANCHORING PROBE | PHOSPHATE | 5'-GATGCCTCCAGGTTGTCCACTAGTCATGCTT |
| VHL H115Y | WT-SPECIFIC PROBE | 6-FAM | 5'-ATGGAGAACTTGACGTCCTCTCCCGATAGGTC |
| VHL H115Y | MUTANT-SPECIFIC PROBE | HEX | 5'-TCCCGATAGGTT |
| VHL H115Y | COMMON ANCHORING PROBE | PHOSPHATE | 5'-ACCTTTGGCTCTTCTGTCCACTAGTCATGCTT |
| VHL P71R | WT-SPECIFIC PROBE | 6-FAM | 5'-ATGGAGAACTTGACGTCCTCCGCGCGGAGCC |
| VHL P71R | MUTANT-SPECIFIC PROBE | HEX | 5'-GCGCGGAGCG |
| VHL P71R | COMMON ANCHORING PROBE | PHOSPHATE | 5'-CTCCCAGGTCATCGTGTCCACTAGTCATGCTT |
| RNF43 R127P | WT-SPECIFIC PROBE | 6-FAM | 5'-ATGGAGAACTTGACGTCCTCCTGCAGGCTCG |
| RNF43 R127P | MUTANT-SPECIFIC PROBE | HEX | 5'-TGCAGGCTCC |
| RNF43 R127P | COMMON ANCHORING PROBE | PHOSPHATE | 5'-GATGGCGGGTGATGTCCACTAGTCATGCTT |
| RNF43 S41X | WT-SPECIFIC PROBE | 6-FAM | 5'-ATGGAGAACTTGACGTCCTCAGTCTGAAAGATC |
| RNF43 S41X | MUTANT-SPECIFIC PROBE | HEX | 5'-AGTCTGAAAGATG |
| RNF43 S41X | COMMON ANCHORING PROBE | PHOSPHATE | 5'-AGCAGAACAGAAAGTGTCCACTAGTCATGCTT |
| RNF43 R145X | WT-SPECIFIC PROBE | 6-FAM | 5'-ATGGAGAACTTGACGTCCTCTCACTGAGGATC |
| RNF43 R145X | MUTANT-SPECIFIC PROBE | HEX | 5'-TCACTGAGGATT |
| RNF43 R145X | COMMON ANCHORING PROBE | PHOSPHATE | 5'-GAGCTGCTGCTGTGTCCACTAGTCATGCTT |
| RNF43 Y177X | WT-SPECIFIC PROBE | 6-FAM | 5'-ATGGAGAACTTGACGTCCTCGGAGTTTGTGTAC |
| RNF43 Y177X | MUTANT-SPECIFIC PROBE | HEX | 5'-AGGAGTTTGTGTAA |
| RNF43 Y177X | COMMON ANCHORING PROBE | PHOSPHATE | 5'-AAGAACCAAAAGGTGTCCACTAGTCATGCTT |
| RNF43 Q152X | WT-SPECIFIC PROBE | 6-FAM | 5'-ATGGAGAACTTGACGTCCTCCTGTAGCTGC |
| RNF43 Q152X | MUTANT-SPECIFIC PROBE | HEX | 5'-CCTGTAGCTGT |
| RNF43 Q152X | COMMON ANCHORING PROBE | PHOSPHATE | 5'-AGCAGCCGCTGGTGTCCACTAGTCATGCTT |

FIG. 8
CONTINUED

| RNF43 R371X | WT-SPECIFIC PROBE | 6-FAM | 5'-ATGGAGAACTTGACGTCCTCCGGCCCCCAC |
| RNF43 R371X | MUTANT-SPECIFIC PROBE | HEX | 5'-CGGCCCCAT |
| RNF43 R371X | COMMON ANCHORING PROBE | PHOSPHATE | 5'-GACCTGGTCCCTTTGTCCACTAGTCATGCTT |
| RNF43 A169T | WT-SPECIFIC PROBE | 6-FAM | 5'-ATGGAGAACTTGACGTCCTCGGGGTAATGACG |
| RNF43 A169T | MUTANT-SPECIFIC PROBE | HEX | 5'-AGGGGTAATGACA |
| RNF43 A169T | COMMON ANCHORING PROBE | PHOSPHATE | 5'-CTGAGAAGCTGATGTGTCCACTAGTCATGCTT |
| RNF43 S216X | WT-SPECIFIC PROBE | 6-FAM | 5'-ATGGAGAACTTGACGTCCTCCATCCTGGCTTC |
| RNF43 S216X | MUTANT-SPECIFIC PROBE | HEX | 5'-CATCCTGGCTTA |
| RNF43 S216X | COMMON ANCHORING PROBE | PHOSPHATE | 5'-GGTGCTGCGCATTGTCCACTAGTCATGCTT |
| RNF43 R113X | WT-SPECIFIC PROBE | 6-FAM | 5'-ATGGAGAACTTGACGTCCTTGGAGAGTCCTC |
| RNF43 R113X | MUTANT-SPECIFIC PROBE | HEX | 5'-TGGAGAGTCCTT |
| RNF43 R113X | COMMON ANCHORING PROBE | PHOSPHATE | 5'-GACGGGCCCCTGTCCACTAGTCATGCTT |

FIG. 8
CONTINUED

DIFFERENTIAL IDENTIFICATION OF PANCREATIC CYSTS

The invention was made with government support under CA 62924, CA 57345, and CA 43460 awarded by National Institutes of Health. The government has certain rights in the invention.

TECHNICAL FIELD OF THE INVENTION

This invention is related to the area of cancer management. In particular, it relates to the areas of prognosis and diagnosis.

BACKGROUND OF THE INVENTION

As the result of the increasing use of abdominal imaging in standard medical practice, pancreatic cysts are being identified with increasing frequency. Management of these cysts is concomitantly becoming a major clinical problem (1, 2). These lesions occur in more than 20% of patients examined at autopsy (3), in as many as 19.6% of patients evaluated by MRI (4-6), and as many as 2.6% of patients evaluated by CT (7, 8). In the vast majority of cases, the cysts are identified as incidental findings in patients undergoing imaging for symptoms unrelated to pancreatic pathology. But once a cyst is identified, it poses a challenging, life-long management problem (1, 2, 9-13). Some cyst types, are virtually always benign, some are low-grade malignant, and others are precursors to invasive pancreatic ductal adenocarcinomas (PDAs), and PDAs are associated with a dismal prognosis (14-17). The distinction among cyst types is therefore critical for the effective management of patients with pancreatic cysts. Unfortunately, it is often difficult to determine the type of cyst from conventional clinical, radio-graphic, or cytologic findings (1, 2, 9-16, 17)

Approximately 40% of cysts are non-neoplastic "pseudo-cysts" that develop as a complication of alcoholic, biliary, or traumatic acute pancreatitis (14-16, 17). They are managed medically or by surgical drainage without resection. The neoplastic cysts (60% of the total cysts) are predominantly of four types: intraductal papillary mucinous neoplasms (IPMNs), mucinous cystic neoplasms (MCNs), and serous cystadenomas (SCAs), and solid pseudopapillary neoplasms (SPNs) (18). SCAs, IPMNs, and MCNs are benign (i.e., non-invasive), but IPMNs and MCNs have the potential to progress to PDAs (i.e., become invasive lesions) if not surgically excised (17). Based on the age of patients undergoing surgical resection, some reports have suggested that there is a 5-year lag time from diagnosis of a large non-invasive IPMN (average age 63.2 years) to diagnosis of an invasive cancer stemming from the IPMN (average age 68.1 years). This provides a broad time window for curative resection if premalignant cysts are accurately identified (19). SPNs are regarded as low grade malignant, but they can be cured by surgery if they are detected and removed prior to their widespread metastasis (20).

IPMNs are the most common type of neoplastic cyst, accounting for ~25% to 35% of the total cysts, while SCAs, MCNs, and SPNs account for ~20%~10%, and ~5% of pancreatic cysts, respectively. SCAs (FIG. 1A) are lined by cuboidal glycogen-rich epithelium with centrally placed round nuclei without atypia (17). SCAs (FIG. 1B) arise within the normal ductal system and are lined by columnar mucin-producing cells which often form large papillary projections into ductal lumina (17). The epithelium of SCAs is associated with a rich capillary network (21). MCN's (FIG. 1C) are also lined by columnar mucin-producing cells, but in contrast to IPMNs, the neoplastic epithelium is associated with a characteristic ovarian-type stroma, and the cysts do not communicate with the ductal system (17). MCNs nearly always occur in the body or tail of the pancreas in women, while IPMNs and SCAs can occur in any part of the pancreas and in both sexes. SPNs (FIG. 1E, F) are technically solid tumors but the vast majority of them undergo cystic degeneration that clinically and radiographically mimic the other types of pancreatic cystic neoplasms (20). Like MCNs, they generally occur in women and do not communicate with the ductal system. Histologically, SPNs consist of uniform poorly cohesive cells supported by delicate small blood vessels. The neoplastic cells of SPNs do not have a normal counterpart in the normal pancreas.

To date, a definitive diagnosis of neoplastic cyst type can usually only be obtained following histopathologic examination of surgically obtained specimens. The decision to surgically resect pancreatic cysts is based on the presumed type of cyst along with clinical parameters. Resection is performed on all cysts which are presumed to be SPNs. In contrast, cysts diagnosed as SCAs only require resection if they are large or cause symptoms. Finally, patients with presumptive MCN or IPMNs undergo surgery if they meet certain criteria such as rapid growth, or the presence of a mural nodule. (1, 2, 9-13). The pre-operative diagnosis of surgically-excised cysts has been shown to be erroneous in one third of cases, which can lead to unnecessary surgical procedures (22). For example, there is no need to excise small asymptomatic SCAs, as they have essentially no malignant potential (17). However, SCAs can be suspected to be IPMNs and therefore be surgically excised (1, 2, 22). Major surgical procedures are often required for removal of these cystic lesions, so more accurate pre-surgical diagnosis has the potential to reduce the cost, morbidity, and occasional mortality associated with unnecessary surgery.

Cyst fluids can easily and safely be obtained from patients with pancreatic cysts by endoscopic aspiration (23-28). These fluids are often acellular and therefore not typically useful for cytologic diagnosis. However, such fluids can be analyzed for the presence of biochemical abnormalities, including those of DNA, and have the potential to inform diagnosis and improve the management of patients with these lesions (23-28). To set the stage for future molecular genetics-based diagnostic assays, we have here determined the sequences of the exomes, including all annotated coding genes, of representative cases of all four types of neoplastic cysts.

There is a continuing need in the art to distinguish among cyst types without the need to obtain surgical samples for the effective management of patients with pancreatic cysts.

SUMMARY OF THE INVENTION

According to one aspect of the invention a method is used to differentially identify a pancreatic cyst. Nucleic acids isolated from cyst fluid or epithelial cells of the pancreatic cyst are tested for mutations characteristic of pancreatic cysts. At least one gene from each of the following groups is tested:
  a. VHL;
  b. GNAS;
  c. RNF43, KRAS; and
  d. CTWVB1.

The pattern of mutations indicates which type of pancreatic cyst it is.

According to another aspect of the invention a method is used to identify a pancreatic cyst as a serous cystadenoma. Nucleic acids isolated from cyst fluid or epithelial cells of the pancreatic cyst are tested for a mutation in VHL. The presence of such a mutation indicates that the cyst is a serous cystadenoma.

Another aspect of the invention is a method of identifying a pancreatic cyst as either an intraductal papillary mucinous neoplasm or a mucinous cystic neoplasm. Nucleic acids isolated from cyst fluid or epithelial cells of the pancreatic cyst are tested for a mutation in RNF43 or KRAS. A mutation in one or both of the genes indicates an intraductal papillary mucinous neoplasm or a mucinous cystic neoplasm.

According to still another aspect of the invention a device can be used for differentially diagnosing pancreatic cysts. The device comprises a solid support comprising a set of oligonucleotides which are complementary to at least one gene from each of the following groups:
a. VHL;
b. GNAS;
c. RNF43, KRAS; and
d. CTNNB1.

The oligonucleotides hybridize to regions containing or adjacent to mutation sites. The solid support comprises oligonucleotides complementary to less than 100 genes.

According to another aspect of the invention a kit aids in differentially diagnosing pancreatic cysts. The kit comprises a set of oligonucleotide primers or probes, which are complementary to at least one gene from each of the following groups:
a. VHL;
b. GNAS;
c. RNF43, KRAS; and
d. CTNNB1

The oligonucleotides hybridize to regions containing or adjacent to mutation sites. The kit comprises oligonucleotides complementary to less than 100 genes.

These and other aspects, which will be apparent to those of skill in the art upon reading the specification, provide the art with methods and tools for better managing medical

BRIEF DESCRIPTION OF THE DRAWINGS

FIG. 1A. A typical SCA (SCA 38) shows centrally placed round nuclei without atypia (Scale bar: 100μ). FIG. 1B. A typical IPMN (IPMN 4) is lined by columnar mucin-producing cells which forms large papillary projections into the ductal lumen (Scale bar: 100μ). FIG. 1C. A typical MCN (MCN) is also lined by columnar mucin-producing cells, but the neoplastic epithelium is associated with a characteristic ovarian-type stroma (Scale bar: 100μ). FIG. 1D. The same MCN after laser capture microdissection of the columnar mucin-producing cells (Scale bar: 100μ). FIG. 1E. Gross appearance of a typical cyst-forming SPN (SPN 2; Scale bar: 10 mm). FIG. 1F. Under the microscope, SPN 17 shows poorly cohesive cells supported by a delicate stroma (Scale bar: 50μ).

FIG. 3A. SCA 40, exhibiting LOH of the region on chromosome the 3p containing the VHL gene. FIG. 3B. IPMN 12, exhibiting LOH of the region on chromosome 17q containing the RNF43 gene. FIG. 3C. MCN 169, exhibiting LOH of the region on chromosome 17q containing the RNF43 gene.

FIG. 5 (Table 1) recurrent genetic alterations in neoplastic cysts of the pancreas FIG. 6. Dataset 4. Somatic mutations identified in neoplastic cysts of the pancreas FIG. 7. Dataset 5. Somatic mutations in SCAs identified through VHL-specific capture and sequencing FIG. 8. Dataset 6. Oligonucleotides used for ligation assays.

DETAILED DESCRIPTION OF THE INVENTION

Figure 1:
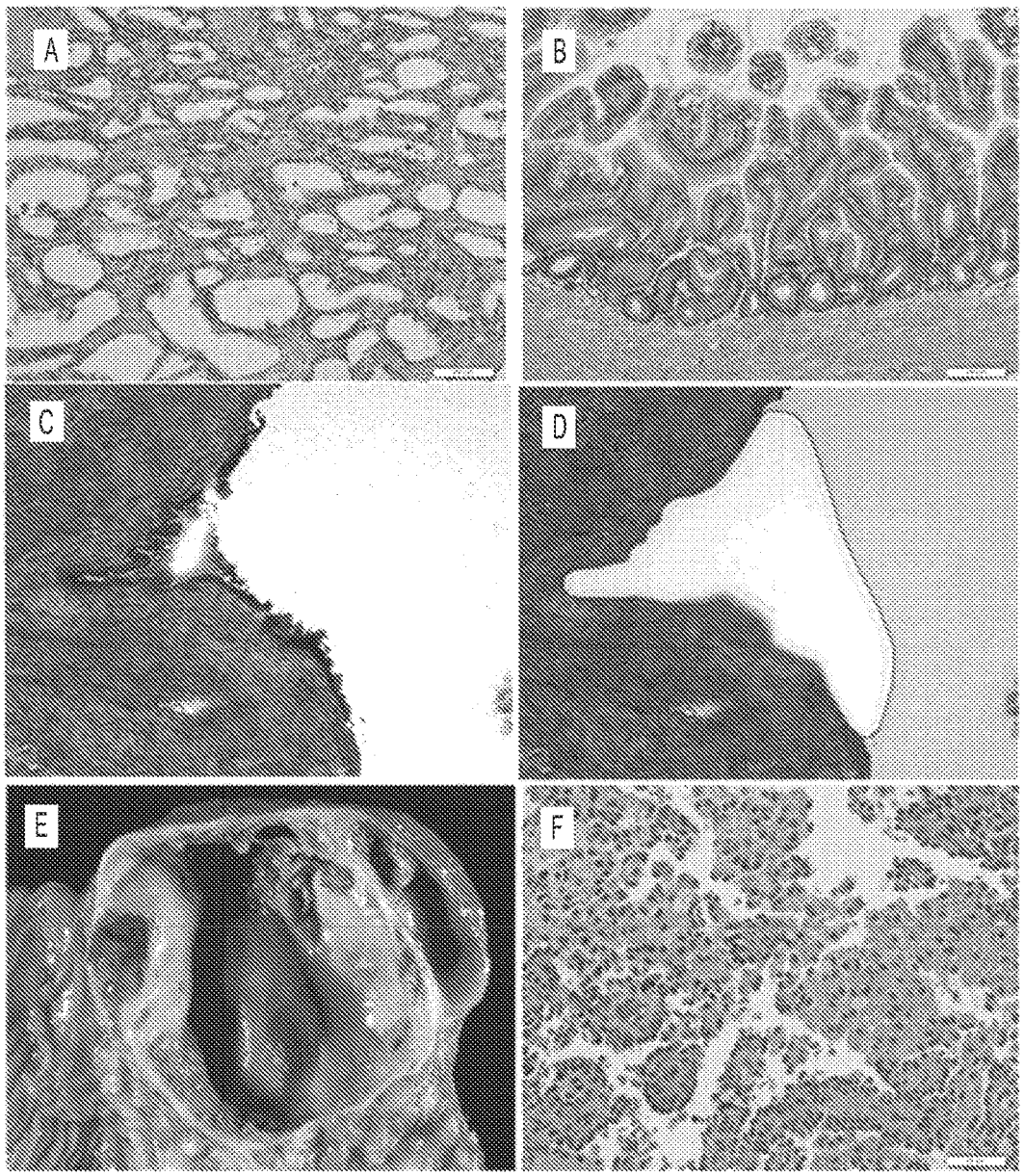
FIG. 1A-1F. Neoplastic cyst histopathology.

The inventors have developed a set of markers which can be used to distinguish between various types of pancreatic cysts. The distinctions can be determined using cyst fluid and/or using epithelial cells from the cyst. Thus a surgical sample is not required. By testing nucleic acids obtained from the cyst fluid or cells, a panel of genes have been identified which are the target of certain types of mutation. These mutations identify the genes as important in the process of neoplastic development. While certain types of mutations have been identified, other mutations or epigenetic changes in the same markers may accomplish the same neoplastic result.

Nucleic acids can be obtained from either cyst fluid or epithelial cells from the cyst. Any test for a substitution mutation, such as a nonsense or missense mutation, can be used. Sequence determination can be used to test for a mutation. Loss of heterozygosity at one of the genes can also be determined. Other mutations that may be tested for and found include frameshifts, splice site, deletions, or translocations. Any test for these genetic events may be used, including those based on hybridization, extension, synthesis, ligation, and amplification. Testing for epigenetic silencing of these genes may also be used. This may involve a change in a methylation pattern such that a gene is expressed much less robustly than in other cells of the body. Typically the mutations that are identified will be somatic mutations. This can be determined by comparing the test pancreatic cyst nucleic acids to nucleic acids from other parts of the body, such as blood cells. Any means for testing mutations as are known in the art may be used, without limitation.

According to the results reported below, recurrent mutations in VHL have been found exclusively in SCA (serous cystadenomas). Mutations in RNF43 and KRAS have been found in both IPMN (intraductal papillary mucinous neoplasms) and MCN (mucinous cystic neoplasms). And mutations in CTNNB1 have been found exclusively in SPN (solid pseudopapillary neoplasms). Mutations in GNAS have been previously found in IPMN (intraductal papillary mucinous neoplasms). Thus running these markers in a battery can very clearly identify the type of cyst and the likelihood of progression. Any single one of these genes may be tested. Any combination of two or more of these genes may be used in a panel.

The battery of genes can conveniently be made into a device which comprises a solid support with oligonucleotide probes or primers attached to the solid support. The oligonucleotides can represent different parts of the genes and can represent different mutant forms. Test can be performed to see if certain mutants are present or to see if certain parts of the gene are missing. Tests can be performed to see if all or part of the gene is adjacent to a different gene or genomic region. For epigenetic silencing, amount of mRNA or cDNA made from mRNA can be assessed by hybridization to a solid support. Typically the device will be for the specific purpose of testing for mutations in pancreatic cysts and will contain a limited number of genes, rather than an entire genome or exome of genes. For example, there may be less than 500, less than 400, less than 300, less than 200, less than 100, less than 75, less than 50, less than 25, or less than 10 genes probes or primers on the solid support. Solid supports may be microarrays, chips, wells, beads, or other suitable format.

Figure 6:
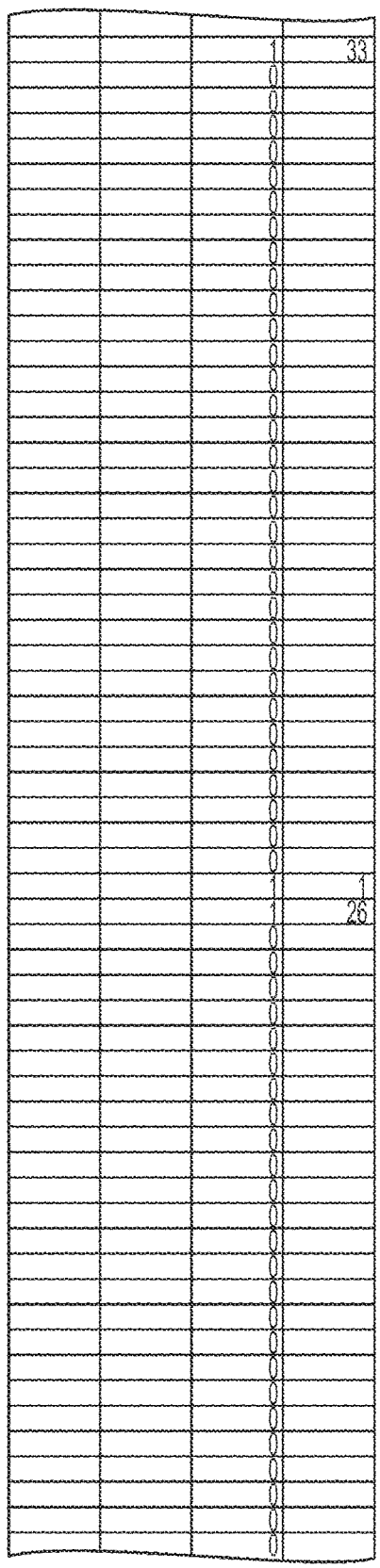
Figure 6:
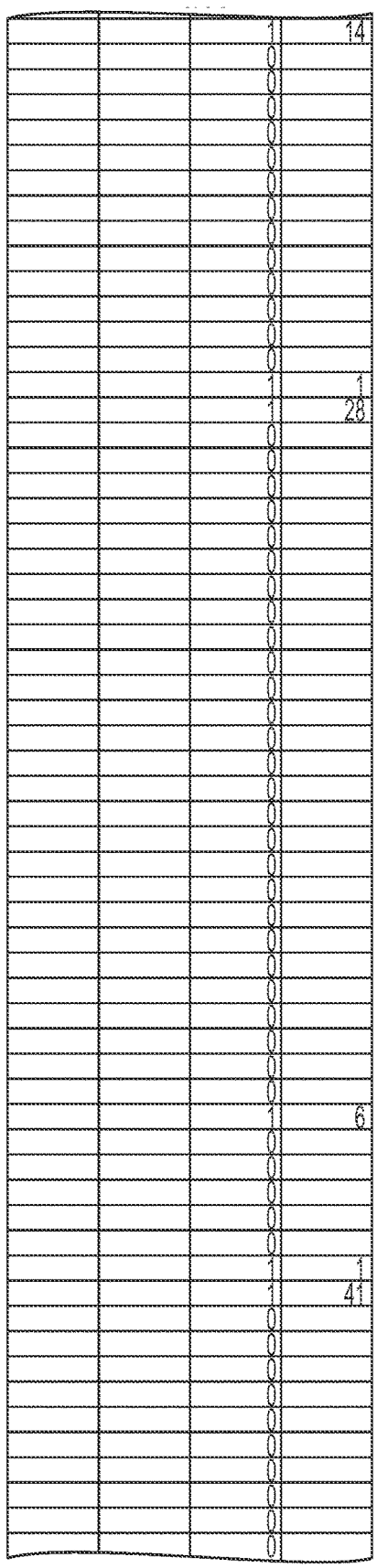
Figure 6:
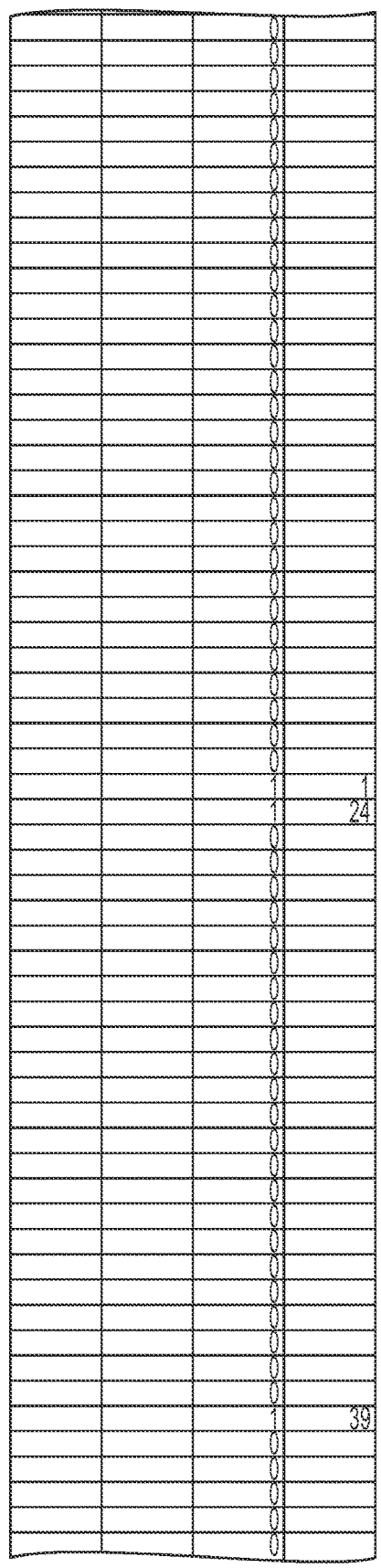
Figure 6:
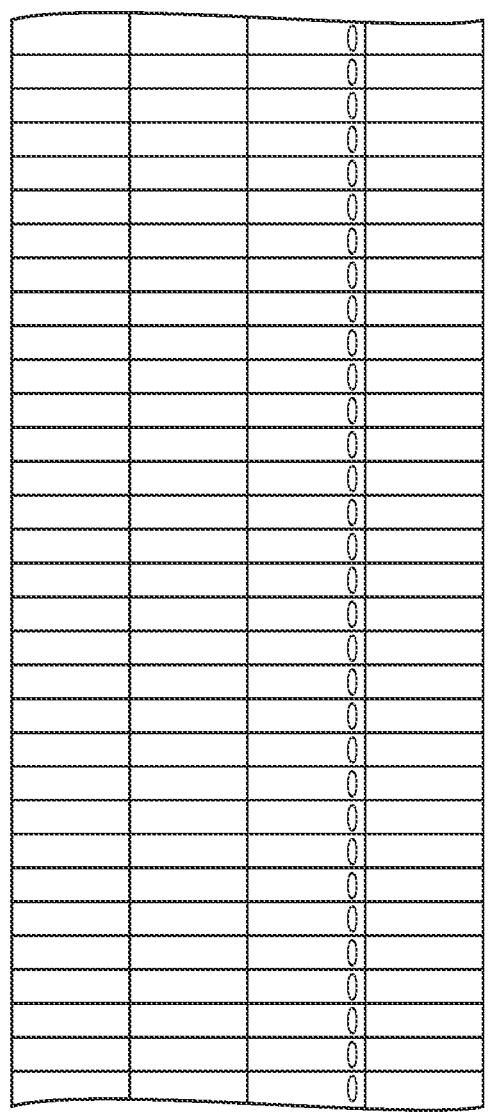
Figure 6:
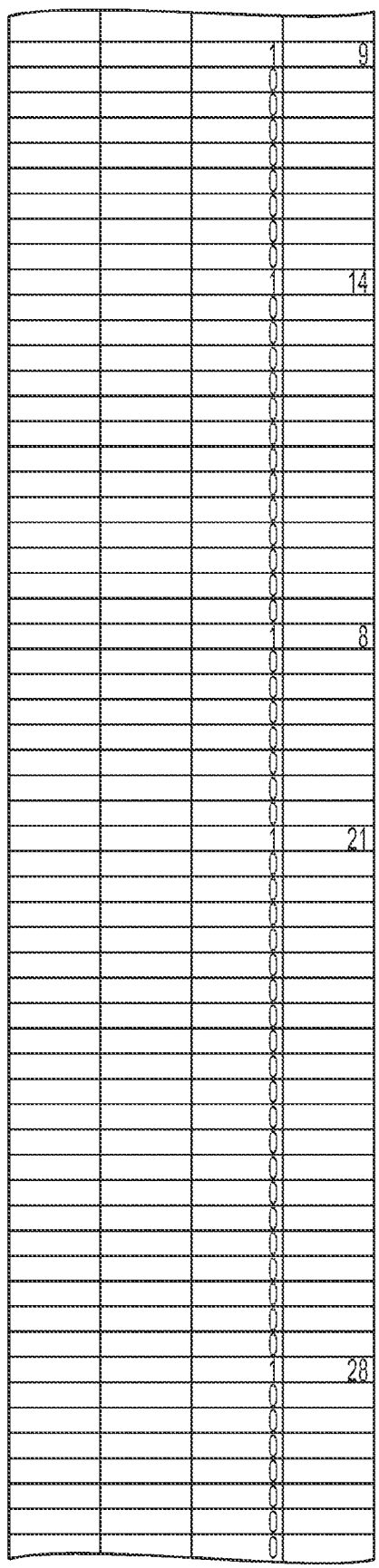
Figure 6:
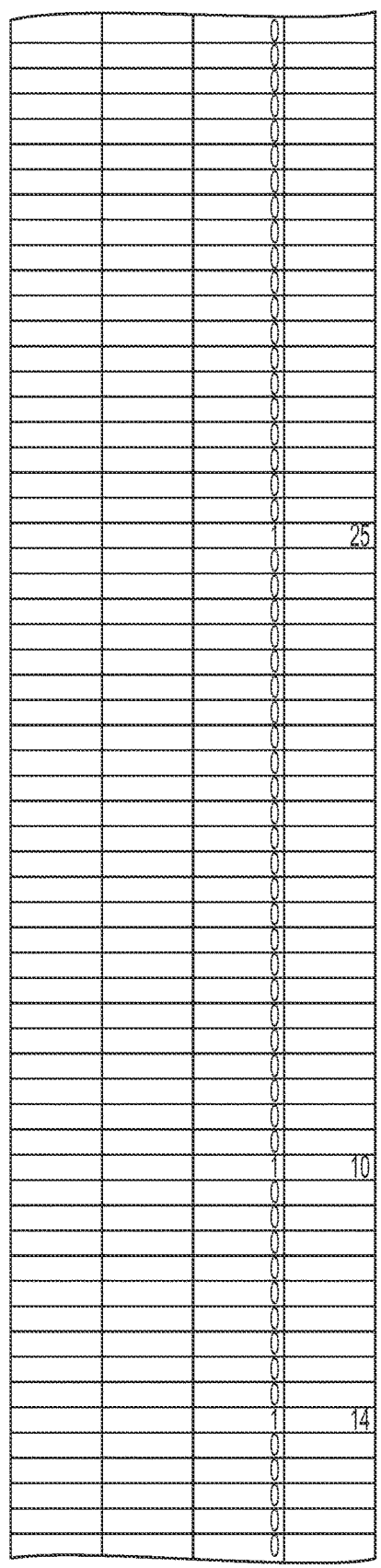
Figure 6:
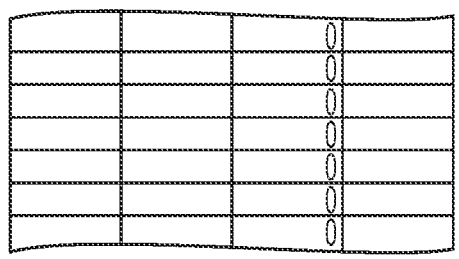

Similarly, a kit can be made for the purpose of identifying a type of pancreatic cyst. The kit may or may not comprise a solid support. Other forms of primers or probes may be used, such as solution phase primers or probes. Test can be performed to see if certain mutants are present or to see if certain parts of the gene are missing. Tests can be performed to see if all or part of the gene is adjacent to a different gene or genomic region. For epigenetic silencing, amount of mRNA or cDNA made from mRNA can be assessed by hybridization to a probe. Typically the kit will be for the specific purpose of testing pancreatic cysts and will contain a limited number of genes, rather than an entire genome or exome of genes. For example, there may be less than 500, less than 400, less than 300, less than 200, less than 100, less than 75, less than 50, less than 25, or less than 10 genes probes or primers in the kit. Without limitation, the oligonucleotide probes and primers may be selected from those shown in FIG. 8 (dataset 6). Any of the mutations identified in FIG. 5 (Table 1) or FIG. 6 (dataset 4) or FIG. 7 (dataset 5) can be tested for. The genes may also be interrogated for other mutations.

The results described above have implications for both basic and applied research. It is fascinating that all four types of cysts are associated with defects in genes that are either components of ubiquitin ligase complexes (SCAs, IPMNs, MCNs) or that render them resistant to degradation by such complexes (SPNs). RNF43, genetically inactivated in both types of mucinous cysts (IPMNs and MCNs), has intrinsic E3 ubiquitin ligase activity (46). There has been relatively little research on this gene's product, though it has been shown to be present in a complex that regulates p53-mediated apoptosis (60). Based on these past studies, it is likely that the tumor suppressor effects of the wild-type RNF43 gene product are a result of its ubiquitin ligase activity. To confirm this hypothesis, it will be important to determine the proteins which protein RNF43 ubiquinates in vivo as well as to demonstrate that such ubiquitination is essential for its tumor suppressive role.

In contrast, VHL has been the subject of intense research since its identification as the gene responsible for the VHL syndrome (61). The most well-studied function of VHL involves its role in angiogenesis (62) (63). When cells are well-oxygenated, prolyl hydroxylation of HIFα proteins leads to their binding to VHL. VHL then recruits a ubiquitin (Ub) ligase complex that leads to the ubiquitination and subsequent degradation of HIFα. When VHL is inactivated, HIFα proteins are stabilized, resulting in the expression of numerous genes that stimulate angiogenesis even when cells are well-oxygenated.

There are at least two ways in which VHL mutations might stimulate SCA formation. First, it has been noted that there is a rich capillary network within SCAs, presumably a result of the abnormal activation of HIFα. This network could disturb local hemodynamics, facilitating the production of cyst fluid, and the increased local concentration of growth factors could stimulate epithelial cell proliferation (21) A second possibility involves the stabilization of microtubules. which is a well-documented but less extensively studied function of the VHL protein (64, 65). In the absence of VHL, primary cilia are absent or defective (66). In view of abundant evidence linking certain types of cysts to defects in primary cilia, it has been suggested that the microtubule-stabilization function of VHL is key to its role in suppressing cysts (66). Several mouse models in which the VHL gene has been inactivated develop various cysts (though not SCAs) (67-70) suggesting fertile avenues for future research on this topic.

Our results also have potentially important diagnostic implications. As mentioned in the Introduction, the distinction between various types of cysts prior to surgical intervention is critically important for patient management (1, 2, 9-16, 17). Cyst fluid can be readily obtained from such patients and subjected to analytical assays (22, 23, 26, 27, 71-73). Our results show that the analysis of only five genes—VHL, RNF43, CTNNB1, GNAS, and KRAS—can usually distinguish between cyst types (Table 1): all eight SCAs had intragenic mutations of VHL or losses of heterozygosity in or adjacent to VHL and did not contain mutations of the other four genes; all eight IPMNs had alterations of RNF43, GNAS, or KRAS, and never had VHL or CTNNB1 mutations; MCNs always harbored KRAS or RNF43 mutations but never contained GNAS, CTNNB1 or VHL mutations; and SPNs always contained CTNNB1 mutations and never contained mutations of the other four genes. When combined with clinical and radiologic data, the molecular genetic analysis of cyst fluid could thereby lead to more accurate diagnosis. For IPMNs and MCNs, it will be important to determine whether the number and type of genetic alterations in GNAS, RNF43, and other genes can be used to help gauge the risk for progression to invasive cancers. The examination of a large number of cyst fluid samples from patients with all four cyst types will be required to determine the added value of molecular genetic analyses for these and other diagnostic purposes.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods
Patients and Specimens

The present study was approved by the Institutional Review Boards of Johns Hopkins Medical Institutions, Memorial Sloan Kettering Cancer Center, Wayne State University Emory University and the University of Indiana. Lesions were classified as IPMNs, MCNs, SPNs or SCAs using standard criteria (74). None of the patients with SCAs had clinical features of the VHL syndrome and all of the SPNs were Stage 1B, pT2N0M0 (74). IPMNs were subtyped by internationally accepted criteria (75).

Fresh-frozen tissue specimens of surgically resected cystic neoplasms of the pancreas were obtained through the prospectively maintained Johns Hopkins Surgical Pathology Tumor Bank and from collaborating institutions (Memorial Sloan Kettering Cancer Center, Emory University, the University of Utrecht and Wayne State University). IPMNs, SCAs, SPNs and two MCNs specimens were microdissected using a razor blade. In these cases, serial frozen sections were used to guide the trimming of OCT embedded tissue blocks. In cases in which an invasive carcinoma was associated with the cystic lesion, only the cystic lesion was harvested. Matched normal pancreatic or splenic tissues of each cyst type were similarly microdissected. Six MCNs were characterized by a particularly abundant ovarian-like stroma underneath the neoplastic epithelium (example in FIG. 1C), necessitating laser capture microdissection (LCM). An average of 50-75 frozen sections (10 µm each) were placed onto UV-treated PALM membrane slides (Carl Zeiss MicroImaging, Inc., Thornwood, N.Y.). After washing in 70% ethanol and standard hematoxylin and eosin staining, sections were subjected to LCM on a PALM Micro Beam System (Carl Zeiss MicroImaging, Inc., Thornwood, N.Y.) (FIG. 1). On average, 5.000 to 10.000 cells were collected from each lesion. Total time of microdissection for each slide was <15 minutes, to minimize DNA degradation.

Pancreatic cyst fluids were harvested in the Surgical Pathology suite from surgically resected pancreatectomy specimens with a sterile syringe. Aspirated fluids were stored at −80° C. within 30 min of resection.

DNA Purification

DNA was purified from cyst walls using an AllPrep kit (Qiagen) according to the manufacturer's instructions. DNA was purified from 250 µL of cyst fluid by adding 3 ml RLTM buffer (Qiagen) and then binding to an AllPrep DNA column (Qiagen) following the manufacturer's protocol. DNA was quantified in all cases with qPCR, employing the primers and conditions previously described (76).

Library Preparation

Libraries were prepared following Illumina's (Illumina, San Digeo, Calif.) protocol, modified as previously described (77). In brief, (1) 1-3 micrograms (µg) of genomic DNA in 100 microliters (µl) of TE was fragmented in a Covaris sonicator (Covaris, Woburn, Mass.) to a size of 100-500 bp. To remove fragments shorter than 150 bp, DNA was mixed with 25 µl of 5× Phusion HF buffer, 416 µl of ddH2O, and 84 µl of NT binding buffer and loaded into NucleoSpin column (cat#636972, Clontech, Mountain View, Calif.). The column was centrifuged at 14,000 g in a desktop centrifuge for 1 min, washed once with 600 µl of wash buffer (NT3 from Clontech), and centrifuged again for 2 min to dry completely. DNA was eluted in 45 µl of elution buffer included in the kit. (2) Purified, fragmented DNA was mixed with 40 µl of H2O, 10 µl of End Repair Reaction Buffer, 5 µl of End Repair Enzyme Mix (cat#E6050, NEB, Ipswich, Mass.). The 100 µl end-repair mixture was incubated at 20° C. for 30 min, purified by a PCR purification kit (Cat #28104, Qiagen) and eluted with 42 µl of elution buffer (EB). (3) To A-tail, all 42 µl of end-repaired DNA was mixed with 5 µl of 10×dA Tailing Reaction Buffer and 3 µl of Klenow (exo-) (cat#E6053, NEB, Ipswich, Mass.). The 50 µl mixture was incubated at 37° C. for 30 min before DNA was purified with a MinElute PCR purification kit (Cat #28004, Qiagen). Purified DNA was eluted with 25 µl of 70° C. EB. (4) For adaptor ligation, 25 µl of A-tailed DNA was mixed with 10 µl of PE-adaptor (Illumina), 10 µl of 5× Ligation buffer and 5 µl of Quick T4 DNA ligase (cat#E6056, NEB, Ipswich, Mass.). The ligation mixture was incubated at 20° C. for 15 min. (5) To purify adaptor-ligated DNA, 50 µl of ligation mixture from step (4) was mixed with 200 µl of NT buffer and cleaned up by NucleoSpin column. DNA was eluted in 50 µl elution buffer. (6) To obtain an amplified library, ten PCRs of 50 µl each were set up, each including 29 µl of H2O, 10 µl of 5× Phusion HF buffer, 1 µl of a dNTP mix containing 10 mM of each dNTP, 2.5 µl of DMSO, 1 µl of Illumina PE primer #1, 1 µl of Illumina PE primer #2, 0.5 µl of Hotstart Phusion polymerase, and 5 µl of the DNA from step (5). The PCR program used was: 98° C. 2 minute; 6 cycles of 98° C. for 15 seconds, 65° C. for 30 seconds, 72° C. for 30 seconds; and 72° C. for 5 min. To purify the PCR product, 500 µl PCR mixture (from the ten PCR reactions) was mixed with 1000 µl NT buffer from a NucleoSpin Extract II kit and purified as described in step (1). Library DNA was eluted with 70° C. elution buffer and the DNA concentration was estimated by absorption at 260 nm.

Exome and Targeted Subgenomic DNA Capture

Human exome capture was performed following a protocol from Agilent's SureSelect Paired-End Target Enrichment System (All Exon 50 Mb kit, Agilent, Santa Clara, Calif.) modified as previously described (77). (1) A hybridization mixture was prepared containing 25 µl of SureSelect Hyb #1, 1 µl of SureSelect Hyb #2, 10 µl of SureSelect Hyb #3, and 13 µl of SureSelect Hyb #4. (2) 3.4 µl (0.5 µg) of the PE-library DNA described above, 2.5 µl of SureSelect Block #1, 2.5 µl of SureSelect Block #2 and 0.6 µl of Block #3; was loaded into one well in a 384-well Diamond PCR plate (cat#AB-1111, Thermo-Scientific, Lafayette, Colo.), sealed with microAmp clear adhesive film (cat#4306311; ABI, Carlsbad, Calif.) and placed in GeneAmp PCR system 9700 thermocycler (Life Sciences Inc., Carlsbad Calif.) for 5 minutes at 95° C., then held at 65° C. (with the heated lid on). (3) 25-30 µl of hybridization buffer from step (1) was heated for at least 5 minutes at 65° C. in another sealed plate with heated lid on. (4) 5 µl of SureSelect Oligo Capture Library, 1 µl of nuclease-free water, and 1 µl of diluted RNase Block (prepared by diluting RNase Block 1:1 with nuclease-free water) were mixed and heated at 65° C. for 2 minutes in another sealed 384-well plate. (5) While keeping all reactions at 65° C., 13 µl of Hybridization Buffer from Step (3) was added to the 7 µl of the SureSelect Capture Library Mix from Step (4) and then the entire contents (9 µl) of the library from Step (2). The mixture was slowly pipetted up and down 8 to 10 times. (6) The 384-well plate was sealed tightly and the hybridization mixture was incubated for 24 hours at 65° C. with a heated lid.

After hybridization, five steps were performed to recover and amplify captured DNA library: (1) Magnetic beads for recovering captured DNA: 50 µl of Dynal MyOne Streptavidin C1 magnetic beads (Cat #650.02, Invitrogen Dynal, AS Oslo, Norway) was placed in a 1.5 ml microfuge tube and vigorously resuspended on a vortex mixer. Beads were washed three times by adding 200 µl of SureSelect Binding buffer, mixed on a vortex for five seconds, and placed in a Dynal magnetic separator to remove the supernatant. After the third wash, beads were resuspended in 200 µl of Sure-Select Binding buffer. (2) To bind captured DNA, the entire hybridization mixture described above (29 µl) was transferred directly from the thermocycler to the bead solution and mixed gently; the hybridization mix/bead solution was incubated in an Eppendorf Thermomixer at 850 rpm for 30 minutes at room temperature. (3) To wash the beads, the supernatant was removed from the beads after applying a Dynal magnetic separator and the beads were resuspended in 500 µl SureSelect Wash Buffer #1 by mixing on a vortex mixer for 5 seconds and incubated for 15 minutes at room temperature. Wash Buffer #1 was then removed from the beads after magnetic separation. The beads were further washed three times, each with 500.1 pre-warmed SureSelect Wash Buffer #2 after incubation at 65° C. for 10 minutes. After the final wash, SureSelect Wash Buffer #2 was completely removed. (4) To elute captured DNA, the beads were suspended in 50 µl SureSelect Elution Buffer, vortex-mixed and incubated for 10 minutes at room temperature. The supernatant was removed after magnetic separation, collected in a new 1.5 ml microCentrifuge tube, and mixed with 50 µl of SureSelect Neutralization Buffer. DNA was purified with a Qiagen MinElute column and eluted in 17.1 of 70° C. EB to obtain 15 µl of captured DNA library. (5) The captured DNA library was amplified in the following way: 15 PCR reactions each containing 9.5 µl of H2O, 3 µl of 5× Phusion HF buffer, 0.3 µl of 10 mM dNTP, 0.75 µl of DMSO, 0.15 µl of Illumina PE primer #1, 0.15 µl of Illumina PE primer #2, 0.15 µl of Hotstart Phusion polymerase, and 1 µl of captured exome library were set up. The PCR program used was: 98° C. for 30 seconds; 14 cycles of 98° C. for 10 seconds, 65° C. for 30 seconds, 72° C. for 30 seconds; and 72° C. for 5 min. To purify PCR products, 225 µl PCR mixture (from 15 PCR reactions) was mixed with 450 µl NT buffer from NucleoSpin Extract II kit and purified as described above. The final library DNA was eluted with 30 µl of 70° C. elution buffer and DNA concentration was estimated by OD260 measurement.

We found that KRAS sequences were not efficiently captured by the All Exon 50 Mb kit, with coverage often less than 10 per base. KRAS was therefore additionally assessed using the ligation assay described below. All KRAS mutations identified by Illumina sequencing were confirmed by ligation, and four additional KRAS mutations were identified (IPMN 11, 20, 26, and 36). These four mutations are included in Table S4, with the quantification provided by digital ligation. Libraries for capturing VHL exons were generated as described above. The libraries were captured as described in (78) using probes designed as described in (79) and (41).

Somatic Mutation Identification

Captured DNA libraries were sequenced with the Illumina GAIIx/HiSeq Genome Analyzer, using 1 lane per sample, yielding 150 (2×75) base pairs from the final library fragments. Sequencing reads were analyzed and aligned to human genome hg18 with the Eland algorithm in CASAVA 1.7 software (Illumina). Duplicate tags were removed and a mismatched base was identified as a mutation only when (i) it was identified by more than five distinct tags; (ii) the number of distinct tags containing a particular mismatched base was at least 20% of the total distinct tags; and (iii) it was not present in >0.1% of the tags in the matched normal sample and (iv) was not present in SNP databases (dbSNP Build 134 Release, from the National Library of Medicine of the National Institutes of Heatlh and from 1000 genomes). CHASM values were determined as previously described (45).

To identify LOH, we evaluated all heterozygous positions identified in the matched normal sample of each cyst. The "minor allele" of each SNP represents the allele that was less common in the tumor. If both alleles of the SNP were represented by an equal number of tags, the minor allele fraction would be represented by 0.5 on the y-axis. Copy number analyses was performed via digital karyotyping (29), binning the number of reads mapping to each gene captured by the SureSelect Oligo Capture Library, Ligation Assays PCR products containing relevant portions of VHL, RNF43, and KRAS were amplified using the primers described in Table S6, using previously described conditions (41) Each 10-ul PCR contained 1 to 100 template molecules in 5 ul of 2× Phusion Flash PCR Master Mix (New England Biolabs) and final concentrations of 0.25 uM forward and 1.5 uM reverse primers. The sequences of the primers used for VHL and RNF43 amplification are provided in Table S6; the KRAS primers have been described previously (41). The following cycling conditions were used: 98° C. for 2 min; 3 cycles of 98° C. for 10 sec., 69° C. for 15 sec, 72° C. for 15 sec; 3 cycles of 98° C. for 10 sec., 66° C. for 15 sec, 72° C. for 15 sec; 3 cycles of 98° C. for 10 sec., 63° C. for 15 sec, 72° C. for 15 sec; 41 cycles of 98° C. for 10 sec., 60° C. for 60 sec. Reactions were performed in at least quadruplicate and each was evaluated independently. Five ul of a solution containing 0.5 ul of Proteinase K, (18.8 mg/ml, Roche,) and 4.5 ul of dH$_2$O was added to each well and incubated at 60° C. for 30 minutes to inactivate the Phusion polymerase and then for 10 min at 98° C. to inactivate the Proteinase K.

The ligation assays (41) were based on previously described techniques employing thermotolerant DNA ligases (80). Each 10-ul reaction contained 2-ul of PCR product (unpurified), 1 ul of 10× Ampligase buffer (Epicentre), 0.5 ul of Ampligase (5 U/ul, Epicentre), anchoring primer (final concentration 2 uM), WT-specific primer (final concentration 0.1 uM), and mutant-specific primer (final concentration 0.025 uM). The sequences of the probes used for VHL and RNF43 ligation assays are provided in Table S6; the KRAS probes have been described previously (41). The following cycling conditions were used: 95° C. for 3 min; 35 cycles of 95° C. for 10 sec., 37° C. for 30 sec, 45° C. for 60 sec. Five ul of each reaction was added to 5 ul of formamide and the ligation products separated on a 10% Urea-Tris-Borate-EDTA gel (Invitrogen) and imaged with an Amersham-GE Typhoon instrument (GE Healthcare).

Statistical Analysis

All values listed as "A±B" in the text correspond to the mean (A) and standard deviation (B). Two-tailed t-Tests assuming unequal sample variances were used to compare distributions unless otherwise noted in the text. P-values were calculated with the data interface available at (http://faculty.vassar.edu/lowry/VassarStats.html).

EXAMPLE 2

Experimental design. Neoplastic cysts are composed of a mixture of neoplastic epithelial cells and non-neoplastic cells (stromal, vascular, and inflammatory (17)) (FIG. 1). To maximize our ability to detect mutations, we carefully microdissected the neoplastic epithelial cells from the non-neoplastic cells. This was most difficult in the MCNs because of the cellular ovarian-type stroma present in these lesions (FIG. 1C, D). Following microdissection, the neoplastic cell content of each of the cyst samples analyzed in this study was at least 33%.

DNA from 32 microdissected cysts, eight of each of the four types, as well as matched DNA from normal tissues of the same patients, was used in this study. The clinical and histopathologic characteristics of the patients and their cystic lesions are detailed in Table S1. The DNA was ligated to adapters and amplified using standard Illumina protocols. The amplified DNA was then captured with a 50 MB SureSelect Enrichment System. The captured DNA includes more than 20,000 coding genes plus all miRNAs in miR-Base, v.13. Sequencing was performed to relatively high depth on Illumina GAII or HiSeq instruments (average unique coverage of 120 fold±40 per bp in the 64 libraries [32 from cyst DNA, 32 from matched normal DNA], Table S2). This level of sequence coverage confers a >99% probability of detecting clonal, heterozygous mutations present in DNA from cyst samples containing >33% neoplastic cells.

EXAMPLE 3

Figure 2:
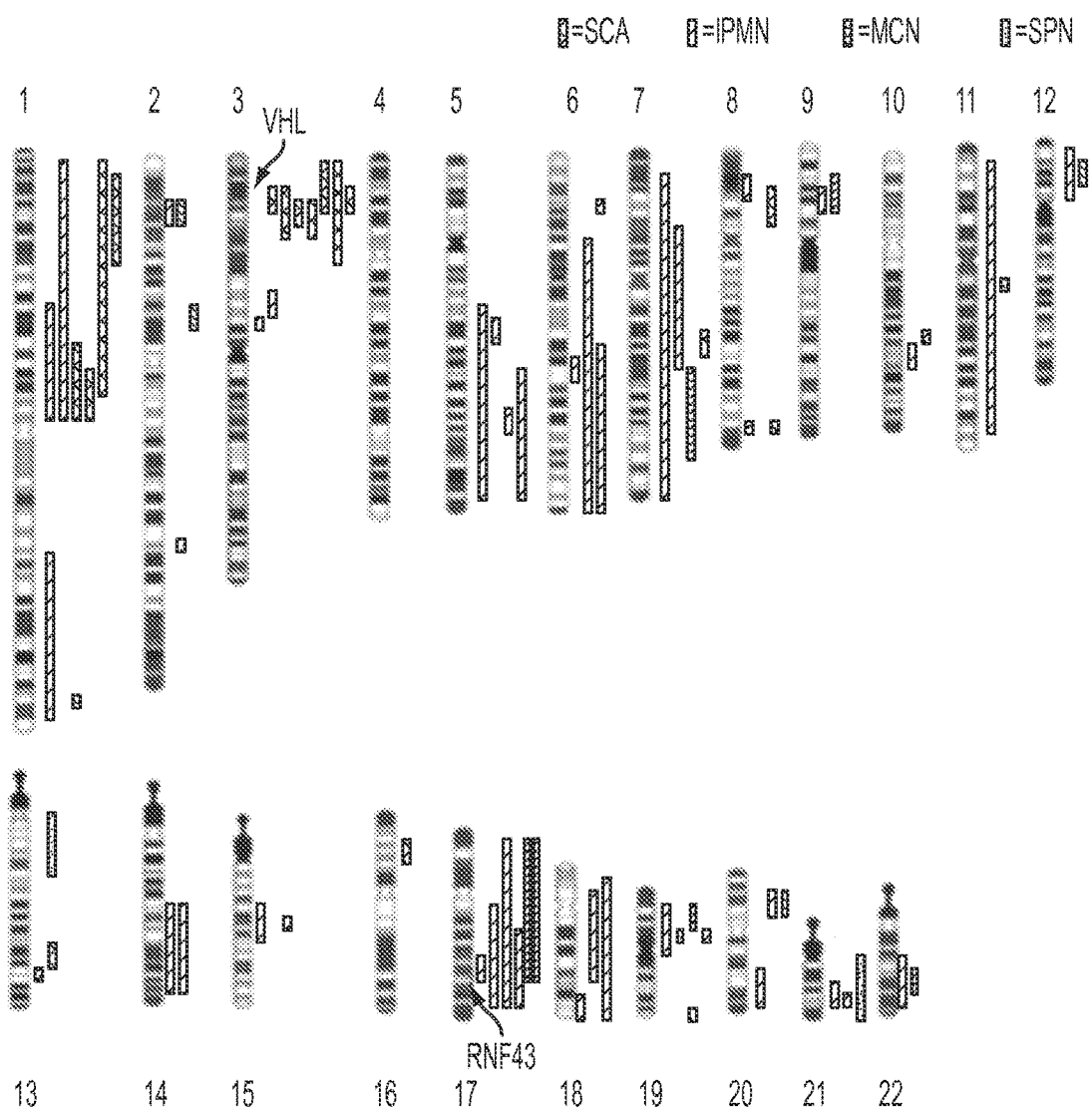
FIG. 2. Losses of heterozygosity observed in neoplastic cysts of the pancreas. The lines indicate the observed regions of loss, with the different cyst types denoted by the indicated colors.

Analysis of SCAs. Using single nucleotide polymorphisms in the sequences captured by the SureSelect Enrichment System, we were able to identify 15,190±428 heterozygous variants in the matched normal DNA samples of the eight SCA patients. Loss of heterozygosity (LOH) of at least one chromosomal region was identified in each of the eight SCAs studied (FIG. 2, Table S3). The maximum degree of LOH (70%±13%) confirmed the high fraction of neoplastic cell content achieved upon microdissection. The only region that was lost in the majority of SCAs was on chromosome 3p (FIG. 2, example in FIG. 3A). Seven of the eight SCAs lost chromosome 3p alleles, with the losses demarcated by bases 9,934,713 to 12,850,443. To determine whether this LOH was associated with reduplication of the remaining allele, we compared the copy number of all sequences lying within the regions of LOH to those of all other chromosomal regions in the same cysts. This was accomplished by comparing normalized tag counts through digital karyotyping (29) as explained in the Materials and Methods section. This analysis showed that in all seven SCAs exhibiting LOH of chromosome 3p, only one copy of chromosome 3p sequences remained in the tumor (assuming that the rest of the genome was on average diploid rather than polyploid).

We have previously described methods for the reliable identification of somatic mutations in next-generation sequencing data obtained from Illumina instruments (30, 31). Using stringent criteria to avoid false positive calls, we identified a total of 79 non-synonymous somatic mutations distributed within 71 genes among the eight SCA tumors (Table S4). There were an average of only 10±4.6 nonsynonymous somatic mutations per tumor, far less than observed in PDAs (48±23 per tumor (32) (p<0.001).

There were only two genes mutated in more than one SCA (Table S4). One of these was TBC1D3 (TBC1 domain family member 3F), in which two missense mutations were observed (Table S4). This gene encodes a protein that stimulates the GTPase activity of RAB5A, which is important for early endosome trafficking (33) (34). Oncogenic properties of TBC1D3 have been demonstrated previously in vitro and in mouse models, and the TBC1D3 locus is amplified in 15% of primary prostate tumors (35) (36). However, whether the two TBC1D3 mutations we identified are drivers or passengers (defined as mutations that did or did not directly contribute to oncogenesis, respectively) is not known. In contrast, the von Hippel-Lindau gene VHL, located on chromosome 3p at position 10,158,319-10,168, 746, is a bona fide tumor suppressor gene (37), and four of the SCAs contained mutations in this gene (N78S in SCA 23, W117L in SCA 35, C162W in SCA 38, and S80R in SCA 40 [Table S4]). Three of these four (SCA 23, 38, and 40) showed evidence of LOH of the VHL chromosomal region (Table S3). Interestingly, the four tumors without detectable mutations of VHL (SCA 14, 27, 29, and 37) had lost one allele of chromosome 3p within or adjacent to VHL (FIG. 2 and Table S3). We speculate that in these four cases, the VHL gene was inactivated by genetic alterations, such as deletions or translocations, not detectable by sequencing or by epigenetic mechanisms such as those responsible for VHL silencing in renal cell carcinomas (38).

Figure 4:
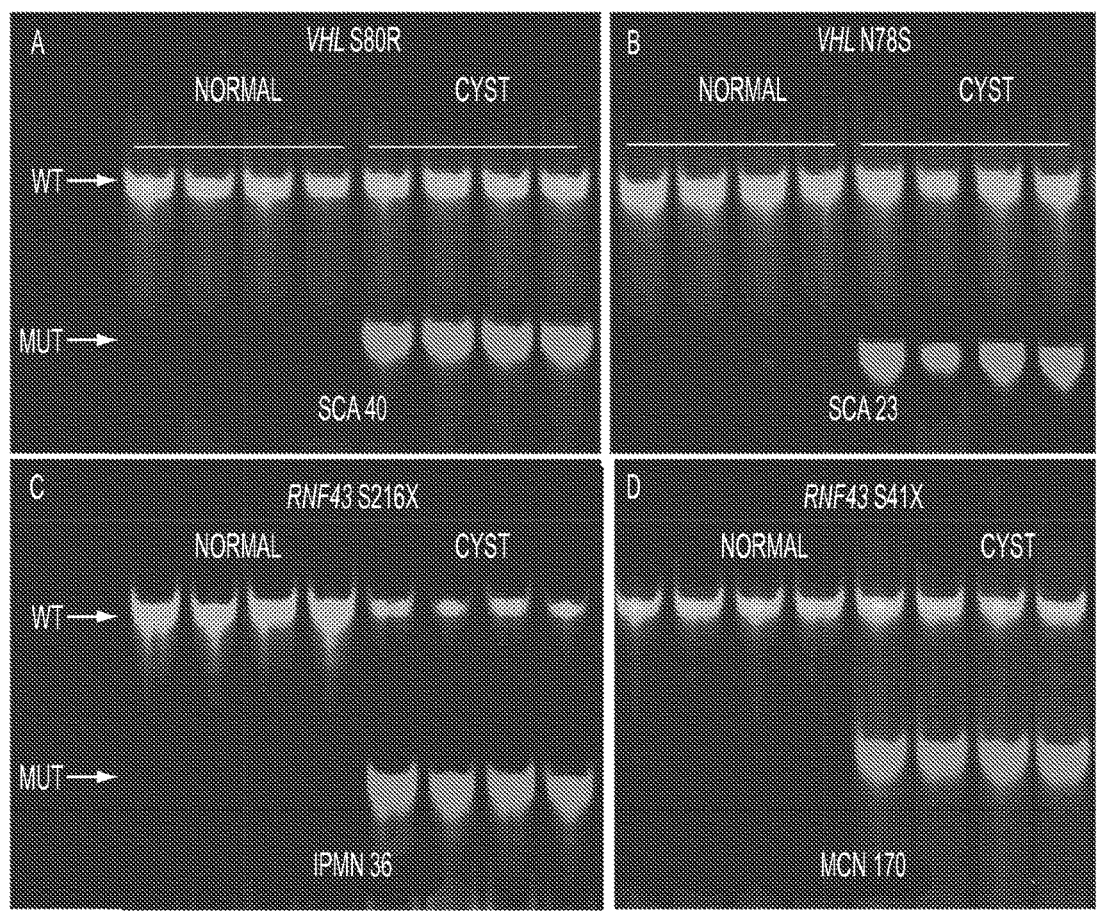
FIG. 4. Ligation assays used to confirm mutations in VHL and RNF43. mutations. Each lane represents the results of ligation of one of four independent PCR products, each containing 100 template molecules. The ligation products are then size-separated on a denaturing acrylamide gel. The green bands are 6-carboxyfluorescein-labeled oligonucleotide probes that ligate to an unlabeled oligonucleotide when wild-type (WT) alleles are present. The red bands are hexachlorofluorescein-labeled oligonucleotide probes that ligate to the same unlabeled oligonucleotide only when mutant (MUT) alleles are present. The WT- and MUT-specific oligonucleotide probes were of different lengths (~32 and ~12 bases, respectively), so they migrated at different positions in the acrylamide gel. The cyst samples and mutations assessed are indicated.

Serous cystadenomas have been identified in more than 15% of patients with the VHL syndrome, a disease that predisposes to renal cell carcinomas (RCCs) and other tumor types (39) (40). Of note, SCAs share several histomorphologic characteristics with RCCs including excessive glycogen production and a distinctive recruitment of vasculature (angiogenesis) All four mutations in VHL identified in SCAs were identical to ones previously identified in renal cell carcinomas (http://www.sanger.ac.uk/geneticsCGP/cosmic/); three of the four were identical to ones previously described in the germline of VHL syndrome patients and the fourth (W117L) was at the same amino acid position found to be mutated in the germline of VHL patients (http://www.umd.be/VHL/). This provides conclusive evidence of the inactivating nature of these mutations in human cells. In each of these four cases, we additionally confirmed that the VHL mutations in the cysts were somatic using independent, ligation-based assays (FIG. 4A)

To our knowledge, no mutations of VHL, or any other gene, have been identified in the fluids obtained from SCA cysts. Demonstration of such mutations in samples obtained by fine needle aspiration could be useful from a diagnostic standpoint, as discussed in the Introduction. To determine whether VHL mutations could be identified in the fluids from SCAs, we designed a customized chip containing VHL gene sequences and used it to capture libraries from the DNA of 18 SCA cyst fluids. In nine (50%) of these cases, we identified point mutations in VHL (Table S5). Four of the mutations were predicted to inactivate the encoded protein's function, as two produced nonsense codons, one was a 1-bp deletion producing a frameshift, and one altered the splice donor site. Of the five missense mutations, four were identical to those observed in the germline of patients with VHL Syndrome. Similar capture of VHL genes from 28 IPMNs and three MCNs revealed no VHL mutations.

EXAMPLE 4

Analysis of IPMNs. In a previous study, in which we analyzed 169 well-annotated cancer genes, we identified recurrent mutations of GNAS and KRAS in IPMN samples, and showed that these mutations were present in 66% and 81% of IPMNs, respectively (41). KRAS mutations had previously been identified in IPMNs as well as in PDAs (42) (43) To extend these analyses, we performed whole exome sequencing on DNA from eight microdissected high-grade IPMNs and matched normal tissues.

LOH of at least one chromosomal region was identified in seven of the eight IPMNs (FIG. 2, Table S3). No losses of the region containing the VHL gene were identified. The most commonly deleted region was on chromosome 17q, demarcated by nt 53,790,884 to 53,939,507, observed in four of the eight samples (FIG. 2, Table S3, example in FIG. 3B). Digital karyotyping showed that in these four cases, the LOH events were not associated with reduplication of the deleted chromosome 17q region.

Using the same criteria described above for SCAs to identify somatic mutations, a total of 211 non-synonymous mutations within 191 genes were identified among the eight IPMNs (Table S4). There were 26±12 non-synonymous somatic mutations per tumor (Table S1), more than twice the number in SCAs ($p<0.001$) and ~half as many as found in PDAs ($p<0.001$).

There were six genes that were mutated in more than one of the eight IPMNs (Table S4). As expected, both KRAS and GNAS mutations were common, each identified in five tumors and always at codons 12 and 201, respectively (Table S4). Two mutations in APC were observed. APC is a well-known tumor suppressor gene whose mutations usually initiate colorectal tumorigenesis(44). One of the APC mutations was a nonsense base substitution (R450X in IPMN 4), typical of the inactivating mutations that occur in the germline of patients with colorectal cancers (http://www.umd.be/APC/). The second was a missense substitution (R99W in Cyst 21) whose functional effects, if any, are unknown. Two different IPMNs had mutations in OBFC1 (oligonucleotide/oligosaccharide-binding fold containing 1) and two others had mutations in CACAN11 (calcium channel, voltage-dependent, T type, alpha 11 subunit). There are no genetic or functional data implicating these two genes in neoplastic processes. CHASM analysis (45), which determines the probability that a given mutation alters the structural or biochemical properties of a protein, showed that the missense mutations in OBFC1 and CACAN11, as well as the one in APC, were not very likely to alter the function of the encoded proteins and may have been passengers. The CHASM scores of all missense mutations identified in this study are provided in Table S3.

The most commonly mutated gene in IPMNs was RNF43, which is located on chromosome 17, nt 53,786,037 to 53,849,930, within the small region of chromosome 17q suffering LOH in IPMNs (Table S3). The protein encoded by RNF43 has been shown to have intrinsic E3 ubiquitin ligase activity (46). RNF43 was mutated in six of the eight tumors, including all four that had undergone chromosome 17q LOH. Five of the six mutations were base pair substitutions resulting in nonsense codons (Table S4). Based on the number and type of mutations in this gene, the probability that it functioned as a passenger was extremely low (<10-12, binomial test). Each of the six RNF43 mutations was confirmed by an independent, ligation-based assay (FIG. 4) Though expression of RNF43 has been shown to be correlated with increased cell growth (47), the inactivating mutations of this gene in IPMNs leave little doubt that it suppresses neoplasia in pancreatic ductal epithelial cells.

EXAMPLE 5

Analysis of MCNs. Relatively few LOH events were identified in the MCN's compared to IPMNs (FIG. 2, Table S3). Only one region was lost in more than one tumor, and this region was on chromosome 17q and included the RNF43 gene (example in FIG. 3C).

A total of 128 non-synonymous somatic mutations distributed within 115 genes were identified among the eight MCNs (Table S4). There were 16.0±7.6 non-synonymous somatic mutations per tumor, more than in SCAs but less than in IPMNs (Table S2). Three MCNs harbored intragenic mutations in RNF43, including oneRNF43 of the two tumors with LOH of the RNF43 locus. RNF43. Two of the alterations were nonsense mutations (S41X and R371X), and the third was a missense mutation (R127P) (Table S4). This type of mutational pattern, with an over-representation of inactivating mutations, is characteristic of tumor suppressor genes and is similar to that observed for RNF43 in IPMNs (Table 1). One of the MCNs with a truncating mutation was a low-grade MCN (MCN 166), while the other two tumors with RNF43 mutations were high-grade MCNs.

In addition to these RNF43 mutations, KRAS mutations were found in six MCNs and TP53 mutations were found in two. The KRAS mutations were all at codon 12, in accord with previous studies of MCNs (41, 48). The TP53 alterations were identical to those observed previously in other cancer types (http://www.sanger.ac.uk/genetics/CGP/cosmic/). As TP53 mutations are often associated with aggressiveness, it is possible that the MCNs with mutations in this gene are the ones most likely to progress to PDAs. Finally, there were two other genes (MUC4 and POTEJ) that were mutated in more than one MCN, but analysis of the mutations by CHASM did not suggest that they would have substantial effects on protein function (Table S4).

EXAMPLE 6

Figure 3:
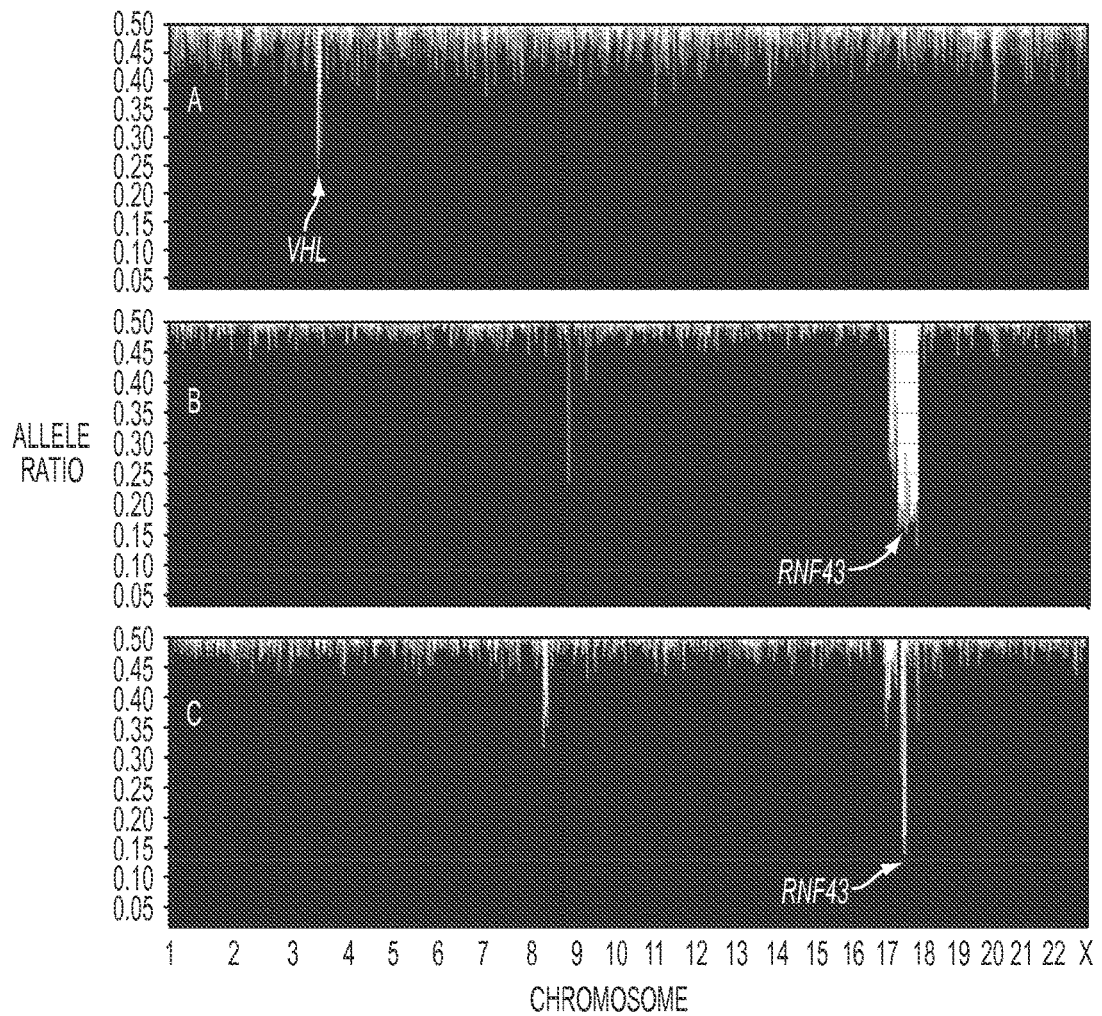
FIG. 3A-3C. Representative LOH data based on the sequence evaluation of genome-wide single nucleotide polymorphisms (SNPs). The positions of the telomeres of the short arm of each chromosome is indicated on the x-axis. The y-axis indicates the ratio of the two alleles of each SNP. In normal cells, this fraction is 0.5; in a pure neoplastic cell population, in which every cell loses one allele of a locus, the allele ratio is 0.0. At a locus in which at least some neoplastic cells had undergone LOH, allele ratios greater than 0.0 reflect non-neoplastic cells that "contaminated" the microdissected cell population plus the fraction of neoplastic cells which had not undergone LOH at that locus.

Analysis of SPNs. The most notable finding about SPNs was the paucity of genetic alterations identified. Only one of the eight tumors studied exhibited any LOH whatsoever (FIG. 2D, FIG. 3, and Table S3). The absence of LOH was not due to contamination of the microdissected samples with non-neoplastic cells; this possibility could be excluded both by histopathologic analysis and by the high fraction of CTNNB1 mutant alleles, as discussed below (39% to 59%; Table S4).

As with LOH, the number of point mutations was also very low (2.9±1.8 mutations per tumor). This number is lower than any of the other cyst types ($p<0.001$), and indeed less than tumor type yet evaluated by genome-wide sequencing (49, 50), including pediatric tumors (51). Five of the eight tumors contained only one or two somatic mutations (Table S4). Nevertheless, every tumor had a missense mutation of CTNNB1, and all these mutations were at codons 32, 33, 34, or 37. This region of the encoded protein (β-catenin) is critical for regulation of the protein (52-54). When phosphorylated at serine or threonine residues lying between codons 32 and 37, beta-catenin is degraded by E3 ubiquitin ligases. Mutations within this region inhibit phosphorylation and the consequent degradation of the protein (55, 56). Previous studies have shown that CTNNB1 is nearly always mutated in SPNs (57, 58). Our study shows that, in many cases, the CTNNB1 mutations are the only mutations that are evident in these tumors, even when all coding genes are assessed by sequencing. An evaluation of these tumors for translocations or epigenetic events may lead to the identification of additional alterations. If not, this tumor type would represent an exception to the widely held view that several, sequential mutations are required for the formation of solid tumors in adults (59).

REFERENCES

The disclosure of each reference cited is expressly incorporated herein.

1. Garcea G, et al. (2008) Cystic lesions of the pancreas. A diagnostic and management dilemma. *Pancreatology* 8:236-251.
2. Tanaka M (2011) Controversies in the management of pancreatic IPMN. *Nat Rev Gastroenterol Hepatol* 8:56-60.
3. Kimura W, Nagai H, Kuroda A, Muto T, & Esaki Y (1995) Analysis of small cystic lesions of the pancreas. *Int J Pancreatol* 18:197-206.
4. Zhang X M, Mitchell D G, Dohke M, Holland G A, & Parker L (2002) Pancreatic cysts: depiction on single-shot fast spin-echo MR images. *Radiology* 223:547-553.
5. de Jong K, et al. (2010) High prevalence of pancreatic cysts detected by screening magnetic resonance imaging examinations. *Clin Gastroenterol Hepatol* 8:806-811.
6. Lee K S, Sekhar A, Rofsky N M, & Pedrosa I (2010) Prevalence of incidental pancreatic cysts in the adult population on M R imaging. *Am J Gastroenterol* 105:2079-2084.
7. Spinelli K S, et al. (2004) Cystic pancreatic neoplasms: observe or operate. *Ann Surg* 239:651-657; discussion 657-659.
8. Laffan T A, et al. (2008) Prevalence of unsuspected pancreatic cysts on MDCT. *AJR Am J Roentgenol* 191:802-807.
9. Allen P J & Brennan M F (2007) The management of cystic lesions of the pancreas. *Adv Surg* 41:211-228.
10. Op de Beeck B, et al. (2007) Management of cystic pancreatic masses. *JBR-BTR* 90:482-486.
11. Carpizo D R, Allen P J, & Brennan M F (2008) Current management of cystic neoplasms of the pancreas. *Surgeon* 6:298-307.
12. Katz M H, et al. (2008) Diagnosis and management of cystic neoplasms of the pancreas: an evidence-based approach. *J Am Col Surg* 207:106-120.
13. Waters J A & Schmidt C M (2008) Intraductal papillary mucinous neoplasm—when to resect? *Adv Surg* 42:87-108.
14. Brugge W R (2008) Management and outcomes of pancreatic cystic lesions. *Dig Liver Dis* 40:854-859.
15. Degen L, Wiesner W, & Beglinger C (2008) Cystic and solid lesions of the pancreas. *Best Pract Res Clin Gastroenterol* 22:91-103.
16. Basturk O, Coban I, & Adsay N V (2009) Pancreatic cysts: pathologic classification, differential diagnosis, and clinical implications. *Arch Pathol Lab Med* 133:423-438.
17. Matthaei H, Schulick R D, Hruban R H, & Maitra A (2011) Cystic precursors to invasive pancreatic cancer. *Nat Rev Gastroenterol Hepatol* 8:141-150.
18. Hruban R H, Maitra A, Kern S E, & Goggins M (2007) Precursors to pancreatic cancer. *Gastroenterol Clin North Am* 36:831-849, vi.
19. Sohn T A, et al. (2004) Intraductal papillary mucinous neoplasms of the pancreas: an updated experience. *Ann Surg* 239:788-797; discussion 797-789.
20. Reddy S & Wolfgang C L (2009) Solid pseudopapillary neoplasms of the pancreas. *Adv Surg* 43:269-282.
21. Thirabanjasak D, Basturk O, Altinel D, Cheng J D, & Adsay N V (2009) Is serous cystadenoma of the pancreas a model of clear-cell-associated angiogenesis and tumorigenesis? *Pancreatology* 9:182-188.
22. Hammel P (2002) Role of tumor markers in the diagnosis of cystic and intraductal neoplasms. *Gastrointest Endosc Clin N Am* 12:791-801.
23. van der Waaij L A, van Dullemen H M, & Porte R J (2005) Cyst fluid analysis in the differential diagnosis of pancreatic cystic lesions: a pooled analysis. *Gastrointest Endosc* 62:383-389.
24. Khalid A & Brugge W (2007) ACG practice guidelines for the diagnosis and management of neoplastic pancreatic cysts. *Am J Gastroenterol* 102:2339-2349.
25. Vazquez-Sequeiros E (2007) Endoscopic ultrasound and fine needle aspiration in inflammatory and cystic pancreatic pathology. *Minerva Med* 98:357-360.
26. Anderson M A, Kwon R S, & Scheiman J M (2009) PANDA cyst-fluid analysis: eats, shoots and leaves? *Gastrointest Endosc* 69:1103-1105.
27. Khalid A, et al. (2009) Pancreatic cyst fluid DNA analysis in evaluating pancreatic cysts: a report of the PANDA study. *Gastrointest Endosc* 69:1095-1102.
28. Maker A V (2011) Cyst fluid interleukin-1b (IL1b) levels predict the risk of carcinoma in intraductal papillary mucinous neoplasms of the pancreas *Clinical Cancer Research*.
29. Wang T L, et al. (2002) Digital karyotyping. *Proc Natl Acad Sci USA* 99:16156-16161.
30. Jiao Y, et al. (2011) DAXX/ATRX, MEN1, and mTOR pathway genes are frequently altered in pancreatic neuroendocrine tumors. *Science* 331:1199-1203.
31. Jones S, et al. (2010) Frequent mutations of chromatin remodeling gene ARID1A in ovarian clear cell carcinoma. *Science* 330:228-231.
32. Jones S, et al. (2008) Core signaling pathways in human pancreatic cancers revealed by global genomic analyses. *Science* 321:1801-1806.
33. Wainszelbaum M J, et al. (2008) The hominoid-specific oncogene TBC 1D3 activates Ras and modulates epidermal growth factor receptor signaling and trafficking. *J Biol Chem* 283:13233-13242.
34. Stenmark H (2009) Rab GTPases as coordinators of vesicle traffic. *Nat Rev Mol Cell Biol* 10:513-525.
35. Nakamura T, et al. (1992) A novel transcriptional unit of the tre oncogene widely expressed in human cancer cells. *Oncogene* 7:733-741.
36. Pei L, et al. (2002) PRC 17, a novel oncogene encoding a Rab GTPase-activating protein, is amplified in prostate cancer. *Cancer Res* 62:5420-5424.
37. Linehan W M, et al. (2009) Hereditary kidney cancer: unique opportunity for disease-based therapy. *Cancer* 115:2252-2261.
38. Herman J G, et al. (1994) Silencing of the VHL tumor-suppressor gene by DNA methylation in renal carcinoma. *Proc Natl Acad Sci USA* 91:9700-9704.
39. Choyke P L, et al. (1995) von Hippel-Lindau disease: genetic, clinical, and imaging features. *Radiology* 194:629-642.
40. Neumann H P, et al. (1991) Pancreatic lesions in the von Hippel-Lindau syndrome. *Gastroenterology* 101:465-471.
41. Wu J, et al. (2011) Recurrent GNAS Mutations Define an Unexpected Pathway for Pancreatic Cyst Development. *Sci Trans Med* 3:92ra66.
42. Kitago M, et al. (2004) Comparison of K-ras point mutation distributions in intraductal papillary-mucinous tumors and ductal adenocarcinoma of the pancreas. *Int J Cancer* 110:177-182.
43. Almoguera C, et al. (1988) Most human carcinomas of the exocrine pancreas contain mutant c-K-ras genes. *Cell* 53:549-554.
44. Kinzler K W & Vogelstein B (1996) Lessons from hereditary colorectal cancer. *Cell* 87:159-170.

45. Carter H, et al. (2009) Cancer-specific high-throughput annotation of somatic mutations: computational prediction of driver missense mutations. *Cancer Res* 69:6660-6667.
46. Sugiura T, Yamaguchi A, & Miyamoto K (2008) A cancer-associated RING finger protein, RNF43, is a ubiquitin ligase that interacts with a nuclear protein, HAP95. *Exp Cell Res* 314:1519-1528.
47. Yagyu R, et al. (2004) A novel oncoprotein RNF43 functions in an autocrine manner in colorectal cancer. *Int J Oncol* 25:1343-1348.
48. Khalid A. Finkelstein S. & McGrath K (2004) Molecular diagnosis of solid and cystic lesions of the pancreas. *Gastroenterol Clin North Am* 33:891-906.
49. Chin L, Hahn W C, Getz G, & Meyerson M (2011) Making sense of cancer genomic data. *Genes Dev* 25:534-555.
50. Stratton M R (2011) Exploring the genomes of cancer cells: progress and promise. *Science* 331:1553-1558.
51. Parsons D W, et al. (2011) The genetic landscape of the childhood cancer medulloblastoma. *Science* 331:435-439.
52. Clevers H (2006) Wnt/beta-catenin signaling in development and disease. *Cell* 127:469-480.
53. Nelson W J & Nusse R (2004) Convergence of Wnt, beta-catenin, and cadherin pathways. *Science* 303:1483-1487.
54. Verheyen E M & Gottardi C J (2010) Regulation of Wnt/bcta-catenin signaling by protein kinases. *Dev Dyn* 239:34-44.
55. Morin P J, et al. (1997) Activation of beta-catenin-Tcf signaling in colon cancer by mutations in beta-catenin or APC. *Science* 275:1787-1790.
56. Rubinfeld B, et al. (1997) Stabilization of beta-catenin by genetic defects in melanoma cell lines. *Science* 275:1790-1792.
57. Tanaka Y, et al. (2001) Frequent beta-catenin mutation and cytoplasmic/nuclear accumulation in pancreatic solid-pseudopapillary neoplasm. *Cancer Res* 61:8401-8404.
58. Abraham S C, et al. (2002) Solid-pseudopapillary tumors of the pancreas are genetically distinct from pancreatic ductal adenocarcinomas and almost always harbor beta-catenin mutations. *Am J Pathol* 160:1361-1369.
59. Vogelstein B & Kinzler K W (2004) Cancer genes and the pathways they control. *Nat Med* 10:789-799.
60. Shinada K, et al. (2011) RNF43 interacts with NEDL1 and regulates p53-mediated transcription. *BioChem Biophys Res Commun* 404:143-147.
61. Latif F, et al. (1993) Identification of the von Hippel-Lindau disease tumor suppressor gene. *Science* 260:1317-1320.
62. Semenza G L (2011) Hypoxia-inducible factor 1: regulator of mitochondrial metabolism and mediator of ischemic preconditioning. *BioChim Biophys Acta* 1813:1263-1268.
63. Kaelin W G, Jr. (2008) The von Hippel-Lindau tumour suppressor protein: 02 sensing and cancer. *Nat Rev Cancer* 8:865-873.
64. Hergovich A, Lisztwan J, Barry R, Ballschmieter P, & Krek W (2003) Regulation of microtubule stability by the von Hippel-Lindau tumour suppressor protein pVHL. *Nat Cell Biol* 5:64-70.
65. Lolkema M P, et al. (2004) The von Hippel-Lindau tumor suppressor protein influences microtubule dynamics at the cell periphery. *Exp Cell Res* 301:139-146.
66. Thoma C R, et al. (2007) pVHL and GSK3beta are components of a primary cilium-maintenance signalling network. *Nat Cell Biol* 9:588-595.
67. Rankin E B, Tomaszewski J E, & Haase V H (2006) Renal cyst development in mice with conditional inactivation of the von Hippel-Lindau tumor suppressor. *Cancer Res* 66:2576-2583.
68. Frew I J, et al. (2008) pVHL and PTEN tumour suppressor proteins cooperatively suppress kidney cyst formation. *EMBO J* 27:1747-1757.
69. Shen H C, et al. (2009) Deciphering von Hippel-Lindau (VHL/Vhl)-associated pancreatic manifestations by inactivating Vhl in specific pancreatic cell populations. *PLoS One* 4:e4897.
70. Fu L, Wang G, Shevchuk M M, Nanus D M, & Gudas L J (2011) Generation of a Mouse Model of Von Hippel-Lindau Kidney Disease Leading to Renal Cancers by Expression of a Constitutively Active Mutant of HIF 1 {alpha}. *Cancer Res*.
71. Sawhney M S, et al. (2009) Comparison of carcinoembryonic antigen and molecular analysis in pancreatic cyst fluid. *Gastrointest Endosc* 69:1106-1110.
72. Maker A V, et al. (2011) Cyst fluid interleukin-1b (IL1b) levels predict the risk of carcinoma in intraductal papillary mucinous neoplasms of the pancreas. *Clin Cancer Res*.
73. Mertz H (2011) K-ras Mutations Correlate with Atypical Cytology and Elevated CEA Levels in Pancreatic Cystic Neoplasms. *Dig Dis Sci*.
74. Bosman F T, Carneiro F, Hruban R H, & Thiese N D (2010) *WHO Classification of Tumours of the Digestive system*. (IARC Press, Lyon) 4 Ed.
75. Furukawa T, et al. (2005) Classification of types of intraductal papillary-mucinous neoplasm of the pancreas: a consensus study. *Virchows Arch* 447:794-799.
76. Rago C, et al. (2007) Serial Assessment of Human Tumor Burdens in Mice by the Analysis of Circulating DNA. *Cancer Res* 67:9364-9370.
77. Bettegowda C, et al. (2011) Mutations in CIC and FUBPI Contribute to Human Oligodendroglioma. *Science*.
78. Herman D S, et al. (2009) Filter-based hybridization capture of subgenomes enables resequencing and copy-number detection. *Nat Methods* 6:507-510.
79. He J, et al. (2011) IgH gene rearrangements as plasma biomarkers in Non-Hodgkin's Lymphoma patients. *Oncotarget* 2.
80. Fouquet C, et al. (2004) Rapid and sensitive p53 alteration analysis in biopsies from lung cancer patients using a functional assay and a universal oligonucleotide array: a prospective study. *Clin Cancer Res* 10:3479-3489.

We claim:

1. A device comprising:
a solid support comprising an attached set of oligonucleotides which are complementary to at least one gene from each of the following groups:
   a. VHL;
   b. GNAS;
   c. RNF43, KRAS; and
   d. CTNNB1
wherein the oligonucleotides hybridize to regions containing or adjacent to mutation sites, wherein the solid support comprises oligonucleotides complementary to less than 100 genes.

2. A kit comprising:
a set of oligonucleotide primers or probes which are attached to a solid support and complementary to at least one gene from each of the following groups:
   a. VHL;
   b. GNAS;
   c. RNF43, KRAS; and
   d. CTNNB1
wherein the oligonucleotides hybridize to regions containing or adjacent to mutation sites, wherein the kit comprises oligonucleotides complementary to less than 100 genes.

3. The device of claim 1 which comprises an attached oligonucleotide which is complementary to RNF43.

4. The kit of claim 2 which comprises an oligonucleotide primer or probe which is complementary to RNF43.

* * * * *

UNITED STATES PATENT AND TRADEMARK OFFICE
CERTIFICATE OF CORRECTION

PATENT NO.       : 9,637,796 B2
APPLICATION NO.  : 14/359149
DATED            : May 2, 2017
INVENTOR(S)      : Vogelstein et al.

It is certified that error appears in the above-identified patent and that said Letters Patent is hereby corrected as shown below:

On the Title Page

Column 1, under (65) Prior Publication Data, please insert:
-- Related U.S. Application Data
(60) Provisional application No. 61/561,106, filed on Nov. 17, 2011. --

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 90

<210> SEQ ID NO 1
<211> LENGTH: 19

```
<212> TYPE: DNA
<213> ORGANISM: Artificial Sequence
<220> FEATURE:
<223> OTHER INFORMATION: amplification primers and ligase assay probes

<400> SEQUENCE: 1
agccctccca ggtcatctt                                                19

<210> SEQ ID NO 2
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 2
ccgtcgaagt tgagccatac                                               20

<210> SEQ ID NO 3
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 3
accggtgtgg ctctttaaca                                               20

<210> SEQ ID NO 4
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 4
taaccagaag cccatcgtgt                                               20

<210> SEQ ID NO 5
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 5
ctgccactga ggatttggtt                                               20

<210> SEQ ID NO 6
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 6
ttgactaggc tccggacaac                                               20

<210> SEQ ID NO 7
<211> LENGTH: 19
<212> TYPE: DNA
<213> ORGANISM: Artificial Sequence
<220> FEATURE:
<223> OTHER INFORMATION: amplification primers and ligase assay probes

<400> SEQUENCE: 7
```
agccctccca ggtcatctt                                                19

<210> SEQ ID NO 8
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 8
ccgtcgaagt tgagccatac                                               20

<210> SEQ ID NO 9
<211> LENGTH: 19
<212> TYPE: DNA
<213> ORGANISM: Artificial Sequence
<220> FEATURE:
<223> OTHER INFORMATION: amplification primers and ligase assay probes

<400> SEQUENCE: 9
agccctccca ggtcatctt                                                19

<210> SEQ ID NO 10
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 10
ccgtcgaagt tgagccatac                                               20

<210> SEQ ID NO 11
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 11 ggttttttgcc cttccagtgt                                              20

<210> SEQ ID NO 12
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 12
tgacgatgtc cagtctcctg                                               20

<210> SEQ ID NO 13
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 13
ctgccactga ggatttggtt                                               20

<210> SEQ ID NO 14
<211> LENGTH: 20
<212> TYPE: DNA
<213> ORGANISM: Artificial Sequence

```
<220> FEATURE:
<223> OTHER INFORMATION: ampilification primers and ligase assay probes

<400> SEQUENCE: 14
ttgactaggc tccggacaac                                               20

<210> SEQ ID NO 15
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 15
accggtgtgg ctctttaaca                                               20

<210> SEQ ID NO 16
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 16
taaccagaag cccatcgtgt                                               20

<210> SEQ ID NO 17
<211> LENGTH: 18
<212> TYPE: DNA
<213> ORGANISM: Artificial Sequence
<220> FEATURE:
<223> OTHER INFORMATION: ampilification primers and ligase assay probes

<400> SEQUENCE: 17
gccgaggagg agatggag                                                 18

<210> SEQ ID NO 18
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 18
ctgcgattgc agaagatgac                                               20

<210> SEQ ID NO 19
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 19
cctcagccca acctctactg                                               20

<210> SEQ ID NO 20
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 20
gtcaaagagg acagcactgg                                               20
```

```
<210> SEQ ID NO 21
<211> LENGTH: 19
<212> TYPE: DNA
<213> ORGANISM: Artificial Sequence
<220> FEATURE:
<223> OTHER INFORMATION: amplification primers and ligase assay probes

<400> SEQUENCE: 21
tggacgcaca ggactggta                                                      19

<210> SEQ ID NO 22
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 22
gtccattttc aagggatca                                                      20

<210> SEQ ID NO 23
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 23
gagccagtgc tgtcctcttt                                                     20

<210> SEQ ID NO 24
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 24
caccttgaac acgcaaatgt                                                     20

<210> SEQ ID NO 25
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 25
gggtaatgac gctgagaagc                                                     20

<210> SEQ ID NO 26
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 26
tcagctcaat cctcacatgg                                                     20

<210> SEQ ID NO 27
<211> LENGTH: 19
<212> TYPE: DNA
<213> ORGANISM: Artificial Sequence
<220> FEATURE:
<223> OTHER INFORMATION: amplification primers and ligase assay probes
```

<400> SEQUENCE: 27
gcagggagaa gtcacagca                                                    19

<210> SEQ ID NO 28
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 28
accccagatc aacaccactg                                                   20

<210> SEQ ID NO 29
<211> LENGTH: 19
<212> TYPE: DNA
<213> ORGANISM: Artificial Sequence
<220> FEATURE:
<223> OTHER INFORMATION: ampilification primers and ligase assay probes

<400> SEQUENCE: 29
ccactaccac ctccctgct                                                    19

<210> SEQ ID NO 30
<211> LENGTH: 18
<212> TYPE: DNA
<213> ORGANISM: Artificial Sequence
<220> FEATURE:
<223> OTHER INFORMATION: ampilification primers and ligase assay probes

<400> SEQUENCE: 30
gatggcagga agggacca                                                     18

<210> SEQ ID NO 31
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 31
ctggccagtg gtgttgatct                                                   20

<210> SEQ ID NO 32
<211> LENGTH: 20
<212> TYPE: DNA
<213> ORGANISM: Artificial Sequence
<220> FEATURE:
<223> OTHER INFORMATION: ampilification primers and ligase assay probes

<400> SEQUENCE: 32
aatcctcaca tgggcctttt                                                   20

<210> SEQ ID NO 33
<211> LENGTH: 21
<212> TYPE: DNA
<213> ORGANISM: Artificial Sequence
<220> FEATURE:
<223> OTHER INFORMATION: ampilification primers and ligase assay probes

<400> SEQUENCE: 33
gcaccatctt tgtgatcatc c                                                 21

<210> SEQ ID NO 34

```
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 34 aaagaccccca cactgctcac                                              20

<210> SEQ ID NO 35
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 35
ggattcatca gcatcgtcaa                                               20

<210> SEQ ID NO 36
<211> LENGTH: 20
<212> TYPE: DNA
<213> ORGANISM: Artificial Sequence
<220> FEATURE:
<223> OTHER INFORMATION: amplification primers and ligase assay probes

<400> SEQUENCE: 36
gggcgaagtg tgagtctacc                                               20

<210> SEQ ID NO 37
<211> LENGTH: 33
<212> TYPE: DNA
<213> ORGANISM: Artificial Sequence
<220> FEATURE:
<223> OTHER INFORMATION: amplification primers and ligase assay probes

<400> SEQUENCE: 37
atggagaact tgacgtcctc tcatcttctg caa                                33

<210> SEQ ID NO 38
<211> LENGTH: 12
<212> TYPE: DNA
<213> ORGANISM: Artificial Sequence
<220> FEATURE:
<223> OTHER INFORMATION: amplification primers and ligase assay probes

<400> SEQUENCE: 38
catcttctgc ag                                                       12

<210> SEQ ID NO 39
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 39
tcgcagtccg cgtgtccact agtcatgctt                                    30

<210> SEQ ID NO 40
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 40
```

```
atggagaact tgacgtcctc aggtcaccct tg                                    32

<210> SEQ ID NO 41
<211> LENGTH: 13
<212> TYPE: DNA
<213> ORGANISM: Artificial Sequence
<220> FEATURE:
<223> OTHER INFORMATION: amplification primers and ligase assay probes

<400> SEQUENCE: 41
taggtcacct ttt                                                         13

<210> SEQ ID NO 42
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 42
gctcttcaga gatgtgtcca ctagtcatgc tt                                    32

<210> SEQ ID NO 43
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 43
atggagaact tgacgtcctc aaagagcgat gc                                    32

<210> SEQ ID NO 44
<211> LENGTH: 12
<212> TYPE: DNA
<213> ORGANISM: Artificial Sequence
<220> FEATURE:
<223> OTHER INFORMATION: amplification primers and ligase assay probes

<400> SEQUENCE: 44
aaagagcgat gg                                                          12

<210> SEQ ID NO 45
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 45
ctccaggttg tcctgtccac tagtcatgct t                                     31

<210> SEQ ID NO 46
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 46
atggagaact tgacgtcctt gcaatcgcag t                                     31

<210> SEQ ID NO 47
<211> LENGTH: 12
<212> TYPE: DNA
```

<213> ORGANISM: Artificial Sequence
<220> FEATURE:
<223> OTHER INFORMATION: ampilification primers and ligase assay probes

<400> SEQUENCE: 47
agcaatcgca gg                                                         12

<210> SEQ ID NO 48
<211> LENGTH: 29
<212> TYPE: DNA
<213> ORGANISM: Artificial Sequence
<220> FEATURE:
<223> OTHER INFORMATION: ampilification primers and ligase assay probes

<400> SEQUENCE: 48
ccgcgcgtcg ttgtccacta gtcatgctt                                       29

<210> SEQ ID NO 49
<211> LENGTH: 32
<212> TYPE: DNA
<213> ORGANISM: Artificial Sequence
<220> FEATURE:
<223> OTHER INFORMATION: ampilification primers and ligase assay probes

<400> SEQUENCE: 49
atggagaact tgacgtcctc tgcaatcgca gt                                   32

<210> SEQ ID NO 50
<211> LENGTH: 11
<212> TYPE: DNA
<213> ORGANISM: Artificial Sequence
<220> FEATURE:
<223> OTHER INFORMATION: ampilification primers and ligase assay probes

<400> SEQUENCE: 50
gcaatcgcag g                                                          11

<210> SEQ ID NO 51
<211> LENGTH: 29
<212> TYPE: DNA
<213> ORGANISM: Artificial Sequence
<220> FEATURE:
<223> OTHER INFORMATION: ampilification primers and ligase assay probes

<400> SEQUENCE: 51
ccgcgcgtcg ttgtccacta gtcatgctt                                       29

<210> SEQ ID NO 52
<211> LENGTH: 32
<212> TYPE: DNA
<213> ORGANISM: Artificial Sequence
<220> FEATURE:
<223> OTHER INFORMATION: ampilification primers and ligase assay probes

<400> SEQUENCE: 52
atggagaact tgacgtcctc cctccaggtt gt                                   32

<210> SEQ ID NO 53
<211> LENGTH: 11
<212> TYPE: DNA
<213> ORGANISM: Artificial Sequence
<220> FEATURE:
<223> OTHER INFORMATION: ampilification primers and ligase assay probes

<400> SEQUENCE: 53
ctccaggttg a                                                          11

<210> SEQ ID NO 54
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 54
ccggagccta gttgtccact agtcatgctt                               30

<210> SEQ ID NO 55
<211> LENGTH: 33
<212> TYPE: DNA
<213> ORGANISM: Artificial Sequence
<220> FEATURE:
<223> OTHER INFORMATION: amplification primers and ligase assay probes

<400> SEQUENCE: 55
atggagaact tgacgtcctc actctgaaag agc                            33

<210> SEQ ID NO 56
<211> LENGTH: 13
<212> TYPE: DNA
<213> ORGANISM: Artificial Sequence
<220> FEATURE:
<223> OTHER INFORMATION: amplification primers and ligase assay probes

<400> SEQUENCE: 56
actctgaaag agt                                                 13

<210> SEQ ID NO 57
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 57
gatgcctcca ggttgtccac tagtcatgct t                             31

<210> SEQ ID NO 58
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 58
atggagaact tgacgtcctc tcccgatagg tc                            32

<210> SEQ ID NO 59
<211> LENGTH: 12
<212> TYPE: DNA
<213> ORGANISM: Artificial Sequence
<220> FEATURE:
<223> OTHER INFORMATION: amplification primers and ligase assay probes

<400> SEQUENCE: 59
tcccgatagg tt                                                  12

<210> SEQ ID NO 60
<211> LENGTH: 32
<212> TYPE: DNA
<213> ORGANISM: Artificial Sequence
<220> FEATURE:

```
<223> OTHER INFORMATION: amplification primers and ligase assay probes

<400> SEQUENCE: 60
acctttggct cttctgtcca ctagtcatgc tt                                    32

<210> SEQ ID NO 61
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 61
atggagaact tgacgtcctc cgcgcgagcc                                       30

<210> SEQ ID NO 62
<211> LENGTH: 9
<212> TYPE: DNA
<213> ORGANISM: Artificial Sequence
<220> FEATURE:
<223> OTHER INFORMATION: amplification primers and ligase assay probes

<400> SEQUENCE: 62 gcgcgagcg                                                               9

<210> SEQ ID NO 63
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 63
ctcccaggtc atctgtccac tagtcatgct t                                     31

<210> SEQ ID NO 64
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 64
atggagaact tgacgtcctc ctgcaggctc g                                     31

<210> SEQ ID NO 65
<211> LENGTH: 10
<212> TYPE: DNA
<213> ORGANISM: Artificial Sequence
<220> FEATURE:
<223> OTHER INFORMATION: amplification primers and ligase assay probes

<400> SEQUENCE: 65
tgcaggctcc                                                             10

<210> SEQ ID NO 66
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 66
gatggcgggt gatgtccact agtcatgctt                                       30
```

```
<210> SEQ ID NO 67
<211> LENGTH: 33
<212> TYPE: DNA
<213> ORGANISM: Artificial Sequence
<220> FEATURE:
<223> OTHER INFORMATION: amplification primers and ligase assay probes

<400> SEQUENCE: 67
atggagaact tgacgtcctc agtctgaaag atc                                    33

<210> SEQ ID NO 68
<211> LENGTH: 13
<212> TYPE: DNA
<213> ORGANISM: Artificial Sequence
<220> FEATURE:
<223> OTHER INFORMATION: amplification primers and ligase assay probes

<400> SEQUENCE: 68
agtctgaaag atg                                                          13

<210> SEQ ID NO 69
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 69
agcagaacag aaagtgtcca ctagtcatgc tt                                     32

<210> SEQ ID NO 70
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 70
atggagaact tgacgtcctc tcactgagga tc                                     32

<210> SEQ ID NO 71
<211> LENGTH: 12
<212> TYPE: DNA
<213> ORGANISM: Artificial Sequence
<220> FEATURE:
<223> OTHER INFORMATION: amplification primers and ligase assay probes

<400> SEQUENCE: 71
tcactgagga tt                                                           12

<210> SEQ ID NO 72
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 72
gagctgctgc tgtgtccact agtcatgctt                                        30

<210> SEQ ID NO 73
<211> LENGTH: 33
<212> TYPE: DNA
<213> ORGANISM: Artificial Sequence
<220> FEATURE:
<223> OTHER INFORMATION: amplification primers and ligase assay probes
```

<400> SEQUENCE: 73
atggagaact tgacgtcctc ggagtttgtg tac					33

<210> SEQ ID NO 74
<211> LENGTH: 14
<212> TYPE: DNA
<213> ORGANISM: Artificial Sequence
<220> FEATURE:
<223> OTHER INFORMATION: amplification primers and ligase assay probes

<400> SEQUENCE: 74
aggagtttgt gtaa					14

<210> SEQ ID NO 75
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 75
aagaaccaaa aggtgtccac tagtcatgct t					31

<210> SEQ ID NO 76
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 76
atggagaact tgacgtcctc ctgtagctgc					30

<210> SEQ ID NO 77
<211> LENGTH: 11
<212> TYPE: DNA
<213> ORGANISM: Artificial Sequence
<220> FEATURE:
<223> OTHER INFORMATION: amplification primers and ligase assay probes

<400> SEQUENCE: 77
cctgtagctg t					11

<210> SEQ ID NO 78
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 78
agcagccgct ggtgtccact agtcatgctt					30

<210> SEQ ID NO 79
<211> LENGTH: 30
<212> TYPE: DNA
<213> ORGANISM: Artificial Sequence
<220> FEATURE:
<223> OTHER INFORMATION: amplification primers and ligase assay probes

<400> SEQUENCE: 79
atggagaact tgacgtcctc cggcccccac					30

<210> SEQ ID NO 80
<211> LENGTH: 10

```
<212> TYPE: DNA
<213> ORGANISM: Artificial Sequence
<220> FEATURE:
<223> OTHER INFORMATION: amplification primers and ligase assay probes

<400> SEQUENCE: 80
cggcccccat                                                              10

<210> SEQ ID NO 81
<211> LENGTH: 31
<212> TYPE: DNA
<213> ORGANISM: Artificial Sequence
<220> FEATURE:
<223> OTHER INFORMATION: amplification primers and ligase assay probes

<400> SEQUENCE: 81
gacctggtcc ctttgtccac tagtcatgct t                                      31

<210> SEQ ID NO 82
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 82
atggagaact tgacgtcctc ggggtaatga cg                                     32

<210> SEQ ID NO 83
<211> LENGTH: 13
<212> TYPE: DNA
<213> ORGANISM: Artificial Sequence
<220> FEATURE:
<223> OTHER INFORMATION: amplification primers and ligase assay probes

<400> SEQUENCE: 83
aggggtaatg aca                                                          13

<210> SEQ ID NO 84
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 84
ctgagaagct gatgtgtcca ctagtcatgc tt                                     32

<210> SEQ ID NO 85
<211> LENGTH: 32
<212> TYPE: DNA
<213> ORGANISM: Artificial Sequence
<220> FEATURE:
<223> OTHER INFORMATION: amplification primers and ligase assay probes

<400> SEQUENCE: 85
atggagaact tgacgtcctc catcctggct tc                                     32

<210> SEQ ID NO 86
<211> LENGTH: 12
<212> TYPE: DNA
<213> ORGANISM: Artificial Sequence
<220> FEATURE:
<223> OTHER INFORMATION: amplification primers and ligase assay probes

<400> SEQUENCE: 86
```

```
catcctggct ta                                                                    12

<210> SEQ ID NO 87
<211> LENGTH: 30
<212> TYPE: DNA
<213> ORGANISM: Artificial Sequence
<220> FEATURE:
<223> OTHER INFORMATION: ampilification primers and ligase assay probes

<400> SEQUENCE: 87
ggtgctgcgc attgtccact agtcatgctt                                                 30

<210> SEQ ID NO 88
<211> LENGTH: 31
<212> TYPE: DNA
<213> ORGANISM: Artificial Sequence
<220> FEATURE:
<223> OTHER INFORMATION: ampilification primers and ligase assay probes

<400> SEQUENCE: 88
atggagaact tgacgtcctt ggagagtcct c                                               31

<210> SEQ ID NO 89
<211> LENGTH: 12
<212> TYPE: DNA
<213> ORGANISM: Artificial Sequence
<220> FEATURE:
<223> OTHER INFORMATION: ampilification primers and ligase assay probes

<400> SEQUENCE: 89
tggagagtcc tt                                                                    12

<210> SEQ ID NO 90
<211> LENGTH: 29
<212> TYPE: DNA
<213> ORGANISM: Artificial Sequence
<220> FEATURE:
<223> OTHER INFORMATION: ampilification primers and ligase assay probes

<400> SEQUENCE: 90
gacgggcccc ctgtccacta gtcatgctt                                                  29
```